(12) United States Patent
Stilz et al.

(10) Patent No.: US 6,838,439 B2
(45) Date of Patent: Jan. 4, 2005

(54) HETEROCYTES AS INHIBITORS OF LEUCOCYTE ADHESION AND AS VLA-4 ANTAGONISTS

(75) Inventors: Hans Ulrich Stilz, Frankfurt (DE); Volkmar Wehner, Sandberg (DE); Christoph Huls, Wackernheim (DE); Dirk Seiffge, Mainz-Kostheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 594 days.

(21) Appl. No.: 09/995,631

(22) Filed: Nov. 29, 2001

(65) Prior Publication Data

US 2002/0065391 A1 May 30, 2002

Related U.S. Application Data

(63) Continuation of application No. 08/971,966, filed on Nov. 17, 1997, now abandoned.

(30) Foreign Application Priority Data

Nov. 15, 1996 (DE) .......................................... 196 47 381

(51) Int. Cl.[7] .............................................. C07K 5/06
(52) U.S. Cl. ........................... 514/19; 514/18; 514/360; 530/331; 548/100
(58) Field of Search ........................... 514/18, 19, 360; 530/331; 548/100

(56) References Cited

U.S. PATENT DOCUMENTS

| | | | |
|---|---|---|---|
| 5,424,293 A | 6/1995 | Zoller et al. | 514/20 |
| 5,463,071 A | 10/1995 | Himmelsbach et al. | 548/251 |
| 5,710,159 A | 1/1998 | Voss et al. | 514/275 |
| 5,939,556 A | 8/1999 | Zoller et al. | 548/320.1 |
| 5,981,492 A | 11/1999 | Zoller et al. | 514/20 |
| 5,998,447 A | 12/1999 | Stilz et al. | 514/341 |
| 6,218,415 B1 | 4/2001 | Wehner et al. | 514/389 |

FOREIGN PATENT DOCUMENTS

| | | |
|---|---|---|
| EP | 0 580 008 A2 | 1/1994 |
| EP | 0 796 855 | 9/1997 |
| WO | 93-13798 | 7/1993 |
| WO | 94-15958 | 7/1994 |
| WO | 95-14008 | 5/1995 |
| WO | 95-15973 | 6/1995 |
| WO | 96-00581 | 1/1996 |
| WO | 96-06108 | 2/1996 |
| WO | 96-20216 | 7/1996 |
| WO | WO 96/2296 | 8/1996 |
| WO | WO 96/22966 | 8/1996 |
| WO | 96-33976 | 10/1996 |

OTHER PUBLICATIONS

Tomita Y., International journal of cancer. Journal international du cancer, (Mar. 16, 1995) 60 (6) 753–8.*
Higashiyama A., Cancer immunology immunotherapy : CII, 42 (4) 231–6, 1996.*
Kawasaki N., Japanese journal of cancer research : Gann, 87 (10) 1070–7, 1996.*
Elices et al., "VCAM–1 on Activated Endothelium Interacts with the Leukocyte Integrin VLA–4 at a Site Distinct", Cell, vol. 60, (1990) pp. 577–584.
Issekutz et al., "Rat Blood Neutrophils Express Very Late Antigen 4 and it Mediates Migration to Arthritic Joint", Journal of Exp. Med., vol. 183, (1996) pp. 2175–2184.
Holzmann, "Molecular Analysis of the Physiological and Pathophysiological Role of $a_4$– Integrins", J. Mol. Med., vol. 73, (1995) pp. 347–354.
Cronstein et al., "The Adhesion Molecules of Inflammation", Arthritis and Rheumatism, vol. 36, No. 2, (1995) pp. 147–157.

* cited by examiner

*Primary Examiner*—Jon P. Weber
*Assistant Examiner*—David Lukton
(74) *Attorney, Agent, or Firm*—Heller Ehrman White and McAuliffe LLP

(57) ABSTRACT

The present invention relates to compounds of the formula I (I)

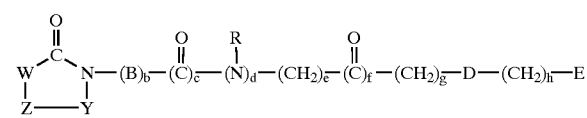

which are inhibitors of the adhesion and migration of leucocytes and/or antagonists of the adhesion receptor VLA-4 which belongs to the group of integrins. The invention also relates to processes for the preparation of formula I, pharmaceutical compositions containing compounds of formula I, and the treatment or prophylaxis of various diseases caused by or are associated with excess leucocyte adhesion and/or leucocyte migration, as well as diseases associated with cell-cell or cell-matrix interactions, which on interactions of VLA-4 receptors with their ligands play a part of, for example, inflammatory processes, rheumatoid arthritis or allergic disorders.

16 Claims, No Drawings

SEQUENCE LISTING

<160> NUMBER OF SEQ ID NOS: 1

<210> SEQ ID NO 1
<211> LENGTH: 4
<212> TYPE: PRT
<213> ORGANISM: Homo sapiens

<400> SEQUENCE: 1

Leu Asp Val Pro
1

HETEROCYTES AS INHIBITORS OF LEUCOCYTE ADHESION AND AS VLA-4 ANTAGONISTS

This application is a continuation of U.S. Ser. No. 08/971,966 filed Nov. 17, 1997 now abandoned. The prior application is hereby incorporated herein by reference, in its entirety.

The present invention relates to compounds of the formula I

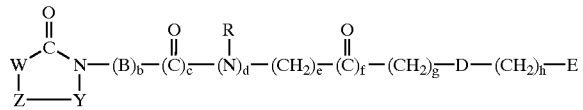

which are inhibitors of the adhesion and migration of leucocytes and/or antagonists of the adhesion receptor VLA-4 which belongs to the group of integrins. The invention also relates to processes for their preparation, to the use of compounds of the formula I for the treatment or prophylaxis of diseases which are caused by an undesired extent of leucocyte adhesion and/or leucocyte migration or which are associated therewith or in which cell-cell or cell-matrix interactions which are based on interactions of VLA-4 receptors with their ligands play a part, for example of inflammatory processes, of rheumatoid arthritis or of allergic disorders, and also to the use of compounds of the formula I for the production of pharmaceuticals for use in such diseases, and to pharmaceutical preparations which contain the compounds of the formula I.

The integrins are a group of adhesion receptors which play an important part in cell-cell-binding and cell-extracellular matrix-binding processes. They have an αβ-heterodimeric structure and exhibit a wide cellular distribution and a high extent of evolutive conservation. The integrins include, for example, the fibrinogen receptor on platelets, which interacts especially with the RGD sequence of fibrinogen, or the vitronectin receptor on osteoclasts, which interacts especially with the RGD sequence of vitronectin or of osteopontin. The integrins are divided into three major groups, the β2 subfamily with the representatives LFA-1, Mac-1 and p150/95, which are responsible in particular for cell-cell interactions of the immune system, and the subfamilies β1 and β3, whose representatives mainly mediate cell adhesion to components of the extracellular matrix (Ruoslahti, Annu Rev. Biochem. 1988, 57, 375). The integrins of the β1 subfamily, also called VLA proteins (very late (activation) antigen), include at least six receptors which interact specifically with fibronectin, collagen and/or laminin as ligands. Within the VLA family, the integrin VLA-4 (α4β1) is atypical in so far as it is mainly restricted to lymphoid and myeloid cells and is responsible in these for cell-cell interactions with a large number of other cells. For example, VLA-4 mediates the interaction of T and B lymphocytes with the heparin II-binding fragment of human plasma fibronectin (FN). The binding of VLA-4 with the heparin II-binding fragment of plasma fibronectin is especially based on an interaction with an (SEQ ID NO: 1) LDVP sequence. In contrast to the fibrinogen or vitronectin receptor, VLA-4 is not a typical RGD-binding integrin (Kilger and Holzmann, J. Mol. Meth. 1995, 73, 347).

The leucocytes circulating in the blood normally exhibit only a low affinity for the vascular endothelial cells which line the blood vessels. Cytokines which are released from inflamed tissue cause the activation of endothelial cells and thus the expression of a large number of cell surface antigens. These include, for example, the adhesion molecules ELAM-1 (endothelial cell adhesion molecule-1; also designated as E-selectin), which, inter alia, binds neutrophils, ICAM-1 (intercellular adhesion molecule-1), which interacts with LFA-1 (leucocyte function-associated antigen 1) on leucocytes, and VCAM-1 (vascular cell adhesion molecule-1), which binds various leucocytes, inter alia lymphocytes (Osborn et al., Cell 1989, 59, 1203). VCAM-1, like ICAM-1, is a member of the immunoglobulin gene superfamily. VCAM-1 (first known as INCAM-110) was identified as an adhesion molecule which is induced on endothelial cells by inflammatory cytokines such as TNF and IL-1 and lipopolysaccharides (LPS). Elices et al. (Cell 1990, 60, 577) showed that VLA-4 and VCAM-1 form a receptor-ligand pair which mediates the adhesion of lymphocytes to activated endothelium. The binding of VCAM-1 to VLA-4 does not take place here due to an interaction of the VLA-4 with an RGD sequence; such one is not contained in VCAM-1 (Bergelson et al., Current Biology 1995, 5, 615). VLA-4, however, also occurs on other leucocytes, and the adhesion of leucocytes other than lymphocytes is also mediated via the VCAM-1/VLA-4 adhesion mechanism. VLA-4 thus represents an individual example of a β1 integrin receptor which, via the ligands VCAM-1 and fibronectin, plays an important part in cell-cell interactions and in cell-extracellular matrix interactions.

The cytokine-induced adhesion molecules play an important part in the recruitment of leucocytes into extravascular tissue regions. Leucocytes are recruited into inflammatory tissue regions by cell adhesion molecules which are expressed on the surface of endothelial cells and serve as ligands for leucocyte cell surface proteins or protein complexes (receptors) (the terms ligand and receptor can also be used vice versa). Leucocytes from the blood must first adhere to endothelial cells before they can migrate into the synovium. Since VCAM-1 binds to cells which carry the integrin VLA-4 (α4β1), such as eosinophils, T and B lymphocytes, monocytes or also neutrophils, it and the VCAM-1/VLA-4 mechanism have the function of recruiting cells of this type from the blood stream into areas of infection and inflammatory foci (Elices et al., Cell 1990, 60, 577; Osborn, Cell 1990, 62, 3; Issekutz et al., J. Exp. Med. 1996, 183, 2175).

The VCAM-1/VLA-4 adhesion mechanism has been connected with a number of physiological and pathological processes. Apart from cytokine-induced endothelium, VCAM-1 is additionally expressed, inter alia, by the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue during heart and kidney transplant rejection and by intestinal tissue in graft-versus-host disease. VCAM-1 is also found to be expressed on those tissue areas of the arterial endothelium which correspond to early arteriosclerotic plaques of a rabbit model. Additionally, VCAM-1 is expressed on follicular dendritic cells of human lymph nodes and is found on stroma cells of the bone marrow, for example in the mouse. The latter finding points to a function of VCAM-1 in B-cell development. Apart from cells of hematopoietic origin, VLA-4 is also found, for example, on melanoma cell lines, and the VCAM-1/VLA-4 adhesion mechanism is connected with the metastasis of such tumors (Rice et al., Science 1989, 246, 1303).

The main form in which VCAM-1 occurs in vivo on endothelial cells and which is the dominant form in vivo is designated as VCAM-7D and carries seven immunoglobulin domains. The domains 4, 5 and 6 are similar in their amino acid sequences to the domains 1, 2 and 3. The fourth domain is removed in a further form, consisting of six domains, designated here as VCAM-6D, by alternative splicing. VCAM-6D can also bind VLA-4 -expressing cells.

Further details on VLA-4, VCAM-1, integrins and adhesion proteins are found, for example, in the articles by Kilger and Holzmann, J. Mol. Meth. 1995, 73, 347; Elices, Cell Adhesion in Human Disease, Wiley, Chichester 1995, p. 79; Kuijpers, Springer Semin. Immunopathol. 1995, 16, 379.

On account of the role of the VCAM-1/VLA-4 mechanism in cell adhesion processes which are of importance, for example, in infections, inflammations or atherosclerosis, it has been attempted by means of interventions into these adhesion processes to control diseases, in particular, for example, inflammations (Osborn et al., Cell 1989, 59, 1203). A method of doing this is the use of monoclonal antibodies which are directed against VLA-4. Monoclonal antibodies (mAB) of this type which as VLA-4 antagonists block the interaction between VCAM-1 and VLA-4, are known. Thus, for example, the anti-VLA-4 mAB HP2/1 and HP1/3 inhibit the adhesion of VLA-4-expressing Ramos cells (B-cell-like cells) to human umbilical cord endothelial cells and to VCAM-1-transfected COS cells.

The anti-VCAM-1 mAB 4B9 likewise inhibits the adhesion of Ramos cells, Jurkat cells (T-cell-like cells) and HL60 cells (granulocyte-like cells) to COS cells transfected with genetic constructs which cause VCAM-6D and VCAM-7D to be expressed. In vitro data with antibodies which are directed against the α4 subunit of VLA-4 show that the adhesion of lymphocytes to synovial endothelial cells is blocked, an adhesion which plays a part in rheumatoid arthritis (van Dinther-Janssen et al., J. Immunol. 1991, 147, 4207).

In vivo experiments have shown that an experimental autoimmune encephalomyelitis can be inhibited by anti-α4 mAB. The migration of leucocytes into an inflammatory focus is likewise blocked by a monoclonal antibody against the α4 chain of VLA-4. The influencing of the VLA-4-dependent adhesion mechanism by antibodies was also investigated in an asthma model in order to investigate the role of VLA-4 in the recruitment of leucocytes in inflamed lung tissue (U.S. Ser. No. 07/821,768 now abandoned; EP-A-626 861). The administration of anti-VLA-4 antibodies inhibited the late-phase reaction and respiratory tract overreaction in allergic sheep.

The VLA-4-dependent cell adhesion mechanism was also investigated in a primate model of inflammatory bowel disease (IBD). In this model, which corresponds to ulcerative colitis in man, the administration of anti-VLA-4 antibodies resulted in a significant reduction in the acute inflammation.

Moreover, it was possible to show that VLA-4-dependent cell adhesion plays apart in the following clinical conditions including the following chronic inflammatory processes: rheumatoid arthritis (Cronstein and Weismann, Arthritis Rheum. 1993, 36, 147; Elices et al., J. Clin. Invest. 1994, 93, 405), diabetes mellitus (Yang et al., Proc. Natl. Acad. Sci. USA 1993, 90, 10494), systemic lupus erythematosus (Takeuchi et al., J. Clin. Invest. 1993, 92, 3008), allergies of the delayed type (type IV allergy) (Elices et al., Clin. Exp. Rheumatol. 1993, 11, p.77), multiple sclerosis (Yednock et al., Nature 1992, 356, 63), malaria (Ockenhouse et al., J. Exp. Med. 1992, 176, 1183), arteriosclerosis (Obrien et al., J. Clin. Invest. 1993, 92, 945), transplantation (Isobe et al., Transplantation Proceedings 1994, 26, 867–868), various malignancies, for example melanoma (Renkonen et al., Am. J. Pathol. 1992, 140, 763), lymphoma (Freedman et al., Blood 1992, 79, 206) and others (Albelda et al., J. Cell Biol. 1991, 114, 1059).

VLA-4 blocking by suitable antagonists accordingly offers effective therapeutic possibilities, in particular, for example, of treating various inflammatory conditions including asthma and IBD. The particular relevance of VLA-4 antagonists for the treatment of rheumatoid arthritis in this respect results, as already stated, from the fact that leucocytes from the blood must first adhere to endothelial cells before they can migrate into the synovium, and that the VLA-4 receptor plays a part in this adhesion. The fact that VCAM-1 is induced by inflammatory agents on endothelial cells (Osborn, Cell 1990, 62, 3; Stoolman, Cell 1989, 56, 907), and the recruitment of various leucocytes into areas of infection and inflammatory foci has already been dealt with above. In this respect, T cells adhere to activated endothelium mainly via the LFA-1/ICAM-1and VLA-4/VCAM-1 adhesion mechanisms (Springer, Cell 1994, 76, 301). On most synovial T cells, the binding capacity of VLA-4 for VCAM-1 is increased in rheumatoid arthritis (Postigo et al., J. Clin. Invest. 1992, 89, 1445). Additionally, an increased adhesion of synovial T cells to fibronectin has been observed (Laffon et al., J. Clin. Invest. 1991, 88, 546; Morales-Ducret et al., J. Immunol. 1992, 149, 1424). VLA-4 is also upregulated both in the course of its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective prevention of illness has been observed (Barbadillo et al., Springer Semin. Immunopathol. 1995, 16, 427). VLA-4 is thus an important therapeutic target molecule.

The abovementioned VLA-4 antibodies and the use of antibodies as VLA-4 antagonists are described in the Patent Applications WO-A-93/13798, WO-A-93/15764, WO-A-94/16094, WO-A-94/17828 and WO-A-95/19790. In the Patent Applications WO-A-94/15958, WO-A-95/15973, WO-A-96/00581, WO-A-96/06108 and WO-A-96/20216, peptide compounds are described as VLA-4 antagonists. The use of antibodies and peptide compounds as pharmaceuticals, however, is afflicted with disadvantages, for example lack of oral availability, easy degradability or immunogenic action on longer-term use, and there is thus a need for VLA-4 antagonists having a favorable profile of properties for use in therapy and prophylaxis.

WO-A-95/14008 describes substituted 5-membered ring heterocycles which have an amino, amidino or guanidino function at the N-terminal end of the molecule and which exhibit platelet aggregation-inhibiting activity. The German Patent Application 19635522.2 describes heterocycles which are inhibitors of bone resorption. WO-A-96/33976 (and the German Patent Application 19515177.1) describes certain hydantoin derivatives having a 4-cyanophenyl radical in the 4-position of the hydantoin ring, which are intermediates for the preparation of active compounds which are described in WO-A-95/14008. Pharmacological actions of these cyanophenylhydantoin derivatives, however, are not disclosed. The present invention relates to further heterocyclic compounds which are VLA-4 antagonists and/or inhibitors of leucocyte adhesion.

The present invention relates to compounds of the formula I

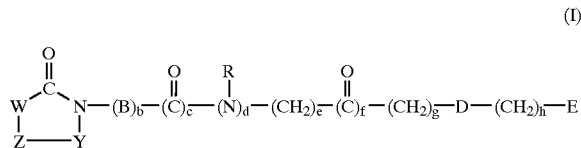

(I)

in which

W is $R^1$—A—$C(R^{13})$ or $R^1$—A—CH=C;
Y is a carbonyl, thiocarbonyl or methylene group;
Z is $N(R^0)$, oxygen, sulfur or a methylene group;
A is a bivalent radical selected from the group consisting of $(C_1–C_6)$-alkylene, $(C_3–C_{12})$-cycloalkylene, $(C_1–C_6)$-alkylene-$(C_3–C_{12})$-cycloalkyl, phenylene, phenylene-$(C_1–C_6)$-alkyl, $(C_1–C_6)$-alkylenephenyl, $(C_1–C_6)$-alkylenephenyl-$(C_1–C_6)$-alkyl, phenylene-$(C_2–C_6)$-alkenyl or a bivalent radical of a 5- or 6-membered saturated or unsaturated ring which can contain 1 or 2 nitrogen atoms and can be mono- or disubstituted by $(C_1–C_6)$-alkyl or doubly bonded oxygen or sulfur, or is a direct bond;
B is a bivalent radical from the group consisting of $(C_1–C_6)$-alkylene, $(C_2–C_6)$-alkenylene, phenylene, phenylene-$(C_1–C_3)$-alkyl, and $(C_1–C_3)$-alkylenephenyl, where the bivalent $(C_1–C_6)$-alkylene radical can be unsubstituted or substituted by a radical from the group consisting of $(C_1–C_8)$-alkyl, $(C_2–C_8)$-alkenyl, $(C_2–C_8)$-alkynyl, $(C_3–C_{10})$-cycloalkyl, $(C_3–C_{10})$-cycloalkyl-$(C_1–C_6)$-alkyl, optionally substituted $(C_6–C_{14})$-aryl, $(C_6–C_{14})$-aryl-$(C_1–C_6)$-alkyl optionally substituted in the aryl radical, optionally substituted heteroaryl and heteroaryl-$(C_1–C_6)$-alkyl optionally substituted in the heteroaryl radical;
D is $C(R^2)(R^3)$, $N(R^3)$ or CH=$C(R^3)$;
E is tetrazolyl, $(R^8O)_2P(O)$, $HOS(O)_2$, $R^9NHS(O)_2$ or $R^{10}CO$;
R is hydrogen, $(C_1–C_8)$-alkyl, $(C_3–C_{12})$-cycloalkyl, $(C_3–C_{12})$-cycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl or heteroaryl-$(C_1–C_8)$-alkyl optionally substituted in the heteroaryl radical, where alkyl radicals can be mono- or polysubstituted by fluorine;
$R^0$ is hydrogen, $(C_1–C_8)$-alkyl, $(C_3–C_{12})$-cycloalkyl, $(C_3–C_{12})$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, $(C_6–C_{12})$-tricycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl, heteroaryl-$(C_1–C_8)$-alkyl optionally substituted in the heteroaryl radical, CHO, $(C_1–C_8)$-alkyl-CO, $(C_3–C_{12})$-cycloalkyl-CO, $(C_3–C_{12})$-cycloalkyl-$(C_1–C_8)$-alkyl-CO, $(C_6–C_{12})$-bicycloalkyl-CO, $(C_6–C_{12})$-bicycloalkyl-$(C_1–C_8)$-alkyl-CO, $(C_6–C_{12})$-tricycloalkyl-CO, $(C_6–C_{12})$-tricycloalkyl-$(C_1–C_8)$-alkyl-CO, optionally substituted $(C_6–C_{14})$-aryl-CO, $(C_6–C_{14})$-aryl-$(C_1–C_8)$-alkyl-CO optionally substituted in the aryl radical, optionally substituted heteroaryl-CO, heteroaryl-$(C_1–C_8)$-alkyl-CO optionally substituted in the heteroaryl radical, $(C_1–C_8)$-alkyl-$S(O)_n$, $(C_3–C_{12})$-cycloalkyl-$S(O)_n$, $(C_3–C_{12})$-cycloalkyl-$(C_1–C_8)$-alkyl-$S(O)_n$, $(C_6–C_{12})$-bicycloalkyl-$S(O)_n$, $(C_6–C_{12})$-bicycloalkyl-$(C_1–C_8)$-alkyl-$S(O)_n$, $(C_6–C_{12})$-tricycloalkyl-$S(O)_n$, $(C_6–C_{12})$-tricycloalkyl-$(C_1–C_8)$-alkyl-$S(O)_n$, optionally substituted $(C_6–C_{14})$-aryl-$S(O)_n$, $(C_6–C_{14})$-aryl-$(C_1–C_8)$-alkyl-$S(O)_n$ optionally substituted in the aryl radical, optionally substituted heteroaryl-$S(O)_n$ or heteroaryl-$(C_1–C_8)$-alkyl-$S(O)_n$ optionally substituted in the heteroaryl radical, where n is 1 or 2;
$R^1$ is one of the radicals —S—$R^{21}$, —S—S—$R^{21}$, —S(O)—$R^{22}$, —S(O)$_2$—$R^{22}$, —S—O$R^{21}$, —S(O)—O$R^{21}$, —S(O)$_2$—O$R^{21}$, —S—N($R^{21}$)—$R^{28}$, —S(O)—N($R^{21}$)—$R^{28}$, —S(O)$_2$—N($R^{21}$)—$R^{28}$, —S—C(O)—$R^{21}$, —S—C(O)—O$R^{22}$, —S—C(S)—S$R^{22}$, —S—C(O)—N($R^{21}$)—$R^{28}$, —S—C(S)—N($R^{21}$)—$R^{28}$, —O—C(O)—$R^{21}$, —O—C(S)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—O$R^{21}$, —O—S(O)—O$R^{21}$, —O—S(O)$_2$—N($R^{21}$)—$R^{28}$, —O—S(O)—N($R^{21}$)—$R^{28}$, —O—S(O)$_2$—$R^{22}$, —O—S(O)—$R^{22}$, —O—P(O)(O$R^{21}$)$_2$, —O—P(O)(O$R^{21}$)—N($R^{21}$)—$R^{28}$, —O—P(O)(N($R^{21}$)—$R^{28}$)$_2$, —N($R^{29}$)—C(O)—O$R^{22}$, —N($R^{28}$)—C(O)—S$R^{22}$, —N($R^{28}$)—C(S)—O$R^{22}$, —N($R^{28}$)—C(S)—S$R^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —N($R^{28}$)—P(O)(O$R^{21}$)$_2$, —N($R^{28}$)—P(O)(O$R^{21}$)—N($R^{21}$)—$R^{28}$, —N($R^{28}$)—P(O)(N($R^{21}$)—$R^{28}$)$_2$, —N($R^{28}$)—P(O)($R^{22}$)—O$R^{21}$, —N($R^{28}$)—P(O)($R^{22}$)—N($R^{21}$)$R^{28}$, —N($R^{28}$)—P(O)($R^{22}$)$_2$, —P(O)(O$R^{21}$)$_2$, —P(O)(O$R^{21}$)—N($R^{21}$)—$R^{28}$, —P(O)(N($R^{21}$)—$R^{28}$)$_2$, —P(O)($R^{22}$)—O$R^{21}$, —P(O)($R^{22}$)—N($R^{21}$)—$R^{28}$, —P(O)($R^{22}$)$_2$, —C(S)—$R^{21}$, —C(S)—S$R^{21}$, —C(S)—N($R^{21}$)—$R^{28}$, cyano, halogen, nitro or methylenedioxy or the radical of an optionally substituted, 5- to 14-membered, mono- or polycyclic, saturated or unsaturated heterocyclic ring of the formula

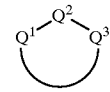

in which
$Q^1$ is —$C(R^{21})_2$—, =$C(R^{21})$—, —$N(R^{28})$—, —O— or —S—;
$Q^2$ is —S(O)— or —S(O)$_2$—;
$Q^3$ is —$C(R^{21})_2$—, =$C(R^{21})$—, —$N(R^{28})$—, —O—, —S—, —$C(R^{21})$(—)— or —N(—)—,
where the heterocyclic ring can be bonded to the group A via the free bond in the groups —$C(R^{21})$(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;
$R^2$ is hydrogen, $(C_1–C_8)$-alkyl, optionally substituted $(C_6–C_{14})$-aryl, $(C_6–C_{14})$-aryl-$(C_1–C_1$ alkyl-alkyl optionally substituted in the aryl radical or $(C_3–C_8)$-cycloalkyl;
$R^3$ is hydrogen, $(C_1–C_8)$ alkyl, optionally substituted $(C_6–C_{14})$-aryl, $(C_6–C_{14})$-aryl-$(C_1–C_8)$-alkyl optionally substituted in the aryl radical, $(C_3–C_8)$-cycloalkyl, $(C_2–C_8)$-alkenyl, $(C_2–C_8)$-alkynyl, $(C_2–C_8)$-alkenylcarbonyl, $(C_2–C_8)$-alkynylcarbonyl, pyridyl, $R^{11}$NH, $R^4$CO, COO$R^4$, CON(CH$_3$)$R^4$, CONHR$^4$, CSNHR$^4$, COO$R^{15}$, CON(CH$_3$)$R^{15}$ or CONHR$^{15}$;
$R^4$ is hydrogen or $(C_1–C_{28})$-alkyl which can optionally be mono- or polysubstituted by identical or different radicals from the group consisting of hydroxyl, hydroxycarbonyl, aminocarbonyl, mono- or di-(($C_1$–$C_{18}$)-alkyl)-aminocarbonyl, amino-($C_2$–$C_{18}$)-alkylaminocarbonyl, amino-($C_1$–$C_3$)-alkylphenyl-($C_1$–$C_3$)-alkylaminocarbonyl, ($C_1$–$C_{18}$)-alkylcarbonylamino-($C_1$–$C_3$)-alkylphenyl-($C_1$–$C_3$)-alkylaminocarbonyl, ($C_1$–$C_{18}$)-alkylcarbonylamino-($C_2$–$C_{18}$)-alkylaminocarbonyl, ($C_6$–$C_{14}$)-aryl-($C_1$–$C_8$)-alkoxycarbonyl which can also be substituted in the aryl radical, amino, mercapto, ($C_1$–$C_{18}$)-alkoxy, ($C_1$–$C_{18}$)-alkoxycarbonyl, Het-CO, optionally substituted ($C_3$–$C_8$)-cycloalkyl, HOS(O)$_2$-($C_1$–$C_3$)-alkyl, $R^9$NHS(O)$_2$—($C_1$–$C_3$)-alkyl, ($R^8$O)$_2$P(O)—($C_1$–$C_3$)-alkyl, tetrazolyl-($C_1$–$C_3$)-alkyl, halogen, nitro, trifluoromethyl or the radical $R^5$;

$R^5$ is optionally substituted ($C_6$–$C_{14}$)-aryl, ($C_6$–$C_{14}$)-aryl-($C_1$–$C_8$)-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6$CO—, where the aryl radical and, independently thereof, the heterocyclic radical can be mono- or polysubstituted by identical or different radicals from the group consisting of ($C_1$–$C_{18}$)-alkyl, ($C_1$–$C_{18}$)-alkoxy, halogen, nitro, amino and trifluoromethyl;

$R^6$ is $R^7R^8$N, $R^7$O or $R^7$S or an amino acid side chain, a natural or unnatural amino acid, imino acid, optionally N—($C_1$–$C_8$)-alkylated or N—(($C_6$–$C_{14}$)-aryl-($C_1$–$C_8$)-alkylated) azaamino acid or a dipeptide radical which can also be substituted in the aryl radical and/or reduced in the peptide bond to —NH—CH$_2$—, and their esters and amides, where hydrogen or hydroxymethyl can optionally stand in place of of free functional groups and/or where free functional groups can be protected by protective groups customary in peptide chemistry;

$R^7$ is hydrogen, ($C_1$–$C_{18}$)-alkyl, ($C_6$–$C_{14}$)-aryl-($C_1$–$C_8$)-alkyl, ($C_1$–$C_{18}$)-alkylcarbonyl, ($C_1$–$C_{18}$)-alkoxycarbonyl, ($C_6$–$C_{14}$)-arylcarbonyl, ($C_6$–$C_{14}$)-aryl-($C_1$–$C_8$)-alkylcarbonyl or ($C_6$–$C_{14}$)-aryl-($C_1$–$C_{18}$)-alkyloxycarbonyl, where the alkyl groups can optionally be substituted by an amino group and/or where the aryl radicals can be mono- or polysubstituted, preferably monosubstituted, by identical or different radicals from the group consisting of ($C_1$–$C_8$)-alkyl, ($C_1$–$C_8$)-alkoxy, halogen, nitro, amino and trifluoromethyl, or $R^7$ is a natural or unnatural amino acid, imino acid, optionally N—($C_1$–$C_8$)-alkylated or N—(($C_6$–$C_{14}$)-aryl-($C_1$–$C_8$)-alkylated) azaamino acid or a dipeptide radical which can also be substituted in the aryl radical and/or reduced in the peptide bond to —NH—CH$_2$—;

$R^8$ is hydrogen, ($C_1$–$C_{18}$)-alkyl, optionally substituted ($C_6$–$C_{14}$)-aryl or ($C_6$–$C_{14}$)-aryl-($C_1$–$C_8$)-alkyl which can also be substituted in the aryl radical;

$R^9$ is hydrogen, aminocarbonyl, ($C_1$–$C_{18}$)-alkylaminocarbonyl, ($C_3$–$C_8$)-cycloalkylaminocarbonyl, optionally substituted ($C_6$–$C_{14}$)-arylaminocarbonyl, ($C_1$–$C_{18}$)-alkyl, optionally substituted ($C_6$–$C_{14}$)-aryl or ($C_3$–$C_8$)-cycloalkyl;

$R^{10}$ is hydroxyl, ($C_1$–$C_{18}$)-alkoxy, ($C_6$–$C_{14}$)-aryl-($C_1$–$C_8$)-alkoxy which can also be substituted in the aryl radical, optionally substituted ($C_6$–$C_{14}$)-aryloxy, amino or mono- or di-(($C_1$–$C_{18}$)-alkyl)amino;

$R^{11}$ is hydrogen, $R^{12a}$, $R^{12a}$—CO, H—CO, $R^{12a}$—O—CO, $R^{12b}$—CO, $R^{12b}$—CS, $R^{12a}$—S(O)$_2$ or $R^{12b}$—S(O)$_2$;

$R^{12a}$ is ($C_1$–$C_{18}$)-alkyl, ($C_2$–$C_8$)-alkenyl, ($C_2$–$C_8$)-alkynyl, ($C_3$–$C_{12}$-Cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical or the radical $R^{15}$;

$R^{12b}$ is amino, di-(($C_1$–$C_{18}$)-alkyl)-amino or $R^{12a}$—NH;

$R^{13}$ is hydrogen, ($C_1$–$C_6$)-alkyl, optionally substituted ($C_6$–$C_{14}$)-aryl, ($C_6$–$C_{14}$)-aryl-($C_1$–$C_8$)-alkyl optionally substituted in the aryl radical, ($C_3$–$C_8$)-cycloalkyl or ($C_3$–$C_8$)-cycloalkyl-($C_1$–$C_8$)-alkyl;

$R^{15}$ is $R^{16}$—($C_1$–$C_6$)-alkyl or $R^{16}$;

$R^{16}$ is a 6- to 24-membered bicyclic or tricyclic radical which is saturated or partially unsaturated and which can also contain one, two, three or four identical or different heteroatoms from the group consisting of nitrogen, oxygen and sulfur and which can also be substituted by one or more identical or different substituents from the group consisting of ($C_1$–$C_4$)-alkyl and oxo;

$R^{21}$ is hydrogen, ($C_1$–$C_8$)-alkyl, hydroxy-($C_1$–$C_8$)-alkyl, ($C_2$–$C_8$)-alkenyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can also be monosubstituted or polysubstituted by fluorine and the radicals $R^{21}$ can be identical or different if they occur two or more times;

$R^{22}$ is ($C_1$–$C_8$)-alkyl, hydroxy-($C_1$–$C_8$)-alkyl, ($C_2$–$C_8$)-alkenyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be monosubstituted or polysubstituted by fluorine and the radicals $R^{22}$ can be identical or different if they occur two or more times;

$R^{28}$ is one of the radicals $R^{21}$—, $R^{21}$N($R^{21}$)—, $R^{21}$C(O)—, $R^{22}$O—C(O)—, $R^{21}$N($R^{21}$)—C(O)— or $R^{21}$N($R^{21}$)—C(=N($R^{21}$))—;

$R^{29}$ is one of the radicals $R^{22}$—, $R^{21}$N($R^{21}$)—, $R^{21}$C(O)—, $R^{22}$O—C(O)—, $R^{21}$N($R^{21}$)—C(O)— or $R^{21}$N($R^{21}$)—C(=N($R^{21}$))—;

Het is the radical of a 5- to 10-membered, monocyclic or polycyclic heterocycle bonded via a nitrogen atom, which can be aromatic or partially unsaturated or saturated and which can contain one, two, three or four identical or different additional ring heteroatoms from the group consisting of oxygen, nitrogen and sulfur and which can be optionally substituted on carbon atoms and on additional ring nitrogen atoms, where there can be identical or different radicals $R^h$, $R^h$CO or $R^h$O—CO as substituents on additional ring nitrogen atoms and $R^h$ is hydrogen, ($C_1$–$C_8$)-alkyl, ($C_3$–$C_8$)-cycloalkyl, ($C_3$–$C_8$)-cycloalkyl-($C_1$–$C_8$)-alkyl, optionally substituted ($C_6$–$C_{14}$)-aryl or ($C_6$–$C_{14}$)-aryl-($C_1$–$C_8$)-alkyl optionally substituted in the aryl radical;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and their physiologically tolerable salts;

where, however, if simultaneously W is 4-cyanophenyl-C($R^{13}$), Y is a carbonyl group, Z is NR$^{0a}$, B is an unsubstituted methylene group, R is $R^a$, b, c and d are 1 and e, f and g are 0, then D cannot be $C(R^{2a})(R^{3a})$, where $R^{0a}$, $R^a$ and $R^{2a}$ independently of one another are hydrogen, $(C_1–C_8)$-alkyl, optionally substituted $(C_6–C_{14})$-aryl, $(C_6–C_{14})$-aryl-$(C_1–C_8)$-alkyl optionally substituted in the aryl radical or $(C_3–C_8)$-cycloalkyl and $R^{3a}$ is hydrogen, $(C_1–C_8)$-alkyl, optionally substituted $(C_6–C_{14})$-aryl, $(C_6–C_{14})$-aryl-$(C_1–C_8)$-alkyl optionally substituted in the aryl radical, $(C_3–C_8)$-cycloalkyl or 2-, 3- or 4-pyridyl.

Alkyl radicals can be straight-chain or branched. This also applies if they carry substituents or occur as substituents of other radicals, for example in alkoxy, alkoxycarbonyl or aralkyl radicals. The same applies to alkylene radicals. Examples of suitable $(C_1–C_{28})$-alkyl radicals are: methyl, ethyl, propyl, butyl, pentyl, hexyl, heptyl, octyl, decyl, undecyl, dodecyl, tridecyl, pentadecyl, hexadecyl, heptadecyl, nonadecyl, eicosyl, docosyl, tricosyl, pentacosyl, hexacosyl, heptacosyl, octacosyl, isopropyl, isobutyl, isopentyl, neopentyl, isohexyl, 3-methylpentyl, 2,3,5-trimethylhexyl, sec-butyl, tert-butyl, tert-pentyl. Preferred alkyl radicals are methyl, ethyl, propyl, isopropyl, butyl, isobutyl, sec-butyl and tert-butyl. Examples of alkylene radicals are methylene, ethylene, tri-, tetra-, penta- and hexamethylene or methylene substituted by an alkyl radical, for example methylene which is substituted by a methyl group, an ethyl group, an isopropyl group, an isobutyl group or a tert-butyl group.

Alkenyl and alkenylene radicals as well as alkynyl radicals can also be straight-chain or branched. Examples of alkenyl radicals are vinyl, 1-propenyl, alkyl, butenyl, 3-methyl-2-butenyl, examples of alkenylene radicals are vinylene or propenylene and examples of alkynyl radicals are ethynyl, 1-propynyl or propargyl.

Cycloalkyl radicals are, in particular, cyclopropyl, cyclobutyl, cyclopentyl, cyclohexyl, cycloheptyl, cyclooctyl, cyclononyl, cyclodecyl, cycloundecyl and cyclododecyl, but which can also be substituted by, for example, $(C_1–C_4)$-alkyl. Examples of substituted cycloalkyl radicals which may be mentioned are 4-methylcyclohexyl and 2,3-dimethylcyclopentyl. The same applies to cycloalkylene radicals.

The 6- to 24-membered bicyclic and tricyclic radicals $R^{16}$ are formally obtained by abstraction of a hydrogen atom from bicyclic systems or tricyclic systems. The bicyclic systems and tricyclic systems on which they are based can contain only carbon atoms as ring members, i. e. they can be bicycloalkanes or tricycloalkanes, but they can also contain one, two, three or four identical or different heteroatoms from the group consisting of nitrogen, oxygen and sulfur, i. e. they can be aza-, oxa- and thiabicyclo- and -tricycloalkanes. If heteroatoms are present, preferably one or two heteroatoms, in particular nitrogen or oxygen atoms, are present. The heteroatoms can assume any desired positions in the bi- or tricyclic structure; they can be located in the bridges, or in the case of nitrogen atoms, also at the bridgeheads. Both the bicyclo- and tricycloalkanes and their heterocyclic analogs can be completely saturated or can contain one or more double bonds. They preferably contain one or two double bonds or, in particular, are completely saturated. Both the bicyclo- and tricycloalkanes and the heterocyclic analogs and both the saturated and the unsaturated representatives can be unsubstituted or substituted in any desired suitable positions by one or more oxo groups and/or one or more identical or different $(C_1–C_4)$-alkyl groups, for example methyl or isopropyl groups, preferably methyl groups. The free bond of the bi- or tricyclic radical can be located in any desired position of the molecule; the radical can thus be bonded via a bridgehead atom or an atom in a bridge. The free bond can also be located in any desired stereochemical position, for example in an exo or an endo position.

Examples of parent structures of bicyclic ring systems from which a bicyclic radical can be derived are norbornane (=bicyclo[2.2.1]heptane), bicyclo[2.2.2]octane and bicyclo [3.2.1]octane, examples of unsaturated or substituted systems or systems containing heteroatoms are 7-azabicyclo [2.2.1]-heptane, bicyclo[2.2.2]oct-5-ene and camphor (=1, 7,7-trimethyl-2-oxobicyclo[2.2.1]heptane).

Examples of systems from which a tricyclic radical can be derived are twistane (=tricyclo[4.4.0.0$^{3.8}$]decane), adamantane (=tricyclo[3.3.1.1$^{3.7}$]-decane), noradamantane (=tricyclo[3.3.1.0$^{3.7}$]nonane), tricyclo[2.2.1.0$^{2.6}$]-heptane, tricyclo[5.3.2.0$^{4.9}$]dodecane, tricyclo[5.4.0.0$^{2.9}$]undecane or tricyclo[5.5.1.0$^{3.11}$]tridecane.

Preferably, bicyclic or tricyclic radicals representing $R^{16}$ are derived from bridged bicyclic systems or tricyclic systems, i.e. from systems in which rings together have two or more than two atoms. Bicyclic or tricyclic radicals having 6 to 18 ring members are additionally preferred, particularly preferably those having 7 to 12 ring members.

Specifically particularly preferred bi- and tricyclic radicals are the 2-norbornyl radical, both that with the free bond in the exo position and also that with the free bond in the endo position, the 2-bicyclo[3.2.1]octyl radical, the 1-adamantyl radical, the 2-adamantyl radical and the noradamantyl radical, for example the 3-noradamantyl radical. The 1- and the 2-adamantyl radicals are moreover preferred.

$(C_6–C_{14})$-aryl groups are, for example, phenyl, naphthyl, biphenylyl, anthryl or fluorenyl, where 1-naphthyl, 2-naphthyl and in particular phenyl are preferred. Aryl radicals, in particular phenyl radicals, can be mono- or polysubstituted, preferably mono-, di- or trisubstituted, by identical or different radicals from the group consisting of $(C_1–C_8)$-alkyl, in particular $(C_1–C_4)$-alkyl, $(C_1–C_8)$-alkoxy, in particular $(C_1–C_4)$-alkoxy, halogen, nitro, amino, trifluoromethyl, hydroxyl, methylenedioxy, ethylenedioxy, cyano, hydroxycarbonyl, aminocarbonyl, $(C_1–C_4)$-alkoxycarbonyl, phenyl, phenoxy, benzyl, benzyloxy, $(R^8O)_2P(O)$, $(R^8O)_2P(O)$—O—, tetrazolyl. The same applies, for example, to radicals such as aralkyl or arylcarbonyl. Aralkyl radicals are, in particular, benzyl as well as 1- and 2-naphthylmethyl, 2-, 3- and 4-biphenylylmethyl and 9-fluorenylmethyl which can also be substituted. Substituted aralkyl radicals are, for example, benzyl and naphthylmethyl substituted in the aryl moiety by one or more $(C_1–C_8)$-alkyl radicals, in particular $(C_1–C_4)$-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, 1-, 3-, 4-, 5-, 6-, 7- and 8-methyl-2-naphthylmethyl, or benzyl and naphthylmethyl substituted in the aryl moiety by one or more $(C_1–C_8)$-alkoxy radicals, in particular $(C_1–C_4)$-alkoxy radicals, for example 4-methoxybenzyl, 4-neopentyloxybenzyl, 3,5-dimethoxybenzyl, 3,4-methylenedioxybenzyl, 2,3,4-trimethoxybenzyl, further 2-, 3- and 4-nitrobenzyl, halobenzyl, for example 2-, 3- and 4-chloro- and 2-, 3- and 4-fluorobenzyl, 3,4-dichlorobenzyl, pentafluorobenzyl, trifluoromethylbenzyl, for example 3- and 4-trifluoromethylbenzyl or 3,5-bis(trifluoromethyl)benzyl.

Substituted aralkyl radicals, however, can also have different substituents. Examples of pyridyl are 2-pyridyl, 3-pyridyl and 4-pyridyl.

In monosubstituted phenyl radicals, the substituent can be located in the 2-, the 3- or the 4-position, the 3- and the 4-positions being preferred. If phenyl is disubstituted, the substituents can be in the 1,2-, 1,3- or 1,4-position relative to one another. Disubstituted phenyl can thus be substituted in the 2,3-position, the 2,4-position, the 2,5-position, the 2,6-position, the 3,4-position or the 3,5-position, relative to the linkage site. Preferably, in disubstituted phenyl radicals the two substituents are arranged in the 3-position and the 4-position, relative to the linkage site. In trisubstituted phenyl radicals the substituents can be located, for example, in the 2,3,4-position, the 2,3,5-position, the 2,4,5-position, the 2,4,6-position, the 2,3,6-position or the 3,4,5-position. The same applies for phenylene radicals which, for example, can be present as 1,4-phenylene or as 1,3-phenylene.

Phenylene-$(C_1-C_6)$-alkyl is, in particular, phenylenemethyl (—$C_6H_4$—$CH_2$—) and phenyleneethyl, $(C_1-C_6)$-alkylenephenyl is, in particular, methylenephenyl (—$CH_2$—$C_6H_4$—). Phenylene-$(C_2-C_6)$-alkenyl is, in particular, phenyleneethenyl and phenylenepropenyl.

Heteroaryl is a mono- or polycyclic aromatic radical having 5 to 14 ring members, which contains 1 to 5 heteroatoms as ring members. Examples of heteroatoms are N, O and S. If several heteroatoms are contained, these can be identical or different. Heteroaryl radicals can also be mono- or polysubstituted, preferably mono-, di- or trisubstituted, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, methylenedioxy, ethylenedioxy, cyano, hydroxycarbonyl, aminocarbonyl, $(C_1-C_4)$-alkoxycarbonyl, phenyl, phenoxy, benzyl, benzyloxy, $(R^8O)_2P(O)$, $(R^8O)_2P(O)$—O—, tetrazolyl. Preferably, heteroaryl is a mono- or bicyclic aromatic radical which contains 1, 2, 3 or 4, in particular 1 to 3, identical or different heteroatoms from the group consisting of N, O and S and which can be substituted by 1, 2, 3 or 4, in particular 1 to 3, identical or different substituents from the group consisting of $(C_1-C_6)$-alkyl, $(C_1-C_6)$-alkoxy, fluorine, chlorine, nitro, amino, trifluoromethyl, hydroxyl, $(C_1-C_4)$-alkoxycarbonyl, phenyl, phenoxy, benzyloxy and benzyl. Particularly preferably, heteroaryl is a mono- or bicyclic aromatic radical having 5 to 10 ring members, in particular a 5- to 6-membered monocyclic aromatic radical which contains 1, 2 or 3, in particular 1 or 2, identical or different heteroatoms from the group consisting of N, O and S and can be substituted by 1 or 2 identical or different substituents from the group consisting of $(C_1-C_4)$-alkyl, $(C_1-C_4)$-alkoxy, phenyl, phenoxy, benzyloxy and benzyl.

Heterocyclic rings of the formula

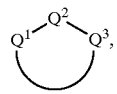

which can represent the group $R^1$, can be completely saturated in the ring or can contain one or more double bonds. In addition to the substituents in the groups $Q^1$ and $Q^3$, these heterocyclic rings can additionally carry one or more further, identical or different radicals $R^{21}$ and/or halogen atoms as substituents. The meanings —$C(R^{21})$(—)— and —N(—)— contained in the definition of $Q^3$ are to be understood as meaning that two of the three free bonds of the carbon atom or of the nitrogen atom are directed toward the adjacent ring members and the third free bond is directed toward the group A, such that in this case the heterocyclic ring is thus bonded to the group A via the group $Q^3$. If the heterocyclic ring is fused to the ring system in the group A via two adjacent atoms of the ring system, a condensed ring system is present. The fusion can take place via the group $Q^3$ and the adjacent carbon atom or via any two desired adjacent carbon atoms. Examples of condensed ring systems of this type are the radicals

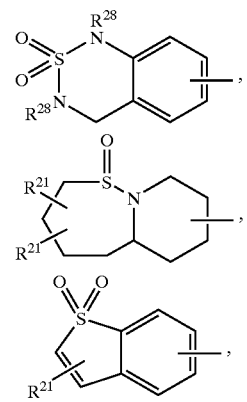

Heterocycles which represent the mono- or bicyclic 5- to 12-membered heterocyclic rings mentioned in the definition of $R^5$ can be aromatic or partially or completely saturated and can be substituted, in particular on a nitrogen atom, by $(C_1-C_7)$-alkyl, for example methyl or ethyl, phenyl or phenyl-$(C_1-C_4)$-alkyl, for example benzyl, and/or on one or more carbon atoms by $(C_1-C_4)$-alkyl, halogen, hydroxyl, $(C_1-C_4)$-alkoxy, for example methoxy, phenyl-$(C_1-C_4)$-alkoxy, for example benzyloxy, or oxo.

Examples of heterocycles on which the group heteroaryl or the mono- or bicyclic 5- to 12-membered heterocyclic ring can be based are pyrrole, furan, thiophene, imidazole, pyrazole, oxazole, isoxazole, thiazole, isothiazole, tetrazole, pyridine, pyrazine, pyrimidine, indole, isoindole, indazole, phthalazine, quinoline, isoquinoline, quinoxaline, quinazoline, cinnoline, β-carboline or benzo-fused, cyclopenta-, cyclohexa- or cyclohepta-fused derivatives of these heterocycles. Nitrogen heterocycles can also be present as N-oxides.

Radicals which can represent heteroaryl or the radical of a mono- or bicyclic 5- to 12-membered heterocyclic ring are, for example, 2- or 3-pyrrolyl, phenylpyrrolyl, for example 4- or 5-phenyl-2-pyrrolyl, 2-furyl, 2-thienyl, 4-imidazolyl, methylimidazolyl, for example 1-methyl-2-, 4- or -5-imidazolyl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5–Chloro or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or, as radicals of partially hydrogenated or completely hydrogenated heterocyclic rings, for example also dihydropyridinyl, pyrrolidinyl, for example 2- or 3-(N-methylpyrrolidinyl), piperazinyl, morpholinyl, thiomorpholinyl, tetrahydrothienyl, benzodioxolanyl.

Heterocyclic radicals representing the radical Het can be unsubstituted on carbon atoms and/or ring nitrogen atoms or monosubstituted or polysubstituted, for example disubstituted, trisubstituted, tetrasubstituted or pentasubstituted, by identical or different substituents.

Carbon atoms can be substituted, for example, by ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, oxo, methylenedioxy, cyano, hydroxycarbonyl, aminocarbonyl, ($C_1$–$C_4$)-alkoxycarbonyl, phenyl, phenoxy, benzyl, benzyloxy, ($R^8O)_2P(O)$, $(R^8O)_2P(O)$—O—, tetrazolyl. Sulfur atoms can be oxidized to the sulfoxide or to the sulfone. Examples of the radical Het are 1-pyrrolyl, 1-imidazolyl, 1-pyrazolyl, 1-tetrazolyl, 1-dihydropyridin-1-yl, tetrahydropyridin-1-yl, 1-pyrrolidinyl, 1-piperidinyl, 1-piperazinyl, 4-substituted 1-piperazinyl, 4-morpholinyl, 4-thiomorpholinyl, 1-oxo-4-thiomorpholinyl, 1,1-dioxothiomorpholinyl, perhydroazepin-1-yl, 2,5-dimethyl-1-pyrrolyl, 2,6-dimethyl-1-piperidinyl, 3,3-dimethyl-4-morpholinyl, 4-isopropyl-2,2,6,6-tetramethyl-1-piperazinyl, 4-acetyl-1-piperazinyl, 4-ethoxycarbonyl-1-piperazinyl.

Halogen is fluorine, chlorine, bromine or iodine, in particular fluorine or chlorine.

Natural or unnatural amino acids can be present in all stereochemical forms, if chiral, for example in the D- or L-form or in the form of a mixture of stereoisomers, for example in the form of a racemate. α-Amino acids and β-amino acids are preferred, particularly preferred are α-amino acids. Examples of suitable amino acids which may be mentioned are (cf. Houben-Weyl, Methoden der organischen Chemie [Methods of organic chemistry], Volume 15/1 and 15/2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hMle, hLeu, hLys, hMet, hPhe, hpro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl)-amino acetic acid.

As customary in peptide chemistry, the radical of an amino acid, imino acid or azaamino acid or of a dipeptide is obtained from the corresponding amino acid, imino acid or azaamino acid or the dipeptide by formally removing a hydrogen atom from the N-terminal amino group or from the imino group or formally removing the hydroxyl group from the carboxylic acid group. Amino acid side chains are understood as meaning side chains of natural or unnatural amino acids. Azaamino acids are natural or unnatural amino acids in which a CH unit is replaced by a nitrogen atom, for example in α-amino acids the central unit

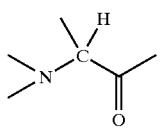 is replaced by 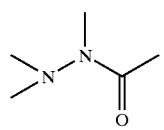.

Suitable radicals of an imino acid are, in particular, radicals of heterocycles from the following group: pyrrolidine-2-carboxylic acid; piperidine-2-carboxylic acid; 1 2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6.9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2–Carboxylic acid; tetrahydrothiazole-4-carboxylic acid; isoxazolidine-3-carboxylic acid; pyrazolidine-3-carboxylic acid, hydroxypyrrolidine-2-carboxylic acid, all of which can optionally be substituted (see following formulae):

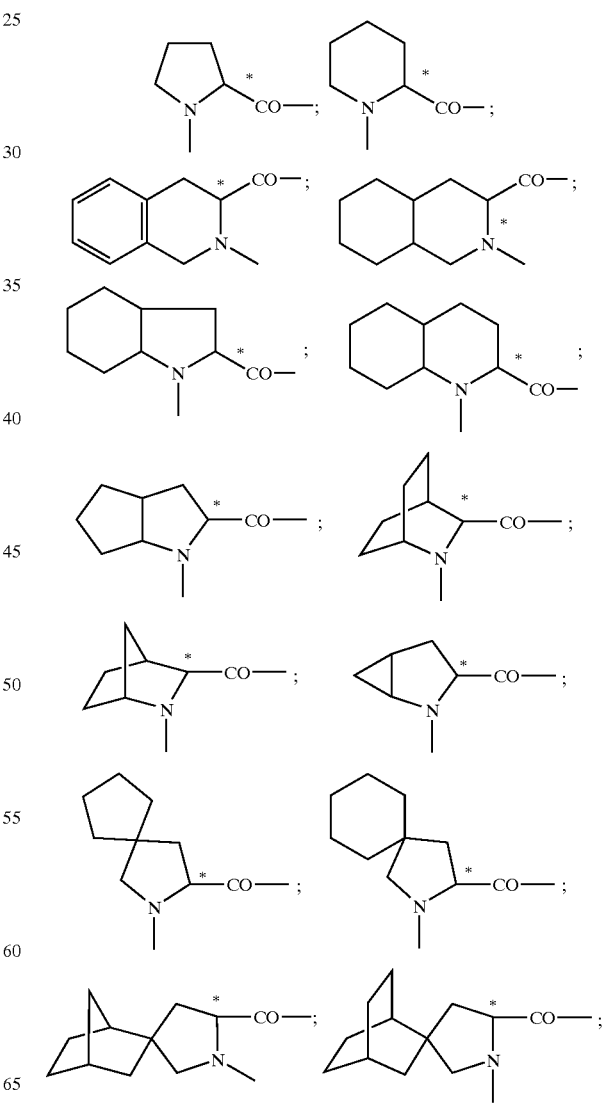

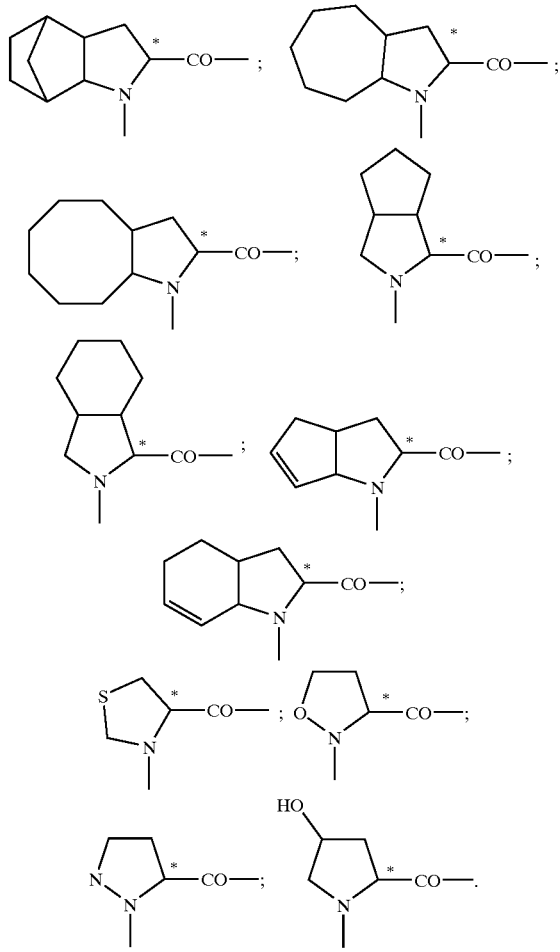

The heterocycles on which the abovementioned radicals are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides can contain natural or unnatural amino acids, imino acids as well as azaamino acids as structural units. The natural or unnatural amino acids, imino acids, azaamino acids and dipeptides can further be present also as esters or amides, such as, for example, as the methyl ester, ethyl ester, isopropyl ester, isobutyl ester, tert-butyl ester, benzyl ester, unsubstituted amide, ethylamide, semicarbazide or ω-amino-($C_2$–$C_8$)-alkylamide.

Functional groups of the amino acids, imino acids and dipeptides can be present in protected form. Suitable protective groups such as, for example, urethane protective groups, carboxyl protective groups and side chain protective groups are described in Hubbuch, Kontakte (Merck) 1979, No. 3, pages 14 to 23, and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt.

Physiologically tolerable salts of the compounds of the formula I are, in particular, pharmaceutically utilizable or nontoxic salts.

Such salts are formed, for example, from compounds of the formula I which contain acidic groups, for example carboxylic acid or sulfonic acid or phosphonic acid groups, with inorganic bases, for example alkali metal or alkaline earth metal compounds or ammonia. The salts of the compounds of the formula I can thus be, for example, sodium, potassium, magnesium, calcium or ammonium salts. Salts of compounds of the formula I with physiologically tolerable organic bases can also be formed, for example with physiologically tolerable organic amines such as triethylamine, ethanolamine or tris(2-hydroxyethyl)amine.

Compounds of the formula I which contain basic groups, for example an amino group or a guanidino group, form salts with inorganic acids, such as, for example, hydrochloric acid, sulfuric acid or phosphoric acid, and with organic carboxylic or sulfonic acids, such as, for example, acetic acid, citric acid, benzoic acid, maleic acid, fumaric acid, tartaric acid, methanesulfonic acid or p-toluenesulfonic acid.

Salts can be obtained from the compounds of the formula I by customary methods known to the person skilled in the art, for example by combination with an organic or inorganic acid or base in a solvent or dispersant, or alternatively from other salts by anion exchange or cation exchange.

The compounds of the formula I can be present in stereoisomeric forms. If the compounds of the formula I contain one or more centers of asymmetry, these can independently of one another have the S configuration or the R configuration. The invention includes all possible stereoisomers, for example enantiomers and diastereomers, and mixtures of two or more stereoisomeric forms, for example mixtures of enantiomers and/or diastereomers, in all ratios. The invention thus relates to enantiomers in enantiomerically pure form, both as levo- and as dextrorotatory antipodes, in the form of racemates and in the form of mixtures of the two enantiomers in all ratios. If cis/trans isomerism is present, the invention relates to both the cis form and the trans form and mixtures of these forms.

The compounds of the formula I according to the invention can moreover contain mobile hydrogen atoms, i.e. can be present in various tautomeric forms. The present invention also relates to all these tautomers. The present invention furthermore includes all solvates of compounds of the formula I, for example hydrates or adducts with alcohols, as well as derivatives of the compounds of the formula I, for example esters, prodrugs and metabolites which act like the compounds of the formula I.

The individual structural elements in the formula I preferably have the following meanings.

W is preferably $R^1$—A—$C(R^{13})$.

A is preferably methylene, ethylene, trimethylene, tetramethylene, pentamethylene, cyclohexylene, phenylene, methylenephenyl, methylenephenylmethyl, phenylenemethyl or phenyleneethyl.

Y is preferably a carbonyl group.

Z is preferably $N(R^0)$.

B is preferably methylene, ethylene, trimethylene, tetramethylene, vinylene, phenylene or substituted methylene or ethylene. B is particularly preferably a bivalent methylene radical or ethylene radical (=1,2-ethylene), where each of these radicals can be unsubstituted or substituted and in particular is substituted. Very particularly preferably, B is a substituted or unsubstituted methylene radical, in particular a substituted methylene radical. If a bivalent methylene radical or ethylene radical (=1,2-ethylene) representing B is substituted, it is preferably substituted by a radical from the group consisting of ($C_1$–$C_8$)-alkyl, ($C_2$–$C_6$)-alkenyl, ($C_2$–$C_6$)-alkynyl, ($C_3$–$C_8$)-cycloalkyl, in particular ($C_5$–$C_6$)- cycloalkyl, $(C_3-C_8)$-cycloalkyl-$(C_1-C_4)$-alkyl, in particular $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl or heteroaryl-$(C_1-C_4)$-alkyl optionally substituted in the heteroaryl radical, and it is particularly preferably substituted by $(C_1-C_8)$-alkyl, i.e. by a straight-chain or branched alkyl radical having 1, 2, 3, 4, 5, 6, 7 or 8 carbon atoms.

D is preferably $C(R^2)(R^3)$.

E is preferably $R^{10}CO$.

R is preferably hydrogen, $(C_1-C_6)$-alkyl or benzyl, in particular hydrogen, methyl or ethyl.

$R^0$ is preferably $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, particularly preferably optionally substituted $(C_6-C_{14})$-aryl, $(C_6-C_{14})$-aryl-$(C_1-C_8)$-alkyl optionally substituted in the aryl radical or heteroaryl-$(C_1-C_8)$-alkyl optionally substituted in the heteroaryl radical, very particularly preferably optionally substituted $(C_6-C_{14})$-aryl-$(C_1-C_4)$-alkyl optionally substituted in the aryl radical or heteroaryl-$(C_1-C_4)$-alkyl optionally substituted in the heteroaryl radical, moreover preferably $(C_6-C_{14})$-aryl-$(C_1-C_4)$-alkyl optionally substituted in the aryl radical. It is specifically preferred if $R^0$ is biphenylylmethyl, naphthylmethyl or benzyl, each of which is unsubstituted or mono- or polysubstituted in the aryl radical.

$R^1$ is preferably one of the radicals —S(O)—N($R^{21}$)—$R^{28}$, —S(O)$_2$—N($R^{21}$)—$R^{28}$, —O—C(O)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—N($R^{21}$)—$R^{28}$, —O—S(O)—N($R^{21}$)—$R^{28}$, —N($R^{29}$)—C(O)—O$R^{22}$, —N($R^{28}$)—C(S)$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —C(S)—$R^{21}$, —C(S)—N($R^{21}$)—$R^{28}$ or cyano or the radical of an optionally substituted, 5- to 14-membered, mono- or polycyclic, saturated or unsaturated heterocyclic ring of the formula

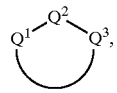

in which $Q^1$ is —C($R^{21}$)$_2$—, =C($R^{21}$)—, —N($R^{28}$)—, —O— or —S—;

$Q^2$ is —S(O)— or —S(O)$_2$—;

$Q^3$ is —C($R^{21}$)$_2$—, C($R^{21}$)—, —N($R^{28}$)—, —O—, —S—, —C($R^{21}$)(—)— or —N(—)—, where the heterocyclic ring can be bonded to the group A via the free bond in the groups —C($R^{21}$)(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A. Particularly preferably, $R^1$ is one of the radicals —O—C(O)—$R^{21}$, —O—C(O)—O$R^{22}$, —O—C(O)—N($R^{21}$)—$R^{28}$, —N($R^{29}$)—C(O)—O$R^{22}$, —N($R^{28}$)—C(O)—N($R^{21}$)—$R^{28}$, —N($R^{28}$)—C(S)—N($R^{21}$)—$R^{28}$ or cyano.

$R^2$ is preferably hydrogen or $(C_1-C_8)$-alkyl.

$R^3$ is preferably $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, pyridyl, $R^{11}NH$, $R^4CO$, $COOR^4$, $CON(CH_3)R^4$, $CONHR^4$, $CSNHR^4$, $COOR^{15}$, $CON(CH_3)R^{15}$ or $CONHR^{15}$, particularly preferably optionally substituted $(C_6-C_{14})$-aryl, $R^{11}NH$, $CON(CH_3)R^4$ or $CONHR^4$.

$R^4$ is preferably $(C_1-C_8)$-alkyl which can optionally be substituted as indicated in the definition of $R^4$, particularly preferably $(C_1-C_8)$-alkyl which is substituted by one or two of the radicals indicated in the definition of $R^4$;

$R^{11}$ is preferably hydrogen, $R^{12a}$, $R^{12a}$—CO, H—CO, $R^{12a}$—O—CO, $R^{12b}$—CO, $R^{12b}$—CS or $R^{12a}$—S(O)$_2$, particularly preferably hydrogen, $R^{12a}$, $R^{12a}$—CO, $R^{12a}$—O—CO, $R^{12b}$—CO, $R^{12b}$—CS or $R^{12a}$—S(O)$_2$, in particular a radical from the group consisting of hydrogen, $(C_1-C_{18})$-alkyl, $R^{12c}CO$, optionally substituted $(C_6-C_{14})$-aryl-S(O)$_2$, $(C_1-C_{18})$-alkyl-S(O)$_2$, $(C_6-C_{14})$-aryl-$(C_1-C_8)$-alkyl optionally substituted in the aryl radical, $R^9NHS(O)_2$ and $R^{15}$, where $R^c$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy, which can also be substituted in the aryl radical, optionally substituted $(C_6-C_{14})$-aryloxy, amino or mono- or di-(($C_1-C_{18}$)-alkyl)-amino, the radical $R^{15}$ or the radical $R^{15}$—O—. Very particularly preferably, $R^{11}$ is $R^{12a}$, $R^{12a}$—CO, $R^{12a}$—O—CO, $R^{12b}$—CO, $R^{12b}$—CS or $R^{12a}$—S(O)$_2$, moreover particularly preferably for $R^{12a}$, $R^{12a}$—CO, $R^{12a}$—O—CO, $R^{12b}$—CO or $R^{12a}$—S(O)$_2$.

$R^{12a}$ is preferably $(C_1-C_{10})$-alkyl, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical or the radical $R^{15}$.

$R^{12b}$ is preferably $R^{12a}$—NH.

$R^{13}$ is preferably hydrogen, $(C_1-C_6)$-alkyl, $(C_6-C_{14})$-aryl-$(C_1-C_8)$-alkyl optionally substituted in the aryl radical or $(C_3-C_8)$-cycloalkyl, particularly preferably hydrogen or in particular $(C_1-C_6)$-alkyl, $(C_3-C_8)$-cycloalkyl or benzyl, where a very particularly preferred alkyl radical representing $R^{13}$ is the methyl radical.

$R^{15}$ is preferably $R^{16}$—$(C_1-C_3)$-alkyl or $R^{16}$, particularly preferably $R^{16}$—$(C_1)$-alkyl or $R^{16}$. Moreover, when $R^3$ is $COOR^{15}$, $R^{15}$ is preferably the exo-2-norbornyl radical, the endo-2-norbornyl radical or the bicyclo[3.2.1]octyl radical, and when $R^3$ is $CONHR^{15}$, $R^{15}$ is the exo-2-norbornyl radical, the endo-2-norbornyl radical, the 3-noradamantyl radical and in particular the 1-adamantyl radical, the 2-adamantyl radical, the 1-adamantylmethyl radical or the 2-adamantylmethyl radical.

$R^{16}$ is preferably a 7- to 12-membered bridged bicyclic or tricyclic radical, which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo.

Het is preferably the radical of a 5- to 10-membered, saturated monocyclic or polycyclic heterocycle bonded via a nitrogen atom, which can contain one or two identical or different additional ring heteroatoms from the group consisting of oxygen, nitrogen and sulfur and can optionally be substituted on carbon atoms and on ring nitrogen atoms, where there can be identical or different radicals $R^h$, $R^hCO$ or $R^hO$—CO as substituents on additional ring nitrogen atoms. Particularly preferably, Het is a heterocycle of the type which contains no additional ring heteroatom or which contains one additional ring heteroatom from the group consisting of nitrogen, oxygen and sulfur, very particularly preferably Het is the radical of a 5-, 6- or 7-membered, saturated monocyclic heterocycle bonded via a nitrogen atom, which contains no additional ring heteroatom or which contains one additional ring heteroatom from the group consisting of nitrogen, oxygen and sulfur, where in these cases too the radical Het can be unsubstituted or can be substituted on carbon atoms and/or on additional ring nitrogen atoms.

b, c and d preferably independently of one another are 1.

e, g and h preferably independently of one another are the numbers 0, 1, 2 or 3.

Preferred compounds of the formula I are those in which, simultaneously

W is $R^1$—A—$C(R^{13})$ or $R^1$—A—CH=C;

Y is a carbonyl, thiocarbonyl or methylene group;

Z is $N(R^0)$, oxygen, sulfur or a methylene group;

A is a bivalent radical from the group consisting of $(C_1-C_6)$-alkylene, $(C_3-C_{12})$-cycloalkylene, $(C_1-C_6)$-alkylene-$(C_3-C_{12})$-cycloalkyl, phenylene, phenylene-$(C_1-C_6)$-alkyl, $(C_1-C_6)$-alkylenephenyl, $(C_1-C_6)$-alkylenephenyl-$(C_1-C_6)$-alkyl, phenylene-$(C_2-C_6)$-alkenyl or a bivalent radical of a 5- or 6-membered saturated or unsaturated ring which can contain 1 or 2 nitrogen atoms and can be mono- or disubstituted by $(C_1-C_6)$-alkyl or doubly bonded oxygen or sulfur, or is a direct bond;

B is a bivalent radical from the group consisting of $(C_1-C_6)$-alkylene, $(C_2-C_6)$-alkenylene, phenylene, phenylene-$(C_1-C_3)$-alkyl, $(C_1-C_3)$-alkylene-phenyl;

D is $C(R^2)(R^3)$, $N(R^3)$ or CH=$C(R^3)$;

E is tetrazolyl, $(R^8O)_2P(O)$, $HOS(O)_2$, $R^9NHS(O)_2$ or $R^{10}CO$;

R and $R^0$ independently of one another are hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where alkyl radicals can be mono- or polysubstituted by fluorine;

$R^1$ is one of the radicals —S—$R^{21}$, —S—S—$R^{21}$, —S(O)—$R^{22}$, —S(O)$_2$—$R^{22}$, —S—O$R^{21}$, —S(O)—O$R^{21}$, —S(O)$_2$—O$R^{21}$, —S—N($R^{21}$)—$R^{28}$, —S(O)—N($R^{21}$)—$R^{28}$, —S(O)$_2$—N($R^{21}$)—$R^{28}$, —S—C(O)—$R^{21}$, —S—C(O)—O$R^{22}$, —S—C(S)—S$R^{22}$, —S—C(O)—N($R^{21}$)—$R^{28}$, —S—C(S)—N($R^{21}$)—$R^{28}$, —O—C(O)—$R^{21}$, —O—C(S)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—O$R^{21}$, —O—S(O)—O$R^{21}$, —O—S(O)$_2$—N($R^{21}$)—$R^{28}$, —O—S(O)—N($R^{21}$)—$R^{28}$, —O—S(O)$_2$—$R^{22}$, —O—S(O)—$R^{22}$, —O—P(O)(O$R^{21}$)$_2$, —O—P(O)(O$R^{21}$)—N($R^{21}$)—$R^{28}$, —O—P(O)(N($R^{21}$)—$R^{28}$)$_2$, —N($R^{29}$)—C(O)—O$R^{22}$, —N($R^{28}$)—C(O)—S$R^{22}$, —N($R^{28}$)—C(S)—O$R^{22}$, —N($R^{28}$)—C(S)—S$R^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —N($R^{28}$)—P(O)(O$R^{21}$)$_2$, —N($R^{28}$)—P(O)(O$R^{21}$)—N($R^{21}$)—$R^{28}$, —N($R^{28}$)—P(O)(N($R^{21}$)—$R^{28}$)$_2$, —N($R^{28}$)—P(O)($R^{22}$)—O$R^{21}$, —N($R^{28}$)—P(O)($R^{22}$)—N($R^{21}$)—$R^{28}$, —N($R^{28}$)—P(O)($R_{22}$)$_2$, —P(O)(O$R^{21}$)$_2$, —P(O)(O$R^{21}$)—N($R^{21}$)—$R^{28}$, —P(O)(N($R^{21}$)—$R^{28}$)$_2$, —P(O)($R^{22}$)—O$R^{21}$, —P(O)($R^{22}$)—N($R^{21}$)—$R^{28}$, —P(O)($R^{22}$)$_2$, —C(S)—$R^{21}$, —C(S)—S$R^{21}$, —C(S)—N($R^{21}$)—$R^{28}$, cyano, halogen, nitro or methylenedioxy or the radical of an optionally substituted, 5- to 14-membered, mono- or polycyclic, saturated or unsaturated heterocyclic ring of the formula

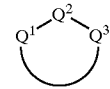

in which $Q^1$ is —$C(R^{21})_2$—, =$C(R^{21})$—, —$N(R^{28})$—, —O— or —S—;

$Q^2$ is —S(O)— or —S(O)$_2$—;

$Q^3$ is —$C(R^{21})_2$—, =$C(R^{21})$—, —$N(R^{28})$—, —O—, —S—, —$C(R^{21})$(—)— or —N(—)—, where the heterocyclic ring can be bonded to the group A via the free bond in the groups —$C(R^{21})$(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}NH$, $R^4CO$, $COOR^4$, $CON(CH_3)R^4$, $CONHR^4$, $CSNHR^4$, $COOR^{15}$, $CON(CH_3)R^{15}$ or $CONHR^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-$((C_1-C_{18})$-alkyl)aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, $HOS(O)_2$—$(C_1-C_3)$-alkyl, $R^9NHS(O)_2$—$(C_1-C_3)$-alkyl, $(R^8O)_2P(O)$—$(C_1-C_3)$-alkyl, tetrazolyl-$(C_1-C_3)$-alkyl, halogen, nitro, trifluoromethyl or the radical $R^5$;

$R^5$ is optionally substituted $(C_6-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino or trifluoromethyl;

$R^6$ is $R^7R^8N$, $R^7O$ or $R^7S$ or an amino acid side chain, a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—CH$_2$—, and their esters and amides, where hydrogen or hydroxymethyl can optionally stand in place of free functional groups and/or where free functional groups can be protected by protective groups customary in peptide chemistry;

$R^7$ is hydrogen, ($C_1$–$C_{18}$)-alkyl, ($C_6$–$C_{14}$)-aryl-($C_1$–$C_8$)-alkyl, ($C_1$–$C_{18}$)-alkylcarbonyl, ($C_1$–$C_{18}$)-alkoxycarbonyl, ($C_6$–$C_{14}$)-arylcarbonyl, ($C_6$–$C_{14}$)-aryl-($C_1$–$C_8$)-alkylcarbonyl or ($C_6$–$C_{14}$)-aryl-($C_1$–$C_{18}$)-alkyloxycarbonyl, where the alkyl groups can optionally be substituted by an amino group and/or where the aryl radicals can be mono- or polysubstituted, preferably monosubstituted, by identical or different radicals from the group consisting of ($C_1$–$C_8$)-alkyl, ($C_1$–$C_8$)-alkoxy, halogen, nitro, amino and trifluoromethyl, or is a natural or unnatural amino acid, imino acid, optionally N—($C_1$–$C_8$)-alkylated or N—(($C_6$–$C_{14}$)-aryl-($C_1$–$C_8$)-alkylated) azaamino acid or a dipeptide radical which can also be substituted in the aryl radical and/or in which the peptide bond can be reduced to —NH—CH$_2$—;

$R^8$ is hydrogen, ($C_1$–$C_{18}$)-alkyl, optionally substituted ($C_6$–$C_{14}$)-aryl or ($C_6$–$C_{14}$)-aryl-($C_1$–$C_8$)-alkyl which can also be substituted in the aryl radical;

$R^9$ is hydrogen, aminocarbonyl, ($C_1$–$C_{18}$)-alkylaminocarbonyl, ($C_3$–$C_8$)-cycloalkylaminocarbonyl, optionally substituted ($C_6$–$C_{14}$)-arylaminocarbonyl, ($C_1$–$C_{18}$)-alkyl, optionally substituted ($C_6$–$C_{14}$)-aryl or ($C_3$–$C_8$)-cycloalkyl;

$R^{10}$ is hydroxyl, ($C_1$–$C_{18}$)-alkoxy, ($C_6$–$C_{14}$)-aryl-($C_1$–$C_8$)-alkoxy which can also be substituted in the aryl radical, optionally substituted ($C_6$–$C_{14}$)-aryloxy, amino or mono- or di-(($C_1$–$C_{18}$)-alkyl)amino;

$R^{11}$ is hydrogen, ($C_1$–$C_{18}$)-alkyl, $R^{12}$CO, optionally substituted ($C_6$–$C_{14}$)-aryl-S(O)$_2$, ($C_1$–$C_{18}$)-alkyl-S(O)$_2$, ($C_6$–$C_{14}$)-aryl-($C_1$–$C_8$)-alkyl optionally substituted in the aryl radical, $R^9$NHS(O)$_2$ or the radical $R^{15}$;

$R^{12}$ is hydrogen, ($C_1$–$C_{18}$)-alkyl, ($C_2$–$C_8$)-alkenyl, ($C_2$–$C_8$)-alkynyl, optionally substituted ($C_6$–$C_{14}$)-aryl, ($C_1$–$C_{18}$)-alkoxy, ($C_6$–$C_{14}$)-aryl-($C_1$–$C_8$)-alkoxy which can also be substituted in the aryl radical, optionally substituted ($C_6$–$C_{14}$)-aryloxy, amino or mono- or di-(($C_1$–$C_{18}$)-alkyl) amino, the radical $R^{15}$ or the radical $R^{15}$—O—;

$R^{13}$ is hydrogen, ($C_1$–$C_6$)-alkyl, ($C_6$–$C_{14}$)-aryl-($C_1$–$C_8$)-alkyl optionally substituted in the aryl radical or ($C_3$–$C_8$)-cycloalkyl;

$R^{15}$ is $R^{16}$—($C_1$–$C_6$)-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of ($C_1$–$C_4$)-alkyl and oxo;

$R^{21}$ is hydrogen, ($C_1$–$C_8$)-alkyl, hydroxy-($C_1$–$C_8$)-alkyl, ($C_2$–$C_8$)-alkenyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can also be monosubstituted or polysubstituted by fluorine and the radicals $R^{21}$ can be identical or different if they occur two or more times;

$R^{22}$ is ($C_1$–$C_8$)-alkyl, hydroxy-($C_1$–$C_8$)-alkyl, ($C_2$–$C_8$)-alkenyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be monosubstituted or polysubstituted by fluorine and the radicals $R^{22}$ can be identical or different if they occur two or more times;

$R^{28}$ is one of the radicals $R^{21}$—, $R^{21}$N($R^{21}$)—, $R^{21}$C(O)—, $R^{22}$O—C(O)—, $R^{21}$N($R^{21}$)—C(O)— or $R^{21}$N($R^{21}$)—C(=N($R^{21}$))—;

$R^{29}$ is one of the radicals $R^{22}$—, $R^{21}$N($R^{21}$)—, $R^{21}$C(O)—, $R^{22}$O—C(O)—, $R^{21}$N($R^{21}$)—C(O)— or $R^{21}$N($R^{21}$)—C(=N($R^{21}$))—;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and their physiologically tolerable salts, where, if simultaneously W is 4-cyanophenyl-C($R^{13}$), Y is a carbonyl group, Z is NR$^{0a}$, B is an unsubstituted methylene group, R is R$^a$, b, c and d are 1 and e, f and g are 0, then D cannot be C($R^{2a}$)($R^{3a}$), where $R^{0a}$, $R^a$ and $R^{2a}$ independently of one another are hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical or ($C_3$–$C_8$)-cycloalkyl and $R^{3a}$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, ($C_3$–$C_8$)-cycloalkyl or 2-, 3- or 4-pyridyl.

Particularly preferred compounds of the formula I are those in which simultaneously W is $R^1$—A—CH=C and therein A is a phenylene radical or a methylenephenyl radical, or W is $R^1$—A—C($R^{13}$) and therein A is a bivalent radical from the group consisting of methylene, ethylene, trimethylene, tetramethylene, pentamethylene, cyclohexylene, phenylene, phenylenemethyl, methylenephenyl, methylenephenylmethyl;

B is a bivalent radical from the group consisting of methylene, ethylene, trimethylene, tetramethylene, vinylene, phenylene, or substitued methylene or ethylene;

E is $R^{10}$CO;

R is hydrogen, ($C_1$–$C_6$)-alkyl or benzyl;

$R^0$ is ($C_1$–$C_8$)-alkyl, ($C_3$–$C_8$)-cycloalkyl, optionally substituted ($C_6$–$C_{14}$)-aryl or ($C_6$–$C_{14}$)-aryl-($C_1$–$C_8$)-alkyl optionally substituted in the aryl radical;

$R^1$ is preferably one of the radicals —S(O)—N($R^{21}$)—$R^{28}$, —S(O)$_2$—N($R^{21}$)—$R^{28}$, —O—C(O)—$R^{21}$, —O—C(O)—OR$^{22}$, —O—C(O)—N($R^{21}$)—$R^{28}$, —O—C(S)—N($R^{21}$)—$R^{28}$, —O—S(O)$_2$—N($R^{21}$)—$R^{28}$, —O—S(O)—N($R^{21}$)—$R^{28}$, —N($R^{29}$)—C(O)—OR$^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—OR$^{21}$, —N($R^{28}$)—S(O)—OR$^{21}$, —N($R^{28}$)—S(O)$_2$—N($R^{21}$)—$R^{28}$, —N($R^{28}$)—S(O)—N($R^{21}$)—$R^{28}$, —C(S)—$R^{21}$, —C(S)—N($R^{21}$)—$R^{28}$ or cyano or the radical of an optionally substituted, 5- to 14-membered, mono- or polycyclic, saturated or unsaturated heterocyclic ring of the formula

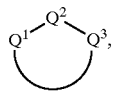

in which
Q$^1$ is —C(R$^{21}$)$_2$—, =C(R$^{21}$)—, —N(R$^{28}$)—, —O— or —S—;
Q$^2$ is —S(O)— or —S(O)$_2$—;
Q$^3$ is —C(R$^{21}$)$_2$—, =C(R$^{21}$)—, —N(R$^{28}$)—, —O—, —S—, —C(R$^{21}$) (—)— or —N(—)—,
where the heterocyclic ring can be bonded to the group A via the free bond in the groups —C(R$^{21}$)(—)— or —N(—)— representing Q$^3$ or via any other desired ring carbon atom and where, if the heterocyclic ring is bonded to a ring system contained in the group A, the heterocyclic ring can also be fused via two adjacent atoms to the ring system in the group A;
R$^2$ is hydrogen or (C$_1$–C$_8$)-alkyl;
R$^3$ is (C$_1$–C$_8$)-alkyl, optionally substituted (C$_6$–C$_{14}$)-aryl, (C$_6$–C$_{14}$)-aryl-(C$_1$–C$_8$)-alkyl, (C$_3$–C$_8$)-cycloalkyl, (C$_2$–C$_8$)-alkenyl, (C$_2$–C$_8$)-alkynyl, pyridyl, R$^{11}$NH, R$^4$CO, COOR$^4$, CONHR$^4$, CSNHR$^4$, COOR$^{15}$ and CONHR$^{15}$;
and e, g and h independently of one another are the numbers 0, 1, 2 or 3;
in all their stereoisomeric forms and mixtures thereof in any ratio, and their physiologically tolerable salts.

Very particularly preferred compounds of the formula I are those in which W is R$^1$—A—C(R$^{13}$) and R$^{13}$ is (C$_1$–C$_6$)-alkyl, (C$_6$–C$_{14}$)-aryl-(C$_1$–C$_8$)-alkyl optionally substituted in the aryl radical or (C$_3$–C$_8$)-cycloalkyl;
in all their stereoisomeric forms and mixtures thereof in any ratio, and their physiologically tolerable salts.

A series of specifically preferred compounds of the formula I are those in which R$^3$ is optionally substituted (C$_6$–C$_{14}$)-aryl, COOR$^4$, R$^{11}$NH or CONHR$^{14}$, where —NHR$^{14}$ is the radical of an α-amino acid, its ω-amino-(C$_2$–C$_8$)-alkylamide, its (C$_1$–C$_8$)-alkyl ester, its (C$_6$–C$_{14}$)-aryl-(C$_1$–C$_4$)-alkyl ester, or its derivative in which the carboxylic acid group is converted into the group Het-CO, in all their stereoisomeric forms and mixtures thereof in any ratio, and their physiologically tolerable salts. The radical of an α-amino acid —NHR$^{14}$ is formally obtained by abstraction of a hydrogen atom from the amino group of the amino acid. It is specifically preferred in this series if R$^3$ is CONHR$^4$, where —NHR$^4$ is the radical of the α-amino acids valine, lysine, phenylglycine, phenylalanine or tryptophan or their (C$_1$–C$_8$)-alkyl esters, (C$_6$–C$_{14}$)-aryl-(C$_1$–C$_4$)-alkyl esters or Het-CO derivative.

Moreover preferred compounds of the formula I in this series are those in which simultaneously
W is R$^1$—A—C(R$^{13}$);
Y is a carbonyl group;
Z is N(R$^0$);
A is ethylene, trimethylene, tetramethylene, pentamethylene, cyclohexylene, phenylene, phenylenemethyl, methylenephenyl or methylenephenylmethyl;
B is an unsubstituted or substituted methylene radical;
D is C(R$^2$)(R$^3$);
E is R$^{10}$CO;
R is hydrogen or (C$_1$–C$_4$)-alkyl, in particular hydrogen, methyl or ethyl;
R$^0$ is (C$_1$–C$_8$)-alkyl, (C$_3$–C$_8$)-cycloalkyl, optionally substituted (C$_6$–C$_{14}$)-aryl or (C$_6$–C$_{14}$)-aryl-(C$_1$–C$_8$)-alkyl optionally substituted in the aryl radical;

R$^1$ is one of the radicals —O—C(O)R$^{21}$, —O—C(O)—OR$^{22}$, —O—C(O)—N(R$^{21}$)—R$^{28}$, —N(R$^{29}$)—C(O)—OR$^{12}$, —N(R$^{28}$)—C(O)—N(R$^{21}$)—R$^{28}$, —N(R$^{28}$)—C(S)—N(R$^{21}$)—R$^{28}$ or cyano;
R$^2$ is hydrogen;
R$^3$ is the radical CONHR$^4$;
R$^4$ is methyl which is substituted by hydroxycarbonyl and a radical from the group consisting of (C$_1$–C$_4$)-alkyl, phenyl and benzyl, or is methyl which is substituted by (C$_1$–C$_8$)-alkoxycarbonyl, preferably (C$_1$–C$_4$)-alkoxycarbonyl, and a radical from the group consisting of (C$_1$–C$_4$)-alkyl, phenyl and benzyl, or is methyl which is substituted by Het-CO and a radical from the group consisting of (C$_1$–C$_4$)-alkyl, phenyl and benzyl;
R$^{10}$ is hydroxyl or (C$_1$–C$_8$)-alkoxy, preferably (C$_1$–C$_4$)-alkoxy;
R$^{13}$ is (C$_1$–C$_6$)-alkyl, (C$_3$–C$_7$)-cycloalkyl or benzyl, in particular methyl;
b, c and d are 1 and e, f and g are 0;
h is 1 or 2, preferably 1;
in all their stereoisomeric forms and mixtures thereof in any ratio, and their physiologically tolerable salts.

If —NHR$^4$ is a (C$_1$–C$_8$)-alkyl ester of an α-amino acid or R$^4$ contains an alkoxycarbonyl radical, the methyl, ethyl, isopropyl, isobutyl or tert-butyl ester is preferred, if —NHR$^4$ is a (C$_6$–C$_{14}$)-aryl-(C$_1$–C$_4$)-alkyl ester of an α-amino acid, the benzyl ester is preferred.

A further series of specifically preferred compounds of the formula I are those compounds in which simultaneously
W is R$^1$-A-CH=C and therein A is a phenylene radical or a methylenephenyl radical, or W is R$^1$-A-C(R$^{13}$) and therein A is a bivalent radical from the group consisting of methylene, ethylene, trimethylene, tetramethylene, pentamethylene, cyclohexylene, phenylene, phenylenemethyl, methylenephenyl, methylenephenylmethyl;
B is a bivalent radical from the group consisting of methylene, ethylene, trimethylene, tetramethylene, vinylene, phenylene or substituted methylene or ethylene;
E is R$^{10}$CO;
R is hydrogen or (C$_1$–C$_6$)-alkyl;
R$^0$ is (C$_1$–C$_8$)-alkyl, (C$_3$–C$_8$)-cycloalkyl, optionally substituted (C$_6$–C$_{14}$)-aryl or (C$_6$–C$_{14}$)-aryl-(C$_1$–C$_8$)-alkyl optionally substituted in the aryl radical;
R$^1$ is preferably one of the radicals —S(O)—N(R$^{21}$)—R$^{28}$, —S(O)$_2$—N(R$^{21}$)—R$^{28}$, —O—C(O)—R$^{21}$, —O—C(O)—OR$^{22}$, —O—C(O)—N(R$^{21}$)—R$^{28}$, —O—C(S)—N(R$^{21}$)—R$^{28}$, —O—S(O)$_2$—N(R$^{21}$)—R$^{28}$, —O—S(O)—N(R$^{21}$)—R$^{28}$, —N(R$^{29}$)—C(O)—OR$^{22}$, —N(R$^{28}$)—C(S)—R$^{21}$, —N(R$^{28}$)—C(O)—N(R$^{21}$)—R$^{28}$, —N(R$^{28}$)—C(S)—N(R$^{21}$)—R$^{28}$, —N(R$^{28}$)—S(O)$_2$—R$^{22}$, —N(R$^{28}$)—S(O)—R$^{22}$, —N(R$^{28}$)—S(O)$_2$—OR$^{21}$, —N(R$^{28}$)—S(O)—OR$^{21}$, —N(R$^{28}$)—S(O)$_2$—N(R$^{21}$)—R$^{28}$, —N(R$^{28}$)—S(O)—N(R$^{21}$)—R$^{28}$, —C(S)—R$^{21}$, —C(S)—N(R$^{21}$)—R$^{28}$ or cyano or the radical of an optionally substituted, 5- to 14-membered, mono- or polycyclic, saturated or unsaturated heterocyclic ring of the formula

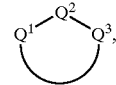

in which
Q$^1$ is —C(R$^{21}$)$_2$—, =C(R$^{21}$)—, —N(R$^{28}$)—, —O— or —S—;
Q$^2$ is —S(O)— or —S(O)$_2$—;

$Q^3$ is —$C(R^{21})_2$—, =$C(R^{21})$—, —$N(R^{28})$—, —O—, —S—, —$C(R^{21})$(—)— or —N(—)—, where the heterocyclic ring can be bonded to the group A via the free bond in the groups —$C(R^{21})$(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen or $(C_1–C_8)$-alkyl;

$R^3$ is CONHR$^{15}$ or CONHR$^4$ where $R^4$ herein is a $(C_1–C_8)$-alkyl radical which is unsubstituted or substituted by one or more $(C_6–C_{14})$-aryl radicals;

$R^{15}$ is $R^{16}$—$(C_1–C_6)$-alkyl or $R^{16}$, where $R^{16}$ is a 7- to 12-membered bridged bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1–C_4)$-alkyl and oxo, and in particular $R^{15}$ is an adamantyl radical or an adamantylmethyl radical;

and e, g and h independently of one another are the numbers 0, 1, 2 or 3 and b, c and d are 1;

in all their stereoisomeric forms and mixtures thereof in any ratio, and their physiologically tolerable salts.

Moreover preferred compounds of the formula I in this series are those in which simultaneously W is $R^1$-A-$C(R^{13})$;
Y is a carbonyl group;
Z is $N(R^0)$;
A is ethylene, trimethylene, tetramethylene, pentamethylene, cyclohexylene, phenylene, phenylenemethyl, methylenephenyl or methylenephenylmethyl;
B is an unsubstituted or substituted methylene radical;
D is $C(R^2)(R^3)$;
E is $R^{10}$CO;
R is hydrogen or $(C_1–C_4)$-alkyl, in particular hydrogen, methyl or ethyl;
$R^0$ is $(C_1–C_8)$-alkyl, $(C_3–C_8)$-cycloalkyl, optionally substituted $(C_6–C_{14})$-aryl or $(C_6–C_{14})$-aryl-$(C_1–C_8)$-alkyl optionally substituted in the aryl radical;
$R^1$ is one of the radicals —O—C(O)—$R^{21}$, —O—C(O)—OR$^{22}$, —O—C(O)—N(R$^{21}$)—R$^{28}$, —N(R$^{29}$)—C(O)—OR$^{22}$, —N(R$^{28}$)—C(O)—N(R$^{21}$)—R$^{28}$, —N(R$^{28}$)—C(S)—N(R$^{21}$)—R$^{28}$ or cyano;
$R^2$ is hydrogen;
$R^3$ is CONHR$^{15}$ or CONHR$^4$ where $R^4$ herein is a $(C_1–C_6)$-alkyl radical which is unsubstituted or substituted by one or more $(C_6–C_{10})$-aryl radicals;
$R^{10}$ is hydroxyl or $(C_1–C_8)$-alkoxy, preferably $(C_1–C_4)$-alkoxy;
$R^{13}$ is $(C_1–C_6)$-alkyl, $(C_3–C_7)$-cycloalkyl or benzyl, in particular methyl;
$R^{15}$ is an adamantyl radical or an adamantylmethyl radical;
b, c and d are 1 and e, f and g are 0;
h is 1 or 2, preferably 1;
in all their stereoisomeric forms and mixtures thereof in any ratio, and their physiologically tolerable salts.

Furthermore, a series of specifically preferred compounds of the formula I are those in which simultaneously W is $R^1$-A-$C(R^{13})$;
Y is a carbonyl group;
Z is $N(R^0)$;
A is ethylene, trimethylene, tetramethylene, pentamethylene, cyclohexylene, phenylene, phenylenemethyl, methylenephenyl, methylenephenylmethyl;
B is an unsubstituted or substituted methylene radical or ethylene radical;
D is $C(R^2)(R^3)$;
E is $R^{10}$CO;
R is hydrogen or $(C_1–C_4)$-alkyl, in particular hydrogen, methyl or ethyl;
$R^0$ is $(C_1–C_8)$-alkyl, $(C_3–C_8)$-cycloalkyl, optionally substituted $(C_6–C_{14})$-aryl or $(C_6–C_{14})$-aryl-$(C_1–C_8)$-alkyl which is optionally substituted in the aryl radical;
$R^1$ is preferably one of the radicals —S(O)—N(R$^{21}$)—R$^{28}$, —S(O)$_2$—N(R$^{21}$)—R$^{28}$, —O—C(O)—R$^{21}$, —O—C(O)—OR$^{22}$, —O—C(O)—N(R$^{21}$)—R$^{28}$, —O—C(S)—N(R$^{21}$)—R$^{28}$, —O—S(O)$_2$—N(R$^{21}$)—R$^{28}$, —O—S(O)—N(R$^{21}$)—R$^{28}$, —N(R$^{29}$)—C(O)—OR$^{22}$, —N(R$^{28}$)—C(S)—R$^{21}$, —N(R$^{28}$)—C(O)—N(R$^{21}$)—R$^{28}$, —N(R$^{28}$)—C(S)—N(R$^{21}$)—R$^{28}$, —N(R$^{28}$)—S(O)$_2$—R$^{22}$, —N(R$^{28}$)—S(O)—R$^{22}$, —N(R$^{28}$)—S(O)$_2$—OR$^{21}$, —N(R$^{28}$)—S(O)—OR$^{21}$, —N(R$^{28}$)—S(O)$_2$—N(R$^{21}$)—R$^{28}$, —N(R$^{28}$)—S(O)—N(R$^{21}$)—R$^{28}$, —C(S)—R$^{21}$, —C(S)—N(R$^{21}$)—R$^{28}$ or cyano or the radical of an optionally substituted, 5- to 14-membered, mono- or polycyclic, saturated or unsaturated heterocyclic ring of the formula

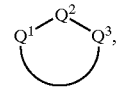

in which
$Q^1$ is —$C(R^{21})_2$—, =$C(R^{21})$—, —$N(R^{28})$—, —O— or —S—;
$Q^2$ is —S(O)— or —S(O)$_2$—;
$Q^3$ is —$C(R^{21})_2$—, =$C(R^{21})$—, —$N(R^{28})$—, —O—, —S—, —$C(R^{21})$(—)— or —N(—)—, where the heterocyclic ring can be bonded to the group A via the free bond in the groups —$C(R^{21})$(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen;
$R^3$ is an unsubstituted phenyl radical or naphthyl radical, a phenyl radical or naphthyl radical substituted by one, two or three identical or different radicals from the group consisting of $(C_1–C_4)$-alkyl, $(C_1–C_4)$-alkoxy, hydroxyl, halogen, trifluoromethyl, nitro, methylenedioxy, ethylenedioxy, hydroxycarbonyl, $(C_1–C_4)$-alkoxycarbonyl, aminocarbonyl, cyano, phenyl, phenoxy and benzyloxy, a pyridyl radical, a $(C_1–C_4)$-alkyl radical, a $(C_2–C_4)$-alkenyl radical, a $(C_2–C_4)$-alkynyl radical or a $(C_5–C_6)$-cycloalkyl radical, and in particular $R^3$ is an unsubstituted or substituted phenyl radical or naphthyl radical;
$R^{10}$ is hydroxyl or $(C_1–C_8)$-alkoxy, in particular $(C_1–C_4)$-alkoxy, and preferably $R^{10}$ is a radical from the group consisting of hydroxyl, methoxy, ethoxy, propoxy and isopropoxy;
$R^{13}$ is $(C_1–C_6)$-alkyl, $(C_3–C_7)$-cycloalkyl or benzyl, in particular methyl;
b, c and d are 1 and e, f and g are 0;
h is 1 or 2, preferably 1;
in all their stereoisomeric forms and mixtures thereof in any ratio, and their physiologically tolerable salts.

Finally, a series of specifically preferred compounds of the formula I are those compounds in which simultaneously W is $R^1$-A-$C(R^{13})$;
Y is a carbonyl group;
Z is $N(R^0)$;
A is ethylene, trimethylene, tetramethylene, pentamethylene, cyclohexylene, phenylene, phenylenemethyl, methylenephenyl, methylenephenylmethyl;

B is an unsubstituted or substituted methylene radical or ethylene radical;

D is $C(R^2)(R^3)$;

E is $R^{10}CO$;

R is hydrogen or $(C_1-C_4)$-alkyl, in particular hydrogen, methyl or ethyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is preferably one of the radicals —S(O)—N($R^{21}$)—$R^{28}$, —S(O)$_2$—N($R^{21}$)—$R^{28}$, —O—C(O)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—N($R^{21}$)—$R^{28}$, —O—S(O)—N($R^{21}$)—$R^{28}$, —N($R^{29}$)—C(O)—O$R^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —C(S)—$R^{21}$, —C(S)—N($R^{21}$)—$R^{28}$ or cyano or the radical of an optionally substituted, 5- to 14-membered, mono- or polycyclic, saturated or unsaturated heterocyclic ring of the formula

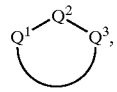

in which $Q^1$ is —C($R^{21}$)$_2$—, =C($R^{21}$)—, —N($R^{28}$)—, —O— or —S—;

$Q^2$ is —S(O)— or —S(O)$_2$—;

$Q^3$ is —C($R^{21}$)$_2$—, =C($R^{21}$)—, —N($R^{28}$)—, —O—, —S—, —C($R^{21}$)(—)— or —N(—)—, where the heterocyclic ring can be bonded to the group A via the free bond in the groups —C($R^{21}$)(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen;

$R^3$ is $R^{11}$NH;

$R^{10}$ is hydroxyl or $(C_1-C_8)$-alkoxy, in particular $(C_1-C_4)$-alkoxy, and preferably $R^{10}$ is a radical from the group consisting of hydroxyl, methoxy, ethoxy, propoxy and isopropoxy;

$R^{13}$ is $(C_1-C_6)$-alkyl, $(C_3-C_7)$-cycloalkyl or benzyl, in particular methyl;

b, c, d and e are 1 and f and g are 0;

h is 0;

in all their stereoisomeric forms and mixtures thereof in any ratio, and their physiologically tolerable salts.

In this series, moreover preferred compounds of the formula I are those in which $R^{11}$ is $R^{12a}$, $R^{12a}$—CO, $R^{12a}$—O—CO, $R^{12b}$—CO, $R^{12b}$—CS or $R^{12a}$—S(O)$_2$, in particular $R^{12a}$, $R^{12a}$—CO, $R^{12a}$—O—CO, $R^{12b}$—CO or $R^{12a}$—S(O)$_2$;

$R^{12a}$ is $(C_1-C_{10})$-alkyl, $(C_2-C_8)$-alkenyl, $(C_2-C_8)$alkynyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical or the radical $R^{15}$;

$R^{12b}$ is $R^{12a}$—NH;

in all their stereoisomeric forms and mixtures thereof in any ratio, and their physiologically tolerable salts.

Very specifically preferred compounds of the formula I are those in which a substituted methylene radical or substituted ethylene radical representing the group B carries as a substituent a radical from the group consisting of $(C_1-C_8)$-alkyl, $(C_2-C_6)$-alkenyl, $(C_2-C_6)$-alkynyl, $(C_3-C_8)$-cycloalkyl, in particular $(C_5-C_6)$-cycloalkyl, $(C_3-C_8)$-cycloalkyl-$(C_1-C_4)$-alkyl, in particular $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl and heteroaryl-$(C_1-C_4)$-alkyl optionally substituted in the heteroaryl radical, in all their stereoisomeric forms and mixtures thereof in any ratio, and their physiologically tolerable salts.

Even more specifically preferred compounds of the formula I are those in which B is an unsubstituted methylene radical or a methylene radical which is substituted by a $(C_1-C_8)$-alkyl radical, in particular by a $(C_1-C_6)$-alkyl radical, in all their stereoisomeric forms and mixtures thereof in any ratio, and their physiologically tolerable salts.

Generally, compounds of the formula I are preferred which have a uniform configuration at chiral centers, e.g. at the chiral carbon atom representing D and at the center W in the 5-membered ring heterocycle in the formula I.

The compounds of the formula I can be prepared, for example, by fragment condensation of a compound of the formula II

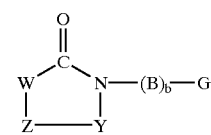
(II)

with a compound of the formula III,

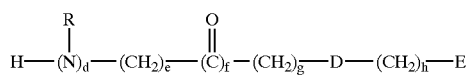
(III)

where W, Y, Z, B, D, E, R and b, d, e, f, g, and h are defined as indicated above and G is hydroxycarbonyl, $(C_1-C_6)$-alkoxycarbonyl, activated carboxylic acid derivatives, such as acid chlorides or active esters, or isocyanato.

For the condensation of the compounds of the formula II with those of the formula III, the coupling methods of peptide chemistry known per se (see, for example, Houben-Weyl, Methoden der Organischen Chemie, [Methods of organic chemistry], Volume 15/1 and 15/2, Georg Thieme Verlag, Stuttgart, 1974) are advantageously used. To do this, as a rule it is necessary that nonreacting amino groups present are protected by reversible protective groups during the condensation. The same applies to carboxyl groups not participating in the reaction, which are preferably present as $(C_1-C_6)$-alkyl, benzyl or tert-butyl esters. Amino group protection is unnecessary if the amino groups to be generated are still present as nitro or cyano groups and are formed, for example, by hydrogenation only after the coupling. After the coupling, the protective groups present are removed in a suitable manner. For example, NO$_2$ groups (guanidino protection), benzyloxycarbonyl groups and benzyl esters can be removed by hydrogenation. The protective groups of the tert-butyl type are removed under acidic conditions, while the 9-fluorenylmethyloxycarbonyl radical is removed by secondary amines.

Compounds of the formula II in which W is $R^1$-A-$C(R^{13})$, Y is a carbonyl group and Z is $NR^0$ can be prepared, for example, by first reacting compounds of the formula IV

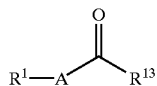
(IV)

in a Bucherer reaction to give compounds of the formula V,

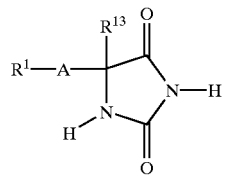
(V)

in which just as in the formula IV $R^1$, $R^{13}$ and A are defined as indicated above (H. T. Bucherer, V. A. Lieb, J. Prakt. Chem. 141(1934), 5). Compounds of the formula VI,

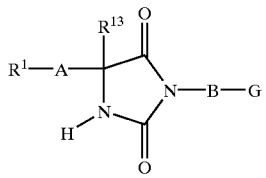
(VI)

in which $R^1$, $R^{13}$, A, B and G are defined as indicated above can then be obtained by first reacting the compounds of the formula V, for example, with an alkylating reagent which introduces the radical —B—G into the molecule. The reaction of compounds of the formula VI with a second reagent of the formula $R^0$—LG, in which $R^0$ has the meanings indicated above and LG is a nucleophilically substitutable leaving group, for example halogen, in particular chlorine or bromine, $(C_1-C_4)$-alkoxy, optionally substituted phenoxy or a heterocyclic leaving group such as, for example, imidazolyl, leads to the corresponding compounds of the formula II. These reactions can be carried out analogously to known methods familiar to the person skilled in the art. Depending on the individual case, it may be appropriate here, as in all steps in the synthesis of the compounds of the formula I, temporarily to block functional groups which could lead to side reactions or undesired reactions by means of a protective group strategy adapted to the synthesis problem, which is known to the person skilled in the art.

If W is $R^1$-A-CH=C, this structural element can be introduced, for example, by condensing an aldehyde with a 5-membered ring heterocycle which contains a methylene group in the position corresponding to the group W analogously to known methods.

Compounds of the formula I in which the 5-membered ring heterocycle is a dioxo- or thioxo-oxo-substituted imidazolidine ring in which W is $R^1$-A-$C(R^{13})$ can also be obtained as follows:

by reaction of α-amino acids or N-substituted α-amino acids or preferably their esters, for example the methyl, ethyl, tert-butyl or benzyl esters, for example of a compound of the formula VII,

(VII)

in which $R^0$, $R^1$, $R^{13}$ and A are defined as indicated above, with an isocyanate or isothiocyanate, for example, of the formula VIII,

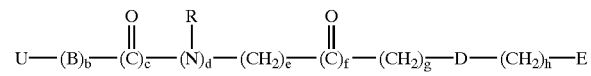
(VIII)

in which B, D, E and R and also b, c, d, e, f, g and h are defined as indicated above and U is isocyanato or isothiocyanato, there are obtained urea or thiourea derivatives, for example of the formula IX

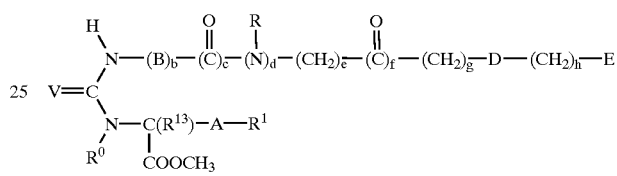
(IX)

for which the definitions indicated above apply and in which V is oxygen or sulfur, and which by heating with acid are cyclized with hydrolysis of the ester functions to give compounds of the formula Ia

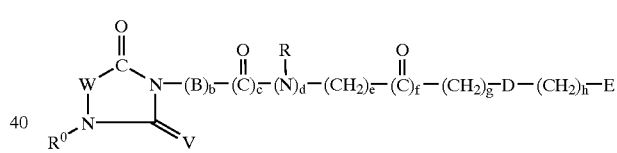
(Ia)

in which V is oxygen or sulfur, W is $R^1$-A-$C(R^{13})$ and for which otherwise the meanings indicated above apply. The cyclization of the compounds of the formula IX to the compounds of the formula Ia can also be carried out by treatment with bases in inert solvents, for example by treatment with sodium hydride in an aprotic solvent such as dimethylformamide.

During the cyclization, guanidino groups can be blocked by protective groups, for example $NO_2$. Amino groups in the side chain can be present in protected form or still as an $NO_2$ or cyano function which can later be reduced to the amino group or, in the case of the cyano group, can also be converted into the formamidino group.

Compounds of the formula I in which the 5-membered ring heterocycle is a dioxo- or thioxo-oxo-substituted imidazolidine ring in which W is $R^1$-A-$C(R^{13})$ and c is 1 can also be obtained by reacting a compound of the formula VII with an isocyanate or isothiocyanate of the formula X

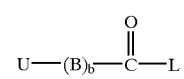
(X)

in which B, U and b are defined as indicated above for the formula VIII and L is an alkoxy group, for example a ($C_1$–$C_4$)-alkoxy group such as methoxy, ethoxy or tert-butoxy, a ($C_6$–$C_{14}$)-aryloxy group, for example phenoxy, or a ($C_6$–$C_{14}$)-aryl-($C_1$–$C_4$)-alkoxy group, for example benzyloxy. In this case, a compound of the formula XI

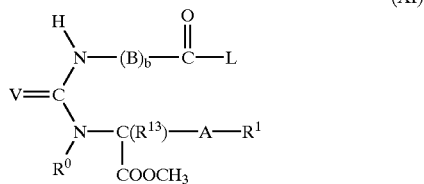

(XI)

is obtained in which A, B, V, L, $R^0$, $R^1$, $R^{13}$ and b are defined as indicated above for the formulae IX and X, which is then cyclized under the influence of an acid or of a base, such as described above for the cyclization of the compounds of the formula IX, to a compound of the formula XII

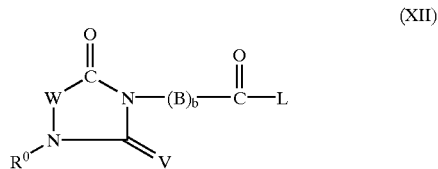

(XII)

in which B, L, V, W, $R^0$ and b are defined as indicated above for the formulae Ia and X. From the compound of the formula XII, a compound of the formula Ia is then obtained by hydrolysis of the group CO—L to give the carboxylic acid COOH and subsequent coupling with a compound of the formula III, as described above for the coupling of the compounds of the formulae II and III. Here too, during the cyclization functional groups can be present in protected form or in the form of precursors, for example guanidino groups are blocked by $NO_2$ or amino groups are present in protected form or still as an $NO_2$ or cyano function which can later be reduced to the amino group or, in the case of the cyano group, can also be converted into the formamidino group.

A further method for the preparation of compounds of the formula Ia is, for example, the reaction of compounds of the formula XIII,

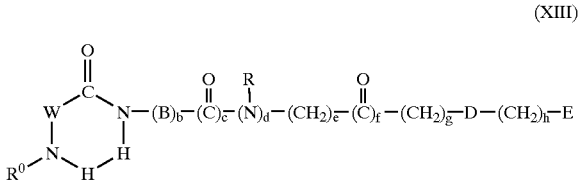

(XIII)

in which W is $R^1$-A-C($R^{13}$) and for which otherwise the definitions indicated above apply, with phosgene, thiophosgene or corresponding equivalents (analogously to S. Goldschmidt and M. Wick, Liebigs Ann. Chem. 575 (1952), 217–231 and C. Tropp, Chem. Ber. 61 (1928), 1431–1439).

A conversion of an amino function into a guanidino function can be carried out using the following reagents:

1. O-Methylisourea (S. Weiss and H. Krommer, Chemiker Zeitung 98 (1974), 617–618)
2. S-Methylisothiourea (R. F. Borne, M. L. Forrester and I. W. Waters, J. Med. Chem. 20 (1977), 771–776)
3. Nitro-S-methylisothiourea (L. S. Hafner and R. E. Evans, J. Org. Chem. 24 (1959) 57)
4. Formamidinosulfonic acid (K. Kim, Y.-T. Lin and H. S. Mosher, Tetrah. Lett. 29 (1988), 3183–3186)
5. 3,5-Dimethyl-1-pyrazolylformamidinium nitrate (F. L. Scott, D. G. O'Donovan and J. Reilly, J. Amer. Chem. Soc. 75 (1953), 4053–4054)
6. N,N'-Di-tert-butyloxycarbonyl-S-methylisothiourea (R. J. Bergeron and J. S. McManis, J. Org. Chem. 52 (1987), 1700–1703)
7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widdig, P. Andrews, H.-P. Schulz and H. Thomas, Arzneim. Forsch./Drug Res. 34 (1984), 531–542).

With respect to the preparation of the compounds of the formula I, the details on the synthesis of the molecular structure which are contained in the following documents are fully incorporated by reference: WO-A-95/14008, German Patent Application 19515177.1 and WO-A-96/33976 corresponding to it, and German Patent Application 19635522.2 and the Patent Applications corresponding to it, for example European Patent Application 97103712.2 and U.S. patent application No. 08/821,253, which are part of the present disclosure.

For the preparation of compounds of the formula I in which $R^1$ is —S—$R^{21}$, the starting materials used can be the corresponding compounds of the formula IV in which $R^1$ is —S—$R^{21}$. If compounds of the formula IV in which $R^1$ is a protected SH group are employed in the Bucherer reaction, compounds of the formula I in which $R^1$ is —SH are obtained after the removal of the protective group. These compounds can in turn be converted into compounds of the formula I in which $R^1$ is —S—$R^{21}$ (with meanings of $R^{21}$ other than hydrogen) by introduction of the radical $R^{21}$, or alternatively serve as intermediates for the preparation of other compounds of the formula I in which the atom bonded to the group A of the radical $R^{21}$ is a sulfur atom.

Compounds of the formula I in which $R^1$ is —S(O)$_2$—$R^{21}$ can be prepared, for example, by oxidizing compounds of the formula I in which $R^1$ is —S—$R^{21}$ to the sulfones according to methods known from the literature (cf. Houben-Weyl, Methoden der Organischen Chemie [Methods of Organic Chemistry], Vol. E12/2, Georg Thieme Verlag, Stuttgart 1985, p. 1058 ff.), i.e. to the compounds of the formula I in which $R^1$ is —S(O)$_2$—$R^{21}$. Correspondingly, compounds of the formula I in which $R^1$ is —S—$R^{21}$ can be oxidized to the sulfoxides under suitable reaction conditions familiar to the person skilled in the art according to methods known per se (cf. Houben-Weyl, Methoden der Organischen Chemie, Vol. E11/1, Georg Thieme Verlag, Stuttgart 1985, p. 702 ff.), i.e. to the compounds of the formula I in which $R^1$ is —S(O)—$R^{21}$. If necessary, in the oxidations to the sulfoxides or to the sulfones, oxidation-sensitive groups in the molecule are protected by suitable protective groups before carrying out the oxidation.

Compounds of the formula I in which $R^1$ is —S(O)$_2$—O$R^{21}$ or —S(O)$_2$—N($R^{21}$)—$R^{28}$ can be prepared, for example, by oxidizing compounds of the formula I in which $R^1$ is —SH according to methods known from the literature (cf. Houben-Weyl, Methoden der Organischen Chemie, Vol. E12/2, Georg Thieme Verlag, Stuttgart 1985, p. 1058 ff.) for the preparation of sulfonic acid derivatives to compounds of the formula I in which $R^1$ is —S(O)$_2$—OH. The compounds of the formula I in which $R^1$ is —S(O)$_2$—O$R^{21}$ or —S(O)$_2$—N($R^{21}$)—$R^{28}$ can then be obtained from these sulfonic acids directly or via corresponding sulfonyl halides by esterification or linkage of an amide bond.

Compounds of the formula I in which $R^1$ is —S(O)—$OR^2$ or —S(O)—$N(R^{21})$—$R^{28}$ can be prepared, for example, by converting compounds of the formula I in which $R^1$ is —SH into the corresponding sulfides, i.e. into the salts in which $R^1$ is —S and the counterion is, for example, an alkali metal ion or an alkaline earth metal ion, and then oxidizing these salts, for example using meta-chloroperbenzoic acid, to the sulfinic acids, i.e. to the compounds of the formula I in which $R^1$ is —S(O)—OH (cf. Houben-Weyl, Methoden der Organischen Chemie, Vol. E11/1, Georg Thieme Verlag, Stuttgart 1985, p. 618 ff.). The corresponding sulfinic acid esters and sulfinamides, i.e. the compounds of the formula I in which $R^1$ is —S(O)—$OR^{21}$ or —S(O)—$N(R^{21})$—$R^{28}$, can be prepared from the sulfinic acids by methods known per se.

If necessary, also in the preparation of sulfonic acid derivatives and sulfinic acid derivatives by oxidation, oxidation-sensitive groups in the molecule are protected by suitable protective groups before carrying out the oxidation.

Apart from the methods mentioned, for the preparation of the compounds of the formula I in which $R^1$ is —S(O)—$R^{22}$, —$S(O)_2$—$R^{22}$, —S(O)—$OR^{21}$, —$S(O)_2$—$OR^{21}$, —S(O)—$N(R^{21})$—$R^{28}$ or —$S(O)_2$—$N(R^{21})$—$R^{28}$ other processes described in the literature for preparing such types of compounds can generally also be used (cf. Houben-Weyl, Methoden der Organischen Chemie, Georg Thieme Verlag, Stuttgart, Vol. E11/1, 1985, p. 618 ff. or Vol. E11/2, 1985, p. 1055 ff.).

Compounds of the formula I in which $R^1$ is further sulfur-containing groups, for example —$N(R^{28})$—C(S)—$OR^{22}$, —$N(R^{28})$—C(S)—$SR^{22}$, —$N(R^{28})$—C(S)—$R^{21}$, —$N(R^{28})$—$S(O)_2$—$R^{22}$, —$N(R^{28})$—S(O)—$R^{22}$, —$N(R^{28})$—$S(O)_2$—$OR^{21}$, —$N(R^{28})$—S(O)—$OR^{21}$, —$N(R^{28})$—$S(O)_2$—$N(R^{21})$—$R^{28}$, —$N(R^{28})$—S(O)—$N(R^{21})$—$R^{28}$, —O—C(S)—$N(R^{21})$—$R^{28}$, —O—$S(O)_2$—$OR^{21}$, —O—S(O)—$OR^{21}$, —O—$S(O)_2$—$N(R^{21})$—$R^{28}$, —O—S(O)—$N(R^{21})$—$R^{28}$, —O—$S(O)_2$—$R^{22}$, O—S(O)—$R^{22}$, —C(S)—$R^{21}$, —C(S)—$N(R^{21})$—$R^{28}$, can be synthesized from suitable precursors by methods known per se and described in the literature (cf Houben-Weyl, Methoden der Organischen Chemie, Vol. E11/1 and E11/2, Georg Thieme Verlag, Stuttgart 1985), the adaptation of the selected synthesis method to the particular target molecule presenting no problems to the person skilled in the art. This also applies to further methods for the preparation of compounds of the formula I in which $R^1$ is —S—$R^{21}$.

The latter also applies to the preparation of the compounds of the formula I in which $R^1$ is one of the phosphorus-containing radicals mentioned in the definition of $R^1$, for example a phosphonic acid derivative or a phosphoric acid derivative. These compounds can be synthesized analogously to methods known from the literature (cf. Houben-Weyl, Methoden der Organischen Chemie, Vol. E1 and E2, Georg Thieme Verlag, Stuttgart 1982) for the preparation of such compounds from suitable precursors.

Compounds of the formula I in which $R^1$ is —$N(R^{28})$—C(O)—NH—$R^{28}$ can be prepared, for example, by reacting the corresponding compounds of the formula I in which $R^1$ is —NH—$R^{28}$ with isocyanates of the formula O—C=N—$R^{28}$ according to methods known from the literature (cf. Houben-Weyl, Methoden der Organischen Chemie, Vol. VIII, Georg Thieme Verlag, Stuttgart 1952, p. 132). Analogously, compounds of the formula I in which $R^1$ is —$N(R^{28})$—C(S)—NH—$R^{28}$ can be prepared, for example, by reacting the corresponding compounds of the formula I in which $R^1$ is —$NHR^{28}$ with isothiocyanates of the formula S=C=N—$R^{28}$. Generally, for the preparation of compounds of the formula I in which $R^1$ is —$N(R^{28})$—C(O)—$N(R^{21})$—$R^{28}$ or —$N(R^{28})$—C(S)—$N(R^{21})$—$R^{28}$, methods known from the literature for the preparation of ureas or thioureas can be used (cf. Houben-Weyl, Methoden der Organischen Chemie, Vol. VIII, Georg Thieme Verlag, Stuttgart 1952).

Compounds of the formula I in which $R^1$ is —$N(R^{29})$—C(O)—$OR^{22}$ can be prepared, for example, by reacting compounds of the formula I in which $R^1$ is —$NHR^{29}$ with chlorocarbonic acid esters of the formula Cl—C(O)—$OR^{22}$ according to methods known from the literature (cf. Houben-Weyl, Methoden der Organischen Chemie, Vol. VIII, Georg Thieme Verlag, Stuttgart 1952, p. 138). Generally, other methods known from the literature can also be used for the preparation of compounds of the formula I in which $R^1$ is —$N(R^{29})$—C(O)—$OR^{22}$ (cf Houben-Weyl, Methoden der Organischen Chemie, Vol. VIII, Georg Thieme Verlag, Stuttgart 1952). Compounds of the formula I in which $R^1$ is —$N(R^{28})$—C(O)—$SR^{22}$ can be prepared analogously.

Compounds of the formula I in which $R^1$ is —O—C(O)—NH—$R^{28}$ can be prepared, for example, by reacting compounds of the formula I in which $R^1$ is —OH with isocyanates of the formula O=C=N—$R^{28}$ according to methods known from the literature (cf. Houben-Weyl, Methoden der Organischen Chemie, Vol. VIII, Georg Thieme Verlag, Stuttgart 1952, p. 141). Analogously, compounds of the formula I in which $R^1$ is —S—C(O)—NH—$R^{28}$ can be prepared, for example, by reacting compounds of the formula I in which $R^1$ is —SH with isocyanates of the formula O=C=N—$R^{28}$. Analogously isothiocyanates of the formula S=C=N—$R^{28}$ can be reacted. Generally, for the preparation of compounds of the formula I in which $R^1$ is —O—C(O)—$N(R^{21})$—$R^{28}$ or —S—C(O)—$N(R^{21})$—$R^{28}$, methods known from the literature for the preparation of such carbonic acid derivatives can be used, for example reactions with carbamoyl halides.

Compounds of the formula I in which $R^1$ is —O—C(O)—$R^{21}$ can be prepared, for example, by reacting compounds of the formula I in which $R^1$ is —OH according to methods known per se and described in the literature (cf. Houben-Weyl, Methoden der Organischen Chemie, Vol. VIII, Georg Thieme Verlag, Stuttgart 1952, p. 508 ff.), for example, with reactive carboxylic acid derivatives. Correspondingly, for example, compounds of the formula I in which $R^1$ is O—C(O)—$OR^{22}$ can be obtained from compounds of the formula I in which $R^1$ is —OH using suitable carbonic acid derivatives such as, for example, chlorocarbonic acid esters.

In accordance with the above details, the compounds of the formula I in which the radicals W, Z, Y, B, R, D, E and b, c, d, e, f, g and h have the meanings indicated at the outset can also be employed as intermediates for the preparation of other compounds, in particular further pharmaceutical active compounds which are obtainable from the compounds of the formula I, for example, by modification or introduction of radicals or functional groups.

The compounds of the formula I in which the radicals W, Z, Y, B, R, D, E and b, c, d, e, f, g and h have the meanings indicated at the outset are antagonists of the adhesion receptor VLA-4 and/or inhibitors of leucocyte adhesion. This applies to the same extent also to the compounds already described in WO-A-96/33976, which are excluded according to the definition given at the outset of those compounds which are claimed per se in the present application, but for which no pharmacological action or pharmaceutical use is described in WO-A-96/33976. The following details of the pharmacological action and use also apply to the last-mentioned compounds. For the preparation of the last-mentioned compounds, reference is made to WO-A-96/33976 and German Patent Application 19515177.1, whose contents are inasmuch part of the present disclosure. With respect to the use of compounds and with respect to pharmaceutical preparations, the present invention thus relates on the one hand to the compounds of the formula I in which the radicals W, Z, Y, B, R, D, E and b, c, d, e, f, g and h have the meanings indicated at the outset, but on the other hand also to the compounds which are excluded according to the definition of the claimed compounds indicated at the outset and which are described in WO-A-96/33976. With respect to the use and pharmaceutical preparation described in the following, the present invention thus relates to compounds of the formula Ib,

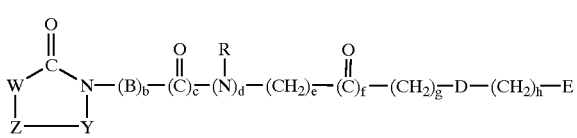

(Ib)

in which

W is $R^1$-A-C($R^{13}$) or $R^1$-A-CH=C;

Y is a carbonyl, thiocarbonyl or methylene group;

Z is N($R^0$), oxygen, sulfur or a methylene group;

A is a bivalent radical from the group consisting of ($C_1$–$C_6$)-alkylene, ($C_3$–$C_{12}$)-cycloalkylene, ($C_1$–$C_6$)-alkylene-($C_3$–$C_{12}$)-cycloalkyl, phenylene, phenylene-($C_1$–$C_6$)-alkyl, ($C_1$–$C_6$)-alkylenephenyl, ($C_1$–$C_6$)-alkylenephenyl-($C_1$–$C_6$)-alkyl, phenylene-($C_2$–$C_6$)-alkenyl or a bivalent radical of a 5- or 6-membered, saturated or unsaturated ring which can contain 1 or 2 nitrogen atoms and can be mono- or disubstituted by ($C_1$–$C_6$)-alkyl or doubly bonded oxygen or sulfur or is a direct bond;

B is a bivalent radical from the group consisting of ($C_1$–$C_6$)-alkylene, ($C_2$–$C_6$)-alkenylene, phenylene, phenylene-($C_1$–$C_3$)-alkyl, ($C_1$–$C_3$)-alkylenephenyl where the bivalent ($C_1$–$C_6$)-alkylene radical can be unsubstituted or substituted by a radical from the group consisting of ($C_1$–$C_8$)-alkyl, ($C_2$–$C_8$)-alkenyl, ($C_2$–$C_8$)-alkynyl, ($C_3$–$C_{10}$)-cycloalkyl, ($C_3$–$C_{10}$)-cycloalkyl-($C_1$–$C_6$)-alkyl, optionally substituted ($C_6$–$C_{14}$)-aryl, ($C_6$–$C_{14}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

D is C($R^2$)($R^3$), N($R^3$) or CH=C($R^3$);

E is tetrazolyl, ($R^8$O)$_2$P(O), HOS(O)$_2$, $R^9$NHS(O)$_2$ or $R^{10}$CO;

R is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be mono- or polysubstituted by fluorine;

$R^0$ is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, CHO, ($C_1$–$C_8$)-alkyl-CO, ($C_3$–$C_{12}$)-cycloalkyl-CO, ($C_3$–$C_{12}$)-cycloalkyl-($C_1$–$C_8$)-alkyl-CO, ($C_6$–$C_{12}$)-bicycloalkyl-CO, ($C_6$–$C_{12}$)-bicycloalkyl-($C_1$–$C_8$)-alkyl-CO, ($C_6$–$C_{12}$)-tricycloalkyl-CO, ($C_6$–$C_{12}$)-tricycloalkyl-($C_1$–$C_8$)-alkyl-CO, optionally substituted ($C_6$–$C_{14}$)-aryl-CO, ($C_6$–$C_{14}$)-aryl-($C_1$–$C_8$)-alkyl-CO optionally substituted in the aryl radical, optionally substituted heteroaryl-CO, heteroaryl-($C_1$–$C_8$)-alkyl-CO optionally substituted in the heteroaryl radical, ($C_1$–$C_8$)-alkyl-S(O)$_n$, ($C_3$–$C_{12}$)-cycloalkyl-S(O)$_n$, ($C_3$–$C_{12}$)-cycloalkyl-($C_1$–$C_8$)-alkyl-S(O)$_n$, ($C_6$–$C_{12}$)-bicycloalkyl-S(O)$_n$, ($C_6$–$C_{12}$)-bicycloalkyl-($C_1$–$C_8$)-alkyl-S(O)$_n$, ($C_6$–$C_{12}$)-tricycloalkyl-S(O)$_n$, ($C_6$–$C_{12}$)-tricycloalkyl-($C_1$–$C_8$)-alkyl-S(O)$_n$, optionally substituted ($C_6$–$C_{14}$)-aryl-S(O)$_n$, ($C_6$–$C_{14}$)-aryl-($C_1$–$C_8$)-alkyl-S(O)$_n$ optionally substituted in the aryl radical, optionally substituted heteroaryl-S(O)$_n$ or heteroaryl-($C_1$–$C_8$)-alkyl-S(O)$_n$ optionally substituted in the heteroaryl radical, where n is 1 or 2;

$R^1$ is one of the radicals —S—$R^{21}$, —S—S—$R^{21}$, —S(O)—$R^{22}$, —S(O)$_2$—$R^{22}$, —S—O$R^{21}$, —S(O)—O$R^{21}$, —S(O)$_2$—O$R^{21}$, —S—N($R^{21}$)—$R^{28}$, —S(O)—N($R^{21}$)—$R^{28}$, —S(O)$_2$—N($R^{21}$)—$R^{28}$, —S—C(O)—$R^{21}$, —S—C(O)—O$R^{22}$, —S—C(S)—S$R^{22}$, —S—C(O)—N($R^{21}$)—$R^{28}$, —S—C(S)—N($R^{21}$)—$R^{28}$, —O—C(O)—$R^{21}$, —O—C(S)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—O$R^{21}$, —O—S(O)—O$R^{21}$, —O—S(O)$_2$—N($R^{21}$)—$R^{28}$, —O—S(O)—N($R^{21}$)—$R^{28}$, —O—S(O)$_2$—$R^{22}$, —O—S(O)—$R^{22}$, —O—P(O)(O$R^{21}$)$_2$, —O—P(O)(O$R^{21}$)—N($R^{21}$)—$R^{28}$, —O—P(O)(N($R^{21}$)—$R^{28}$)$_2$, —N($R^{29}$)—C(O)—O$R^{22}$, —N($R^{28}$)—C(O)—S$R^{22}$, —N($R^{28}$)—C(S)—O$R^{22}$, —N($R^{28}$)—C(S)—S$R^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —N($R^{28}$)—P(O)(O$R^{21}$)$_2$, —N($R^{28}$)—P(O)(O$R^{21}$)—N($R^{21}$)—$R^{28}$, —N($R^{28}$)—P(O)(N($R^{21}$)—$R^{28}$)$_2$, —N($R^{28}$)—P(O)($R^{22}$)—O$R^{21}$, —N($R^{28}$)—P(O)($R^{22}$)—N($R^{21}$)—$R^{28}$, —N($R^{28}$)—P(O)($R^{22}$)$_2$, —P(O)(O$R^{21}$)$_2$, —P(O)(O$R^{21}$)—N($R^{21}$)—$R^{28}$, —P(O)(N($R^{21}$)—$R^{28}$)$_2$, —P(O)($R^{22}$)—O$R^{21}$, —P(O)($R^{22}$)—N($R^{21}$)—$R^{28}$, —P(O)($R^{22}$)$_2$, —C(S)—$R^{21}$, —C(S)—S$R^{21}$, —C(S)—N($R^{21}$)—$R^{28}$, cyano, halogen, nitro or methylenedioxy or the radical of an optionally substituted, 5- to 14-membered, mono- or polycyclic, saturated or unsaturated heterocyclic ring of the formula

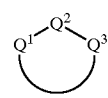

in which $Q^1$ is —C($R^{21}$)$_2$—, =C($R^{21}$)—, —N($R^{28}$)—, —O— or —S—;

$Q^2$ is —S(O)— or —S(O)$_2$—;

$Q^3$ is —C($R^{21}$)$_2$—, =C($R_{21}$)—, —N($R^{28}$)—, —O—, —S—, —C($R^{21}$)(—)— or —N(—)—, where the heterocyclic ring can be bonded to the group A via the free bond in the groups —C($R^{21}$)(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical or ($C_3$–$C_8$)-cycloalkyl;

$R^3$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, ($C_3$–$C_8$)-cycloalkyl, ($C_2$–$C_8$)-alkenyl, ($C_2$–$C_8$)-alkynyl, ($C_2$–$C_8$)-alkenylcarbonyl, ($C_2$–$C_8$)-alkynylcarbonyl, pyridyl, $R^{11}$NH, $R^4$CO, COO$R^4$, CON(CH$_3$)$R^4$, CONHR$^4$, CSNHR$^4$, COOR$^{15}$, CON(CH$_3$)R$^{15}$ or CONHR$^{15}$;

$R^4$ is hydrogen or ($C_1$–$C_{28}$)-alkyl which can optionally be mono- or polysubstituted by identical or different radicals from the group consisting of hydroxyl, hydroxycarbonyl, aminocarbonyl, mono- or di-(($C_1$–$C_{18}$)-alkyl)aminocarbonyl, amino-($C_2$–$C_{18}$)-alkylaminocarbonyl, amino-($C_1$–$C_3$)-alkylphenyl-($C_1$–$C_3$)-alkylaminocarbonyl, ($C_1$–$C_{18}$)-alkylcarbonylamino-($C_1$–$C_3$)-alkylphenyl-($C_1$–$C_3$)-alkylaminocarbonyl, ($C_1$–$C_{18}$)-alkylcarbonylamino-($C_2$–$C_{18}$)-alkylaminocarbonyl, ($C_6$–$C_{14}$)-aryl-($C_1$–$C_8$)-alkoxycarbonyl which can also be substituted in the aryl radical, ammo, mercapto, ($C_1$–$C_{18}$)-alkoxy, ($C_1$–$C_{18}$)-alkoxycarbonyl, Het-CO, optionally substituted ($C_3$–$C_8$)-cycloalkyl, HOS(O)$_2$—($C_1$–$C_3$)-alkyl, $R^9$NHS(O)$_2$—($C_1$–$C_3$)-alkyl, ($R^8$O)$_2$P(O)—($C_1$–$C_3$)-alkyl, tetrazolyl-($C_1$–$C_3$)-alkyl, halogen, nitro, trifluoromethyl or the radical $R^5$;

$R^5$ is optionally substituted ($C_6$–$C_{14}$)-aryl, ($C_6$–$C_{14}$)-aryl-($C_1$–$C_8$)-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6$CO—, where the aryl radical and, independently thereof, the heterocyclic radical can be mono- or polysubstituted by identical or different radicals from the group consisting of ($C_1$–$C_{18}$)-alkyl, ($C_1$–$C_{18}$)-alkoxy, halogen, nitro, amino and trifluoromethyl;

$R^6$ is $R^7R^8$N, $R^7$O or $R^7$S or an amino acid side chain, a natural or unnatural amino acid, imino acid, optionally N—($C_1$–$C_8$)-alkylated or N—($C_6$–$C_{14}$)-aryl-($C_1$–$C_8$)-alkylated) azaamino acid or a dipeptide radical which can also be substituted in the aryl radical and/or in which the peptide bond can be reduced to —NH—CH$_2$—, and their esters and amides, where hydrogen or hydroxymethyl can optionally stand in place of of free functional groups and/or where free functional groups can be protected by protective groups customary in peptide chemistry;

$R^7$ is hydrogen, ($C_1$–$C_{18}$)-alkyl, ($C_6$–$C_{14}$)-aryl-($C_1$–$C_8$)-alkyl, ($C_1$–$C_{18}$)-alkylcarbonyl, ($C_1$–$C_{18}$)-alkoxycarbonyl, ($C_6$–$C_{14}$)-arylcarbonyl, ($C_6$–$C_{14}$)-aryl-($C_1$–$C_8$)-alkylcarbonyl or ($C_6$–$C_{14}$)-aryl-($C_1$–$C_{18}$)-alkyloxycarbonyl, where the alkyl groups can optionally be substituted by an amino group and/or where the aryl radicals can be mono- or polysubstituted, preferably monosubstituted, by identical or different radicals from the group consisting of ($C_1$–$C_8$)-alkyl, ($C_1$–$C_8$)-alkoxy, halogen, nitro, amino and trifluoromethyl, or is a natural or unnatural amino acid, imino acid, optionally N—($C_1$–$C_8$)-alkylated or N—(($C_6$–$C_{14}$)-aryl-($C_1$–$C_8$)-alkylated) azaamino acid or a dipeptide radical which can also be substituted in the aryl radical and/or in which the peptide bond can be reduced to —NH—CH$_2$—;

$R^8$ is hydrogen, ($C_1$–$C_{18}$)-alkyl, optionally substituted ($C_6$–$C_{14}$)-aryl or ($C_6$–$C_{14}$)-aryl-($C_1$–$C_8$)-alkyl which can also be substituted in the aryl radical;

$R^9$ is hydrogen, aminocarbonyl, ($C_1$–$C_{18}$)-alkylaminocarbonyl, ($C_3$–$C_8$)-cycloalkylaminocarbonyl, optionally substituted ($C_6$–$C_{14}$)-arylaminocarbonyl, ($C_1$–$C_{18}$)-alkyl, optionally substituted ($C_6$–$C_{14}$)-aryl or ($C_3$–$C_8$)-cycloalkyl;

$R^{10}$ is hydroxyl, ($C_1$–$C_{18}$)-alkoxy, ($C_6$–$C_{14}$)-aryl-($C_1$–$C_8$)-alkoxy which can also be substituted in the aryl radical, optionally substituted ($C_6$–$C_{14}$)-aryloxy, amino or mono- or di-(($C_1$–$C_{18}$)-alkyl)amino;

$R^{11}$ is hydrogen, $R^{12a}$, $R^{12a}$—CO, H—CO, $R^{12a}$—O—CO, $R^{12b}$—CO, $R^{12b}$—CS, $R^{12a}$—S(O)$_2$ or $R^{12b}$—S(O)$_2$;

$R^{12a}$ is ($C_1$–$C_{18}$)-alkyl, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical or the radical $R^{15}$;

$R^{12b}$ is amino, di-(($C_1$–$C_{18}$)-alkyl)-amino or $R^{12a}$—NH;

$R^{13}$ is hydrogen, ($C_1$–$C_6$)-alkyl, optionally substituted ($C_6$–$C_{14}$)-aryl, ($C_6$–$C_{14}$)-aryl-($C_1$–$C_8$)-alkyl optionally substituted in the aryl radical, ($C_3$–$C_8$)-cycloalkyl or ($C_3$–$C_8$)-cycloalkyl-($C_1$–$C_8$)-alkyl;

$R^{15}$ is $R^{16}$—($C_1$–$C_6$)-alkyl or $R^{16}$;

$R^{16}$ is a 6- to 24-membered, bicyclic or tricyclic radical which is saturated or partially unsaturated and which can also contain one, two, three or four identical or different heteroatoms from the group consisting of nitrogen, oxygen and sulfur and which can also be substituted by one or more identical or different substituents from the group consisting of ($C_1$–$C_4$)-alkyl and oxo;

$R^{21}$ is hydrogen, ($C_1$–$C_8$)-alkyl, hydroxy-($C_1$–$C_8$)-alkyl, ($C_2$–$C_8$)-alkenyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can also be monosubstituted or polysubstituted by fluorine and the radicals $R^{21}$ can be identical or different if they occur two or more times;

$R^{22}$ is ($C_1$–$C_8$)-alkyl, hydroxy-($C_1$–$C_8$)-alkyl, ($C_2$–$C_8$)-alkenyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be monosubstituted or polysubstituted by fluorine and the radicals $R^{22}$ can be identical or different if they occur two or more times;

$R^{28}$ is one of the radicals $R^{21}$—, $R^{21}$N($R^{21}$)—, $R^{21}$C(O)—, $R^{22}$O—C(O)—, $R^{21}$N($R^{21}$)—C(O)— or $R^{21}$N($R^{21}$)—C(=N($R^{21}$))—;

$R^{29}$ is one of the radicals $R^{22}$—, $R^{21}N(R^{21})$—, $R^{21}C(O)$—, $R^{22}O—C(O)$—, $R^{21}N(R^{21})$—C(O)— or $R^{21}N(R^{21})$—C(=N($R^{21}$))—;

Het is the radical of a 5- to 10-membered, monocyclic or polycyclic heterocycle bonded via a nitrogen atom, which can be aromatic or partially unsaturated or saturated and which can contain one, two, three or four identical or different additional ring heteroatoms from the group consisting of oxygen, nitrogen and sulfur and which can be optionally substituted on carbon atoms and on additional ring nitrogen atoms, where there can be identical or different radicals $R^h$, $R^hCO$ or $R^hO$—CO as substituents on additional ring nitrogen atoms and $R^h$ is hydrogen, $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

b, c, d and f independently of one another can be 0 or 1, but cannot all simultaneously be 0;

e, g and h independently of one another are the numbers 0, 1, 2, 3, 4, 5 or 6;

in all their stereoisomeric forms and mixtures thereof in any ratio, and their physiologically tolerable salts.

All the above explanations for the compounds of the formula I, for example with respect to alkyl radicals, aryl radicals, etc., apply to the compounds of the formula Ib correspondingly. All the stereoisomers are also included here. Likewise, all the preferred meanings and preferred compounds indicated above expressly also refer here to the compounds of the formula Ib correspondingly. With respect to the use and the pharmaceutical preparations, preferred compounds of the formula Ib, for example, are thus in turn those compounds in which W is $R^1$-A-C($R^{13}$) or $R^1$-A-CH=C;

Y is a carbonyl, thiocarbonyl or methylene group;

Z is N($R^0$), oxygen, sulfur or a methylene group;

A is a bivalent radical from the group consisting of $(C_1-C_6)$-alkylene, $(C_3-C_{12})$-cycloalkylene, $(C_1-C_6)$-alkylene-$(C_3-C_{12})$-cycloalkyl, phenylene, phenylene-$(C_1-C_6)$-alkyl, $(C_1-C_6)$-alkylenephenyl, $(C_1-C_6)$-alkylenephenyl-$(C_1-C_6)$-alkyl, phenylene-$(C_2-C_6)$-alkenyl or a bivalent radical of a 5- or 6-membered saturated or unsaturated ring which can contain one or two nitrogen atoms and can be mono- or disubstituted by $(C_1-C_6)$-alkyl or doubly bonded oxygen or sulfur, or is a direct bond;

B is a bivalent radical from the group consisting of $(C_1-C_6)$-alkylene, $(C_2-C_6)$-alkenylene, phenylene, phenylene-$(C_1-C_3)$-alkyl, $(C_1-C_3)$-alkylenephenyl;

D is C($R^2$)($R^3$), N($R^3$) or CH=C($R^3$);

E is tetrazolyl, $(R^8O)_2P(O)$, $HOS(O)_2$, $R^9NHS(O)_2$ or $R^{10}CO$;

R and $R^0$ independently of one another are hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$alkyl optionally substituted in the aryl radical, optionally substituted heteroaryl or heteroaryl-$(C_1-C_8)$-alkyl optionally substituted in the heteroaryl radical, where alkyl radicals can be mono- or polysubstituted by fluorine;

$R^1$ is one of the radicals —S—$R^{21}$, —S—S—$R^{21}$, —S(O)—$R^{22}$, —S(O)$_2$—$R^{22}$, —S—O$R^{21}$, —S(O)—O$R^{21}$, —S(O)$_2$—O$R^{21}$, —S—N($R^{21}$)—$R^{28}$, —S(O)—N($R^{21}$)—$R^{28}$, —S(O)$_2$—N($R^{21}$)—$R^{28}$, —S—C(O)—$R^{21}$, —S—C(O)—O$R^{22}$, —S—C(S)—S$R^{22}$, —S—C(O)—N($R^{21}$)—$R^{28}$, —S—C(S)—N($R^{21}$)—$R^{28}$, —O—C(O)—$R^{21}$, —O—C(S)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—O$R^{21}$, —O—S(O)—O$R^{21}$, —O—S(O)$_2$—N($R^{21}$)—$R^{28}$, —O—S(O)—N($R^{21}$)—$R^{28}$, —O—S(O)$_2$—$R^{22}$, —O—S(O)—$R^{22}$, —O—P(O)(O$R^{21}$)$_2$, —O—P(O)(O$R^{21}$)—N($R^{21}$)—$R^{28}$, —O—P(O)(N($R^{21}$)—$R^{28}$)$_2$, —N($R^{29}$)—C(O)—O$R^{22}$, —N($R^{28}$)—C(O)—S$R^{22}$, —N($R^{28}$)—C(S)—O$R^{22}$, —N($R^{28}$)—C(S)—S$R^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —N($R^{28}$)—P(O)(O$R^{21}$)$_2$, —N($R^{28}$)—P(O)(O$R^{21}$)—N($R^{21}$)—$R^{28}$, —N($R^{28}$)—P(O)(N($R^{21}$)—$R^{28}$)$_2$, —N($R^{28}$)—P(O)($R^{22}$)—O$R^{21}$, —N($R^{28}$)—P(O)($R^{22}$)—N($R^{21}$)—$R^{28}$, —N($R^{28}$)—P(O)($R^{22}$)$_2$, —P(O)(O$R^{21}$)$_2$, —P(O)(O$R^{21}$)—N($R^{21}$)—$R^{28}$, —P(O)(N($R^{21}$)—$R^{28}$)$_2$, —P(O)($R^{22}$)—O$R^{21}$, —P(O)($R^{22}$)—N($R^{21}$)—$R^{28}$, —P(O)($R^{22}$)$_2$, —C(S)—$R^{21}$, —C(S)—S$R^{21}$, —C(S)—N($R^{21}$)—$R^{28}$, cyano, halogen, nitro or methylenedioxy or the radical of an optionally substituted, 5- to 14-membered, mono- or polycyclic, saturated or unsaturated heterocyclic ring of the formula

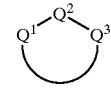

in which $Q^1$ is —C($R^{21}$)$_2$—, =C($R^{21}$)—, —N($R^{28}$)—, —O— or —S—;

$Q^2$ is —S(O)— or —S(O)$_2$—;

$Q^3$ is —C($R^{21}$)$_2$—, =C($R^{21}$)—, —N($R^{28}$)—, —O—, —S—, —C($R^{21}$)(—)— or —N(—)—, where the heterocyclic ring can be bonded to the group A via the free bond in the groups —C($R^{21}$)(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_{83})$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}NH$, $R^4CO$, COO$R^4$, CON(CH$_3$)$R^4$, CONH$R^4$, CSNH$R^4$, COO$R^{15}$, CON(CH$_3$)$R^{15}$ or CONH$R^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-(($C_1-C_{18}$)-alkyl)aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, $HOS(O)_2$-$(C_1-C_3)$-alkyl, $R^9NHS(O)_2$—$(C_1-C_3)$-alkyl, $(R^8O)_2P(O)$—$(C_1-C_3)$-alkyl, tetrazolyl-$(C_1-C_3)$-alkyl, halogen, nitro, trifluoromethyl and the radical $R^5$;

$R^5$ is optionally substituted $(C_6-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino or trifluoromethyl;

$R^6$ is $R^7R^8N$, $R^7O$ or $R^7S$ or an amino acid side chain, a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—$CH_2$—, and their esters and amides, where hydrogen or hydroxymethyl can optionally stand in place of of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted, preferably monosubstituted, by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—$CH_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}CO$, optionally substituted $(C_6-C_{14})$-aryl-$S(O)_2$, $(C_1-C_{18})$-alkyl-$S(O)_2$, $(C_6-C_{14})$-aryl-$(C_1-C_8)$-alkyl optionally substituted in the aryl radical, $R^9NHS(O)_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino, the radical $R^{15}$ or the radical $R^{15}$—O—;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$—$(C_1-C_6)$-alkyl or $R^{16}$;

$R^{16}$ is a 6- to 24-membered, bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, hydroxy-$(C_1-C_8)$-alkyl, $(C_2-C_8)$-alkenyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where alkyl radicals can also be monosubstituted or polysubstituted by fluorine and the radicals $R^{21}$ can be identical or different if they occur two or more times;

$R^{22}$ is $(C_1-C_8)$-alkyl, hydroxy-$(C_1-C_8)$-alkyl, $(C_2-C_8)$-alkenyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where alkyl radicals can be monosubstituted or polysubstituted by fluorine and the radicals $R^{22}$ can be identical or different if they occur two or more times;

$R^{28}$ is one of the radicals $R^{21}$—, $R^{21}N(R^{21})$—, $R^{21}C(O)$, $R^{22}O$—C(O)—, $R^{21}N(R^{21})$—C(O)— or $R^{21}N(R^{21})$—C(=N($R^{21}$))—;

$R^{29}$ is one of the radicals $R^{22}$—, $R^{21}N(R^{21})$—, $R^{21}C(O)$—, $R^{22}O$—C(O)—, $R^{21}N(R^{21})$—C(O)— or $R^{21}N(R^{21})$—C(=N($R^{21}$))—;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and their physiologically tolerable salts.

The compounds of the formula Ib according to the above definition have the ability to inhibit the adhesion receptor VLA-4 and to inhibit cell-cell and cell-matrix interaction processes in which interactions between VLA-4 and its ligands play a part. The activity of the compounds of the formula Ib can be demonstrated, for example, in an assay in which the binding of cells which contain the VLA-4 receptor, for example leucocytes, to ligands of this receptor is measured, for example to VCAM-1, which for this purpose can advantageously also be prepared by genetic engineering. Details of such an assay are described below. In particular, the compounds of the formula Ib are able to inhibit the adhesion and the migration of leucocytes, for example the adhesion of leucocytes to endothelial cells which—as explained above—is controlled via the VCAM-1/VLA-4 adhesion mechanism.

The compounds of the formula Ib and their physiologically tolerable salts are therefore suitable for the treatment and prophylaxis of diseases which are based on the interaction between the VLA-4 receptor and its ligands or can be influenced by inhibition of this interaction, and in particular they are suitable for the treatment and prophylaxis of diseases which are caused at least partially by an undesired extent of leucocyte adhesion and/or leucocyte migration or which are associated therewith, and for whose prevention, alleviation or cure the adhesion and/or migration of leucocytes should be reduced. They can thus be employed, for example, as antinflammatory agents in the case of inflammatory symptoms having very different causes. The compounds of the formula Ib according to the present invention are used, for example, for the treatment or prophylaxis of rheumatoid arthritis, inflammatory bowel disease (ulcerative colitis), systemic lupus erythematosus or for the treatment or prophylaxis of inflammatory disorders of the central nervous system, such as, for example, multiple sclerosis, for the treatment or prophylaxis of asthma or of allergies, for example allergies of the delayed type (type IV allergy), furthermore for the treatment or prophylaxis of cardiovascular disorders, arteriosclerosis, restenosis, for the treatment or prophylaxis of diabetes, for the prevention of damage to organ transplants, for the inhibition of tumor growth or tumor metastasis in various malignancies, for the therapy of malaria, and also of other diseases in which blocking of the integrin VLA-4 and/or influencing of the leucocyte activity appears appropriate for prevention, alleviation or cure. The compounds of the formula Ib and their salts can furthermore be employed for diagnostic purposes, e.g. in in vitro diagnoses, and as tools in biochemical investigations in which VLA-4 blocking or influencing of cell-cell or cell-matrix interactions is intended.

The compounds of the formula Ib and their physiologically tolerable salts can be administered according to the invention, as pharmaceuticals for therapy or prophylaxis, to animals, preferably to mammals, and in particular to man. They can be administered per se, in mixtures with one another or in the form of pharmaceutical preparations which permit enteral or parenteral use and which as active constituents contain an efficacious dose of at least one compound of the formula Ib and/or its physiologically tolerable salts in addition to customary, pharmaceutically innocuous excipients and/or additives. The pharmaceutical preparations normally contain approximately 0.5 to 90% by weight of the therapeutically active compounds of the formula Ib and/or their physiologically tolerable salts.

The present invention relates to the compounds of the formula Ib and/or their physiologically tolerable salts for use as pharmaceuticals, the use of the compounds of the formula Ib and/or their physiologically tolerable salts for the production of pharmaceuticals for the inhibition of the adhesion and/or migration of leucocytes or for the inhibition of the VLA-4 receptor, i.e. of pharmaceuticals for the treatment or prophylaxis of diseases in which leucocyte adhesion and/or leucocyte migration has an undesired extent, or of diseases in which VLA-4-dependent adhesion processes play a part, in particular for the production of pharmaceuticals for the inhibition of inflammation, and also the use of the compounds of the formula Ib and/or their physiologically tolerable salts in the treatment and prophylaxis of diseases of this type. The present invention furthermore relates to pharmaceutical preparations which contain an efficacious dose of at least one compound of the formula Ib and/or its physiologically tolerable salts in addition to customary pharmaceutically innocuous excipients and/or additives.

The pharmaceuticals can be administered orally, for example in the form of pills, tablets, film-coated tablets, sugar-coated tablets, granules, hard and soft gelatin capsules, solutions, syrups, emulsions or suspensions. However, administration can also take place rectally, for example in the form of suppositories, or parenterally, for example in the form of injection or infusion solutions, microcapsules or rods, or percutaneously, for example in the form of ointments or tinctures, or by other routes, for example in the form of nasal sprays or aerosol mixtures.

The pharmaceutical preparations to be employed according to the invention are prepared in a manner known per se, pharmaceutically inert inorganic and/or organic excipients being used in addition to the compound(s) of the formula Ib and/or its/their physiologically tolerable salts. For the production of pills, tablets, sugarcoated tablets and hard gelatin capsules, it is possible to use, for example, lactose, corn starch or derivatives thereof, talc, stearic acid or its salts, etc. Excipients for soft gelatin capsules and suppositories are, for example, fats, waxes, semisolid and liquid polyols, natural or hardened oils, etc. Suitable excipients for the preparation of solutions, for example injection solutions, or of emulsions or syrups are, for example, water, alcohols, glycerol, polyols, sucrose, invert sugar, glucose, vegetable oils, etc. Suitable excipients for microcapsules, implants or rods are, for example, copolymers of glycolic acid and lactic acid.

In addition to the active compounds and excipients the pharmaceutical preparations can additionally contain additives, such as, for example, fillers, disintegrants, binders, lubricants, wetting agents, stabilizers, emulsifiers, preservatives, sweeteners, colorants, flavorings or aromatizers, thickeners, diluents, buffer substances, and also solvents or solubilizers or agents for achieving a depot effect, as well as salts for changing the osmotic pressure, coatings or antioxidants. They can also contain two or more compounds of the formula Ib and/or their physiologically tolerable salts. In addition to at least one compound of the formula Ib and/or its physiologically tolerable salts, they can further contain one or more other therapeutically or prophylactically active substances, for example substances having antiinflammatory action.

The dose can vary within wide limits and is to be adapted to the individual conditions in each individual case. In general, in the case of oral administration a daily dose of approximately 0.01 to 100 mg/kg, preferably 0.1 to 10 mg/kg, in particular 0.3 to 2 mg/kg of body weight is adequate to achieve effective results. In the case of intravenous administration, the daily dose is in general approximately 0.01 to 50 mg/kg, preferably 0.01 to 10 mg/kg of body weight. The daily dose can be subdivided, in particular in the case of administration of relatively large amounts, into a number of, for example 2, 3 or 4, part administrations. Where appropriate, it may be necessary, depending on individual behavior, to deviate upwards or downwards from the indicated daily dose. Pharmaceutical preparations normally contain 0.2 to 500 mg, preferably 1 to 100 mg, of active compound of the formula Ib and/or its physiologically tolerable salts per dose.

EXAMPLES

The products were identified by means of mass spectra (MS) and/or NMR spectra. Compounds which were purified by chromatography using an eluent which contained, for example, acetic acid or trifluoroacetic acid and were then freeze-dried partly still contained, depending on the freeze-drying procedure, the acid contained in the eluent, and were thus partially or completely obtained in the form of a salt, for example in the form of the acetic acid salt or trifluoroacetic acid salt.

The abbreviations have the following meanings:
THF Tetrahydrofuran
DMF N,N-Dimethylformamide
DCC N,N'-Dicyclohexylcarbodiimide
HOBt 1-Hydroxybenzotriazole Example 1

((R,S)-4-(4-(Cyanophenyl)-4-methyl-3-(2-naphthylmethyl)-2,5-dioxoimidazolidin-1-yl)acetyl-L-aspartyl-L-phenylglycine

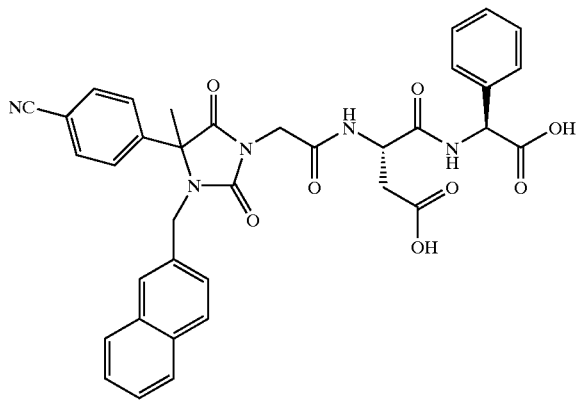

1a) (R,S)-4-(4-Cyanophenyl)-4-methyl-2,5-dioxoimidazolidine 20 g (138 mmol) of p-acetylbenzonitrile, 115.6 g of ammonium carbonate (1.21 mol) and 11.6 g of potassium cyanide (178 mmol) were dissolved in 600 ml of a mixture of 50% ethanol and 50% water. The mixture was stirred at 55° C. for 5 hours and allowed to stand at room temperature overnight. The solution was adjusted to pH=6.3 using 6 N HCl and then stirred at room temperature for 2 hours. The precipitate was filtered off with suction, washed with water and dried over phosphorus pentoxide in a high vacuum. Yield: 22.33 g (75%).

FAB-MS: 216.1 (M+H)$^+$

1b) Methyl ((R,S)-4-(4-cyanophenyl)-4-methyl-2,5-dioxoimidazolidin-1-yl)acetate 1.068 g of sodium (46.47 mmol) were dissolved in 110 ml of abs. methanol under nitrogen. The clear solution was treated with 10 g of (R,S)-4-(4-cyanophenyl)-4-methyl-2,5-dioxoimidazolidine (46.47 mmol) and the mixture was boiled under reflux for 2 h. 7.75 g (46.68 mmol) of potassium iodide were added and a solution of 4.53 ml of methyl chloroacetate (51.3 mmol) in 5 ml of methanol was added dropwise in the course of 1 hour. The mixture was heated to boiling for 6 hours, allowed to stand at room temperature overnight and concentrated. The oily residue was chromatographed on silica gel using methylene chloride/ethyl acetate (9:1). Yield: 8.81 g (66%).

FAB-MS: 288 (M+H)$^+$

1c) Methyl ((R,S)4-(4-cyanophenyl)4-methyl-3-(2-naphthylmethyl-2,5-dioxoimidazolidin-1-yl)acetate 5 g of methyl ((R,S)-4-(4-cyanophenyl)-4-methyl-2,5-dioxoimidazolidin-1-yl)acetate (17.4 mmol) were dissolved in 20 ml of anhydrous DMF under argon. 920 mg of a sodium hydride dispersion in mineral oil (19.14 mmol) were added in an argon countercurrent. The reaction mixture was stirred at room temperature for 15 minutes. A solution of 3.85 g of 2-bromomethylnaphthalene (19.14 mmol) in 10 ml of anhydrous DMF was then added. The mixture was stirred at room temperature for 4 hours and then allowed to stand at room temperature overnight. The solution was concentrated. For purification, the substance was chromatographed on silica gel using methylene chloride/ethyl acetate (9.75:0.25). The fractions containing the pure substance were concentrated. Yield: 5.15 g of oil (69%).

FAB-MS: 428.3 (M+H)$^+$ 1d) ((R,S)-4-(4-cyanophenyl)-4-methyl-3-(2-naphthylmethyl)-2,5-dioxoimidazoldin-1-yl)acetic acid 1.1 g of methyl ((R,S)-4-(4-cyanophenyl)-4-methyl-3-(2-naphthylmethyl)-2,5-dioxoimidazolidin-1-yl)acetate (2.57 mmol) were dissolved in a mixture of 20 ml of 6 N HCl and 10 ml of dioxane. The solution was stirred at 70° C. for 3 hours and then concentrated.

Yield: 1.2 g of crude product. FAB-MS: 414.2 (M+H)$^+$ 1e) ((R,S)-4-(4-cyanophenyl)-4-methyl-3-(2-naphthylmethyl)-2,5-dioxoimidazolidin 1-yl)acetyl-L-aspartyl-L-phenylglycine di-tert-butyl ester 515 mg of DCC (2.34 mmol) were added at 0° C. to a solution of 1.2 g of ((R,S)-4-(4–Cyanophenyl)-4-methyl-3-(2-naphthylmethyl)-2,5-dioxoimidazolidin-1-yl)acetic acid (crude product), 0.97 g of H-Asp(OBu$^t$-Phg-OBu$^t$ hydrochloride (2.34 mmol) and 320 mg of HOBt (2.34 mmol) in 25 ml of DMF. The mixture was stirred at 0° C. for 1 hour and at room temperature for 3 hours. The batch was then allowed to stand at room temperature overnight, the precipitate was filtered off with suction and the filtrate was concentrated. For purification, the substance was chromatographed on silica gel, first with methylene chloride/methanol/glacial acetic acid (9.5:0.5:0.05) and then with methylene chloride/ethyl acetate (8:2). Yield: 620 mg of an oil (34.4%).

FAB-MS: 774.3 (M+H)$^+$ 1f) ((R,S)-4-(4-cyanophenyl)-4-methyl-3-(2-naphthylmethyl)-2,5-dioxoimidazolidin-1-yl)acetyl-L-aspartyl-L-phenylglycine 250 mg of ((R,S)-4-(4-cyanophenyl)-4-methyl-3-(2-naphthylmethyl)-2,5dioxoimidazolidin-1-yl)acetyl-L-aspartyl-L-phenylglycine di-tert-butyl ester were dissolved in a mixture of 2.25 ml of trifluoroacetic acid and 0.25 ml of water. The mixture was allowed to stand at room temperature for one hour and was concentrated in a water-jet vacuum. For purification, the substance was chromatographed on Sephadex LH20 using a mixture of glacial acetic acid, n-butanol and water. The fractions containing the pure substance were concentrated. The residue was dissolved in water, freeze-dried and, for further purification, chromatographed on silica gel using methylene chloride/methanol/glacial acetic acid/water (9:1:0.01:0.1).

Yield: 78 mg (36.8%). FAB-MS: 662.2 (M+H)$^+$

Example 2

((R,S)-3-Benzyl-4-methyl-4-(4-nitrophenyl)-2,5-dioxoimidazolidin-1-yl)acetyl-L-aspartyl-L-phenylglycine

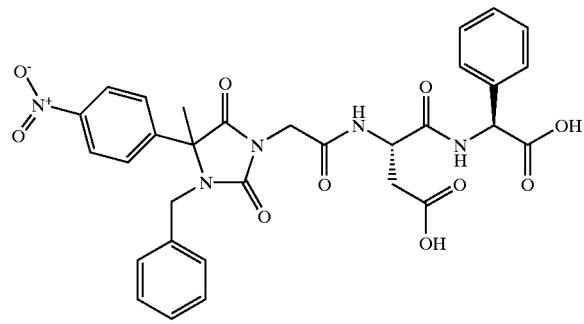

2a) (R,S)-4-Methyl-4-(4-nitrophenyl)-2,5-dioxoimidazolidine

A mixture of 20 g (121 mmol) of 4-nitroacetophenone, 101.65 g (1.06 mol) of ammonium carbonate and 10.2 g (156 mmol) of potassium cyanide in 400 ml of ethanol/water (1:1) was heated at 50° C. for 5 h. The solution was then adjusted to pH=6.3 using 6 N hydrochloric acid and stirred at room temperature for 2 h. The precipitate was filtered off with suction, washed with water and dried over phosphorus pentoxide in a high vacuum. Yield: 27.37 g (96%) of colorless solid.

2b) ((R,S)-3-Benzyl-4-methyl-4-(4-nitrophenyl)-2,5-dioxoimidazolidin-1-yl)acetic acid The compound was prepared analogously to Example 1 by reaction of (R,S)-4-methyl-4-(4-nitrophenyl)-2,5-dioxoimidazolidine with methyl bromoacetate and then benzyl bromide (instead of 2-bromomethylnaphthalene) and cleavage of the methyl ester with 6 N hydrochloric acid.

2c) ((R,S)-3-Benzyl-4-methyl-4-(4-nitrophenyl)-2,5-dioxoimidazolidin-l-yl)acetyl-L-aspartyl-L-phenylglycine A solution of 383 mg (1 mmol) of ((R,S)-3-benzyl-4-methyl-4-(4-nitrophenyl)-2,5-dioxoimidazolidin-l-yl)acetic acid, 414 mg (1 mmol) of H-Asp(O'Bu)-Phg-(O'Bu)×HCl and 135 mg (1 mmol) of HOBt in 5 ml of absolute DMF was treated at 0° C. with 220 mg (1.1 mmol) of DCC. After stirring at 0° C. for 60 minutes and at room temperature for 60 minutes, the precipitate was filtered off with suction, the filtrate was concentrated and the residue was taken up in ethyl acetate. After filtration, the ethyl acetate solution was washed in succession with saturated $NaHCO_3$ solution, $KHSO_4/K_2SO_4$ solution, saturated $NaHCO_3$ solution and water. After phase separation, the organic phase was dried over sodium sulfate. The drying agent was filtered off, the solvent was removed in vacuo and the residue was chromatographed on silica gel using dichloromethane/ethyl acetate (9:1). After concentration of the product fractions, the residue was treated with 10 ml of 90% strength trifluoroacetic acid. After 1 h at room temperature, the trifluoroacetic acid was removed in vacuo and the residue was chromatographed on silica gel using dichloromethane/methanol/glacial acetic acid/water (9:1:0.1:0.1) and then on Sephadex LH20 using water/butanol/acetic acid (43:4.3:3.5). After freeze-drying of the product fractions, 23 mg (4%) of the title compound were obtained.

ES(+)-MS: 632 (M+H)⁺

Example 3

((R,S)-3-Benzyl-4-methyl-4-(4-(3-(2-methylphenyl)ureido)phenyl)-2,5-dioxoimidazolidin-1-yl)acetyl-L-aspartyl-L-phenylglycine

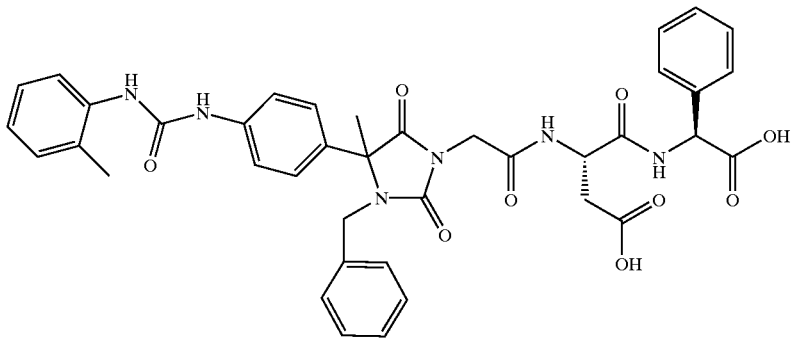

3a) Methyl ((R,S)-3-benzyl-4-methyl-4-(4-nitrophenyl)-2,5-dioxoimidazolidin-1-yl)acetate The compound was prepared from (R,S)-4-methyl-(4-nitrophenyl)-2,5-dioxoimidazolidine (synthesized from 4-nitroacetophenone as described in Example 2) analogously to Example 1.

3b) Methyl ((R,S)-4-(4-aminophenyl)-3-benzyl-4-methyl-2,5-dioxoimidazolidin-1-yl)acetate A solution of 8.92 g (22.45 mmol) of methyl ((R,S)-3-benzyl-4-methyl-4-(4-nitrophenyl)-2,5-dioxoimidazolidin-1-yl)acetate in 280 ml of absolute methanol was treated with 17 g (90 mmol) of tin chloride and 3 drops of acetic acid and heated at 50° C. After starting material was no longer detectable according to HPLC checking, the reaction mixture was concentrated in vacuo and the residue was filtered through silica gel using methanol. After concentration, 6.39 g (78%) of the title compound were obtained.

3c) Methyl ((R,S)-3-benzyl-4-methyl-4-(4-(3-(2-methylphenyl)ureido)-phenyl)-2,5-dioxoimidazolidin-1-yl)acetate 0.91 g (6.8 mmol) of ortho-tolyl isocyanate in 2 ml of THF was added to a solution of 2.5 g (6.8 mmol) of methyl ((R,S)-4-(4-aminophenyl)-3-benzyl-4-methyl-2,5-dioxoimidazolidin-1-yl)acetate in 20 ml of THF. After heating under reflux for 5 h, the reaction mixture was allowed to stand at room temperature overnight, a further 0.18 g (1.36 mmol) of ortho-tolyl isocyanate was added and it was stirred under reflux for 3 h. The reaction mixture was concentrated and the residue was purified on silica gel by means of MPLC using heptane/ethyl acetate (1:1). After concentration of the product fractions, 1.35 g (40%) of the title compound were obtained.

3d) ((R,S)-3-Benzyl-4-methyl-4-(4-(3-(2-methylphenyl)ureido)phenyl)-2,5-dioxoimidazolidin-1-yl)acetyl-L-aspartyl-L-phenylglycine The synthesis was carried out analogously to Example 2 by coupling of ((R,S)-3-benzyl-4-methyl-4-(4-(3-(2-methylphenyl)ureido)phenyl)-2,5-dioxoimidazolidin-1-yl)acetic acid (prepared by cleavage of methyl ((R,S)-3-benzyl-4-methyl-4-(4-(3-(2-methylphenyl)ureido)phenyl)-2,5-dioxoimidazolidin-1-yl)acetate with 6 N hydrochloric acid analogously to Example 1) and H-Asp(O$^t$Bu)-Phg-(O$^t$Bu)× HCl. After cleavage of the tert-butyl ester with 90% strength trifluoroacetic acid, the crude product was purified by preparative HPLC on RP-18.

ES(+)-MS: 735 (M+H)$^+$

Example 4

((R,S)-3-Benzyl-4-(4-(3-benzylureidomethyl)phenyl)-4-methyl-2,5-dioxoimidazolidin-1-yl)acetyl-L-aspartyl-L-phenylglycine

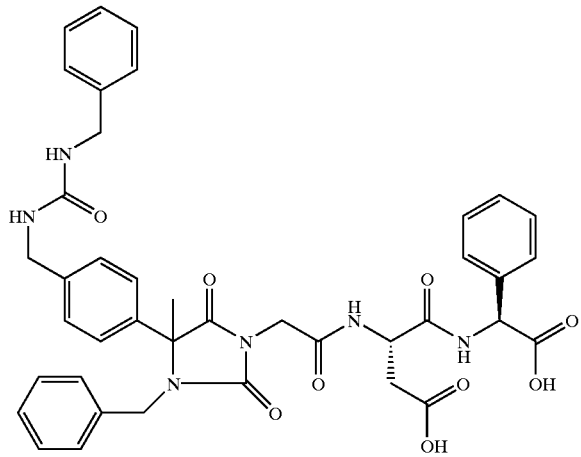

4a) Methyl ((R,S)-3-benzyl-4-(4-cyanophenyl)4-methyl-2,5-dioxoimidazolidin-1-yl)acetate 28.7 g (100 mmol) of methyl ((R,S)-4-(4-cyanophenyl)-4-methyl-2,5-dioxoimidazolidin-1-yl)acetate were dissolved in 160 ml of anhydrous DMF under argon. 5.28 g (110 mmol) of NaH were added in portions with stirring at 0° C. The mixture was stirred at 0° C. for 30 minutes. 13 ml of benzyl bromide were then slowly added dropwise. The mixture was stirred at room temperature for 5 hours and allowed to stand at room temperature overnight. The almost clear solution was filtered with suction and concentrated in a high vacuum. The residue was dissolved in ethyl acetate, the solution was washed with water and the aqueous phase was washed with ethyl acetate. The combined organic phases were washed with water, dried with anhydrous magnesium sulfate and concentrated. For purification, the crude product was chromatographed on silica gel (70–200 μm) in n-heptane/ethyl acetate (1:1). 35.7 g (94.6%) of the title compound were obtained as an oil.

4b) Methyl ((R,S)-4-(4-(aminomethyl)phenyl)-3-benzyl-4-methyl-2,5-dioxo-imidazolidin-1-yl)acetate 15.2 g (40 mmol) of methyl ((R,S)-3-benzyl-4-(4-cyanophenyl)-4-methyl-2,5-dioxoimidazolidin-1-yl)acetate (4a) were dissolved in 160 ml of a mixture of ethanol and 50% strength acetic acid (8:2), treated with 3 g of Pd/carbon and hydrogenated for 7 hours in an autoclave at 3 bar of H$_2$. The catalyst was filtered off with suction and the filtrate was concentrated. The residue was dissolved in dichloromethane and chromatographed on silica gel (70–200 μm) using dichloromethane and then dichloromethane/methanol (8:2). 15.3 g (100%) of the title compound were obtained.

4c) Methyl ((R,S)-3-benzyl-4-(4-(3-benzylureidomethyl)phenyl)-4-methyl-2,5-dioxoimidazolidin-1-yl)acetate 3.80 g (10 mmol) of methyl ((R,S)-4-4-(aminomethyl)phenyl)-3-benzyl-4-methyl-2,5-dioxoimidazolidin-1-yl)acetate (4b) were dissolved in 20 ml of anhydrous dichloromethane under argon. 1.85 ml (2 g; 15 mmol) of benzyl isocyanate and 2 drops of triethylamine were added. The mixture was stirred at room temperature for 2 hours and the solution was concentrated a little. It was diluted with ethyl acetate and washed 2× with 5% strength citric acid, 2× with saturated NaHCO$_3$ solution and 1× with water/NaCl solution. The solution was dried over anhydrous sodium sulfate and concentrated. 5.09 g (98.9%) of the title compound were obtained as an oil.

4d) ((RS)-3-Benzyl-4-(4-(3-benzylureidomethyl)phenyl)-4-methyl-2,5-dioxoimidazolidin-1-yl)acetic acid 1 g (1.94 mmol) of methyl ((R,S)-3-benzyl-4-(4-(3-benzylureidomethyl)-phenyl)-4-methyl-2,5-dioxoimidazolidin-1-yl)acetate (4c) were refluxed for 5 hours with 20 ml of concentrated hydrochloric acid. The mixture was then concentrated. The residue was triturated with water, cooled and filtered off with suction. 700 mg (72%) of the title compound were obtained.

4e) ((R,S)-3-Benzyl-4-(4-(3-benzylureidomethyl)phenyl)-4-methyl-2,5-dioxoimidazolidin-1-yl)acetyl-L-aspartyl-L-phenylglycine di-tert-butyl ester 500 mg (1 mmol) of ((R,S)-3-benzyl-4-(4-(3-benzylureidomethyl)phenyl)-4-methyl-2,5-dioxoimidazolidin-1-yl)acetic acid (4d), 414.9 mg (1 mmol) of H-Asp(O$^t$Bu)-Phg-(O$^t$Bu)×HCl and 135 mg (1 mmol) of HOBt were dissolved in 10 ml of absolute DMF. 413 ml (1 mmol) of N-ethylmorpholine and 220 mg (1.1 mmol) of DCC were added at 0° C. The mixture was stirred at 0° C. for 1 hour and at room temperature for 3 hours. It was allowed to stand at room temperature overnight, the urea precipitate was filtered off with suction and the filtrate was concentrated in a high vacuum. The residue was taken up in ethyl acetate, and washed with saturated NaHCO$_3$ solution, KHSO$_4$/K$_2$SO$_4$ solution and with water/NaCl solution. The organic phase was dried with anhydrous sodium sulfate and concentrated, and the oily residue was dried in a high vacuum. 800 mg (92.9%) of the title compound were obtained.

4f) ((R,S)-3-Benzyl-4-(4-(3-benzylureidomethyl)phenyl)-4-methyl-2,5-dioxoimidazolidin-1-yl)acetyl-L-aspartyl-L-phenylglycine 800 mg (0.93 mmol) of ((R,S)-3-benzyl-4-(4-(3-benzylureidomethyl)phenyl)-4-methyl-2,5-dioxoimidazolidin-1-yl)acetyl-L-aspartyl-L-phenylglycine di-tert-butyl ester (4e) were dissolved in 8 ml of 90% strength trifluoroacetic acid and allowed to stand at room temperature for 1 hour. The mixture was then concentrated and the residue was triturated with diethyl ether. The crude product was purified by chromatography on silica gel using dichloromethane/methanol/acetic acid/water (9:1:0.1:0.1). 527 mg (76%) of the title compound were obtained.

ES(+)-MS: 749.3 (M+H)$^+$

Example 5

((RS)-3-Benzyl-4-methyl-4-(4-(3-phenylureidomethyl)phenyl)-2,5-dioxoimidazolidin-1-yl)acetyl-L-aspartyl-L-phenylglycine

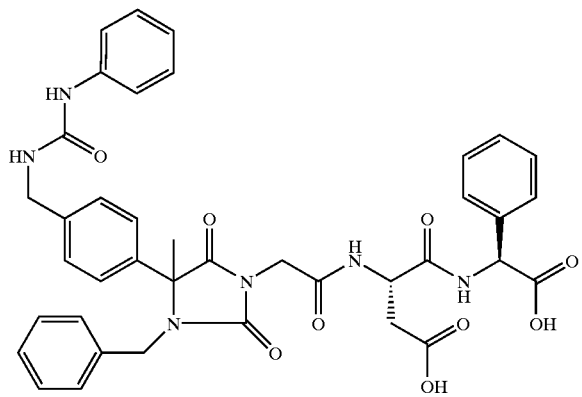

The synthesis was carried out analogously to Example 4. After cleavage of the tert-butyl ester using 90% strength trifluoroacetic acid, the crude product was purified by chromatography on silica gel using dichloromethane/methanol/acetic acid/water (9:1:0.1:0.1).

ES(+)-MS: 735.2 (M+H)$^+$

Example 6

((R,S)-3-Benzyl-4-methyl-4-(4-(3-(2-methylphenyl)ureidomethyl)phenyl)-2,5-dioxoimidazolidin-1-yl)acetyl-L-aspartyl-L-phenylglycine

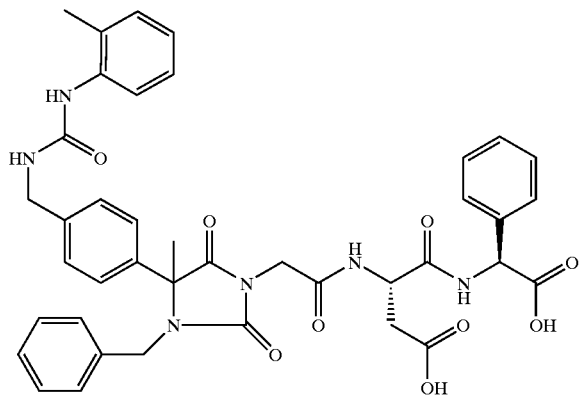

The synthesis was carried out analogously to Example 4. After cleavage of the tert-butyl ester using 90% strength trifluoroacetic acid, the crude product was purified by chromatography on silica gel using dichloromethane/methanol/acetic acid/water (9:1:0.1:0.1).

ES(+)-MS: 749.3 (M+H)$^+$

Example 7

((R,S)-3-Benzyl-4-methyl-4-(4-(3-(2-phenylethyl)ureidomethyl)phenyl)-2,5-dioxoimidazolidin-1-yl)acetyl-L-aspartyl-L-phenylglycine

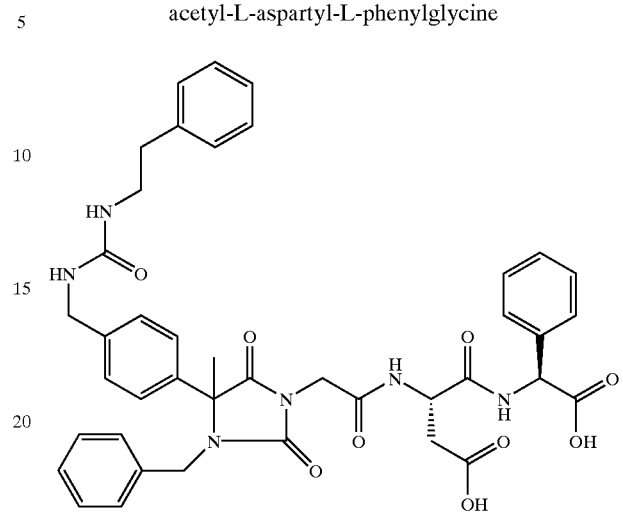

The synthesis was carried out analogously to Example 4. After cleavage of the tert-butyl ester using 90% strength trifluoroacetic acid, the crude product was purified by chromatography on silica gel using dichloromethane/methanol/acetic acid/water (9:1:0.1:0.1).

ES(+)-MS: 763.3 (M+H)$^+$

Investigation of the biological activity

As a test method for the activity of the compounds of the formula Ib on the interaction between VCAM-1 and VLA-4, an assay is used which is specific for this interaction. The cellular binding components, i.e. the VLA-4-integrins, are offered in their natural form as surface molecules on human U937 cells (ATCC CRL 1593), which belong to the group of leucocytes. As specific binding components, recombinant soluble fusion proteins prepared by genetic engineering and consisting of the extracytoplasmic domains of human VCAM-1 and the constant region of a human immunoglobulin of the subclass IgG1 are used.

Test method

Assay for the measurement of the adhesion of U937 cells (ATCC CRL 1593) to hVCAM-1(1–3)-IgG 1. Preparation of human VCAM-1(1–3)-IgG and human CD4-IgG A genetic construct for the expression of the extracellular domains of human VCAM-1 was employed, associated with the genetic sequence of the heavy chain of human immunoglobulin IgG-1 (hinge, CH2 and CH3 regions), from Dr. Brian Seed, Massachusetts General Hospital, Boston, USA. The soluble fusion protein hVCAM-1(1–3)-IgG contained the three amino-terminal extracellular immunoglobulin-like domains of human VCAM-1 (Damle and Aruffo, Proc. Natl. Acad. Sci. USA 1991, 88, 6403). CD4-IgG (Zettlmeissl et al., DNA and Cell Biology 1990, 9, 347) served as a fusion protein for negative controls. The recombinant proteins were expressed as soluble proteins after DEAE/dextran-mediated DNA-transfection in COS cells (ATCC CRL1651) according to standard procedures (Ausubel et al., Current protocols in molecular biology, John Wiley & Sons, Inc., 1994).

2. Assay for measurement of the adhesion of U937 cells to hVCAM-1(1–3)-IgG 2.1 96-well microtiter test plates (Nunc Maxisorb) were incubated at room temperature for 1 hour with 100 µl/well of a goat-anti-human IgG antibody solution (10 μg/ml in 50 mM Tris, pH 9.5). After removing the antibody solution, washing was carried out once with PBS.

2.2 150 μl/well of a blocking buffer (1% BSA in PBS) was incubated on the plates at room temperature for 0.5 hours. After removing the blocking buffer, washing was carried out once with PBS.

2.3 100 μl per well of a cell culture supernatant of transfected COS cells were incubated on the plates at room temperature for 1.5 hours. The COS cells were transfected with a plasmid which codes for the three N-terminal immunoglobulin-like domains of VCAM-1, coupled to the Fc part of human $IgG_1$ (hVCAM-1(1–3)-IgG). The content of hVCAM-1(1–3)-IgG was about 0.5–1 μg/ml. After removing the culture supernatant, washing was carried out once with PBS.

2.4 The plates were incubated at room temperature for 20 minutes with 100 μl/well of Fc receptor blocking buffer (1 mg/ml of γ-globulin, 100 mM NaCl, 100 μM $MgCl_2$, 100 μM $MnCl_2$, 100 μM $CaCl_2$, 1 mg/ml BSA in 50 mM HEPES, pH 7.5). After removing the Fc receptor blocking buffer, washing was carried out once with PBS.

2.5 20 μl of binding buffer (100 μM NaCl, 100 μM $MgCl_2$, 100 μM $MnCl_2$, 100 μM $CaCl_2$, 1 mg/ml BSA in 50 mM HEPES, pH 7.5), were initially introduced, the substances to be tested were added in 10 μl of binding buffer and the mixture was incubated for 20 minutes. As controls, antibodies against VCAM-1 (BBT, No. BBA6) and against VLA-4 (Immunotech, No. 0764) were used.

2.6 U937 cells were incubated in Fc receptor blocking buffer for 20 minutes and then pipetted in at a concentration of $1 \times 10^6$/ml and in an amount of 100 μl per well (final volume 125 μl/well).

2.7 The plates were slowly immersed at an angle of 45° in stop buffer (100 mM NaCl, 100 μM $MgCl_2$, 100 μM $MnCl_2$, 100 μM $CaCl_2$ in 25 mM Tris, pH 7.5) and shaken off. The process was repeated.

2.8 50 μl/well of a dye solution (16.7 μg/ml of Hoechst dye 33258, 4% formaldehyde, 0.5% Triton X-100 in PBS) were then incubated on the plates for 15 minutes.

2.9 The plates were shaken off and slowly immersed at an angle of 45° in stop buffer (100 mM NaCl, 100 μM $MgCl_2$, 100 μM $MnCl_2$, 100 μM $CaCl_2$ in 25 mM tris, pH 7.5). The process was repeated. Then, with the liquid, measurements were made in a cytofluorimeter (Millipore) (sensitivity: 5; filter: excitation wavelength: 360 nm, emission wavelength: 460 nm).

The intensity of the light emitted by the stained U937 cells is a measure of the number of the U937 cells adhered to the hVCAM-1(1–3)-IgG and remaining on the plate and thus a measure of the ability of the added test substance to inhibit this adhesion. From the inhibition of the adhesion at various concentrations of the test substance, the concentration $IC_{50}$ which leads to an inhibition of adhesion by 50% was calculated.

The following test results were obtained:

| Example | U937/VCAM-1 cell adhesion test $IC_{50}$ (μM) |
| --- | --- |
| 1 | 30 |
| 2 | 27.7 |
| 3 | 2.8 |
| 4 | 14 |
| 5 | 9 |
| 6 | 6.5 |
| 7 | 20 |

It will be apparent to those skilled in the art that various modifications and variations can be made to the compounds, compositions, kits, and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 19647381.0, for which benefit under 35 USC § 119 is claimed, is expressly incorporated herein in its entirety.

What is claimed is:
1. A compound of the formula I

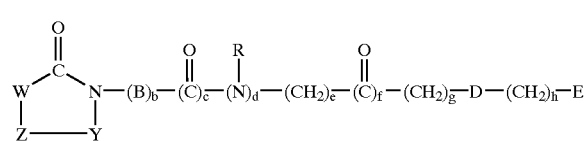

in which

W is $R^1$-A-C($R^{13}$);

Y is a carbonyl, thiocarbonyl or methylene group;

Z is N($R^0$), oxygen, sulfur or a methylene group;

A is a bivalent radical from the group consisting of ($C_1$–$C_6$)-alkylene, ($C_3$–$C_{12}$)-cycloalkylene, ($C_1$–$C_6$)-alkylene-($C_3$–$C_{12}$)-cycloalkyl, phenylene, phenylene-($C_1$–$C_6$)-alkyl, ($C_1$–$C_6$)-alkylenephenyl, ($C_1$–$C_6$)-alkylenephenyl-($C_1$–$C_6$)-alkyl, phenylene-($C_2$–$C_6$)-alkenyl or a bivalent radical of a 5- or 6-membered saturated or unsaturated ring which can contain 1 or 2 nitrogen atoms and can be mono- or disubstituted by ($C_1$–$C_6$)-alkyl or doubly bonded oxygen or sulfur, or is a direct bond;

B is a bivalent radical from the group consisting of ($C_1$–$C_6$)-alkylene, ($C_2$–$C_6$)-alkenylene, phenylene, phenylene-($C_1$–$C_3$)-alkyl, ($C_1$–$C_3$)-alkylenephenyl, where the bivalent ($C_1$–$C_6$)-alkylene radical can be unsubstituted or substituted by a radical from the group consisting of ($C_1$–$C_8$)-alkyl, ($C_2$–$C_8$)-alkenyl, ($C_2$–$C_8$)-alkynyl, ($C_3$–$C_{10}$)-cycloalkyl, ($C_3$–$C_{10}$)-cycloalkyl-($C_1$–$C_6$)-alkyl, optionally substituted ($C_6$–$C_{14}$)-aryl, ($C_6$–$C_{14}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

D is C($R^2$)($R^3$);

E is tetrazolyl, ($R^8$O)$_2$P(O), HOS(O)$_2$, $R^9$NHS(O)$_2$ or $R^{10}$CO;

R is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl and heteroaryl-($C_1$–$C_8$)-alkyl optionally substituted in the heteroaryl radical, where alkyl radicals can be mono- or polysubstituted by fluorine;

$R^0$ is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, CHO, ($C_1$–$C_8$)-alkyl-CO, ($C_3$–$C_{12}$)-cycloalkyl-CO, ($C_3$–$C_{12}$)-cycloalkyl-($C_1$–$C_8$)-alkyl-CO, ($C_6$–$C_{12}$)-bicycloalkyl-CO, ($C_6$–$C_{12}$)-bicycloalkyl-($C_1$–$C_8$)-alkyl-CO, ($C_6$–$C_{12}$)-tricycloalkyl-CO, ($C_6$–$C_{12}$)-tricycloalkyl-($C_1$–$C_8$)-alkyl-CO, optionally substituted ($C_6$–$C_{14}$)-aryl-CO, ($C_6$–$C_{14}$)-aryl-($C_1$–$C_8$)-alkyl-CO optionally substituted in the aryl radical, optionally substituted heteroaryl-CO, heteroaryl-($C_1$–$C_8$)-alkyl-CO optionally substituted in the heteroaryl radical, ($C_1$–$C_8$)-alkyl-S(O)$_n$, ($C_3$–$C_{12}$)-cycloalkyl-S(O)$_n$, ($C_3$–$C_{12}$)-cycloalkyl-($C_1$–$C_8$)-alkyl-S(O)$_n$, ($C_6$–$C_{12}$)-bicycloalkyl-S(O)$_n$, ($C_6$–$C_{12}$)-bicycloalkyl-($C_1$–$C_8$)-alkyl-S(O)$_n$, ($C_6$–$C_{12}$)-tricycloalkyl-S(O)$_n$, ($C_6$–$C_{12}$)-tricycloalkyl-($C_1$–$C_8$)-alkyl-S(O)$_n$, optionally substituted ($C_6$–$C_{14}$)-aryl-S(O)$_n$, ($C_6$–$C_{14}$)-aryl-($C_1$–$C_8$)-alkyl-S(O)$_n$ optionally substituted in the aryl radical, optionally substituted heteroaryl-S(O)$_n$ or heteroaryl-($C_1$–$C_8$)-alkyl-S(O)$_n$ optionally substituted in the heteroaryl radical, where n is 1 or 2;

$R^1$ is one of the radicals —S—$R^{21}$, —S—S—$R^{21}$, —S(O)—$R^{22}$, —S(O)$_2$—$R^{22}$, —S—O$R^{21}$, —S(O)—O$R^{21}$, —S(O)$_2$—O$R^{21}$, —S—N($R^{21}$)—$R^{28}$, —S(O)—N($R^{21}$)—$R^{28}$, —S(O)$_2$—N($R^{21}$)—$R^{28}$, —S—C(O)—$R^{21}$, —S—C(O)—O$R^{22}$, —S—C(S)—S$R^{22}$, —S—C(O)—N($R^{21}$)—$R^{28}$, —S—C(S)—N($R^{21}$)—$R^{28}$, —O—C(O)—$R^{21}$, —O—C(S)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—O$R^{21}$, —O—S(O)—O$R^{21}$, —O—S(O)$_2$—N($R^{21}$)—$R^{28}$, —O—S(O)—N($R^{21}$)—$R^{28}$, —O—S(O)$_2$—$R^{22}$, —O—S(O)—$R^{22}$, —O—P(O)(O$R^{21}$)$_2$, —O—P(O)(O$R^{21}$)—N($R^{21}$)—$R^{28}$, —O—P(O)(N($R^{21}$)—$R^{28}$)$_2$, —N($R^{29}$)—C(O)—O$R^{22}$, —N($R^{28}$)—C(O)—S$R^{22}$, —N($R^{28}$)—C(S)—O$R^{22}$, —N($R^{28}$)—C(S)—S$R^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —N($R^{28}$)—P(O)(O$R^{21}$)$_2$, —N($R^{28}$)—P(O)(O$R^{21}$)—N($R^{21}$)—$R^{28}$, —N($R^{28}$)—P(O)(($R^{21}$)—$R^{28}$)$_2$, —N($R^{28}$)—P(O)($R^{22}$)—O$R^{21}$, —N($R^{28}$)—P(O)($R^{22}$)—N($R^{21}$)—$R^{28}$, —N($R^{28}$)—P(O)($R^{22}$)$_2$, —P(O)(O$R^{21}$)$_2$, —P(O)(O$R^{21}$)—N($R^{21}$)—$R^{28}$, —P(O)(N($R^{21}$)—$R^{28}$)$_2$, —P(O)($R^{22}$)—O$R^{21}$, —P(O)($R^{22}$)—N($R^{21}$)—$R^{28}$, —P(O)($R^{22}$)$_2$, —C(S)—$R^{21}$, —C(S)—S$R^{21}$, —C(S)—N($R^{21}$)—$R^{28}$, cyano, halogen, nitro or methylenedioxy or the radical of an optionally substituted, 5- to 14-membered, mono- or polycyclic, saturated or unsaturated heterocyclic ring of the formula

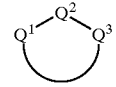

in which $Q^1$ is —C($R^{21}$)$_2$—, =C($R^{21}$)—, —N($R^{28}$)—, —O— or —S—;

$Q^2$ is —S(O)— or —S(O)$_2$—;

$Q^3$ is —C($R^{21}$)$_2$—, =C($R^{21}$)—, —N($R^{28}$)—, —O—, —S—, —C($R^{21}$)(—)— or —N(—), where the heterocyclic ring is optionally bonded to the group A via the free bond in the groups —C($R^{21}$)(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen, ($C_1$–$C_8$)-alkyl, optionally substituted ($C_6$–$C_{14}$)-aryl, ($C_6$–$C_{14}$)-aryl-($C_1$ alkyl optionally substituted in the aryl radical or ($C_3$–$C_8$)-cycloalkyl;

$R^3$ is ($C_2$–$C_8$)-alkenylcarbonyl, ($C_2$–$C_8$)-alkynylcarbonyl, $R^4$CO, COO$R^4$, CON(CH$_3$)$R^4$, CONHR$^4$, CSNHR$^4$;

$R^4$ is hydrogen or ($C_1$–$C_{28}$)-alkyl which can optionally be mono- or polysubstituted by identical or different radicals selected from the group consisting of hydroxyl, hydroxycarbonyl, aminocarbonyl, mono- or di-(($C_1$–$C_{18}$)-alkyl)aminocarbonyl, amino-($C_2$–$C_{18}$)-alkylaminocarbonyl, amino-($C_1$–$C_3$)-alkylphenyl-($C_1$–$C_3$)-alkylaminocarbonyl, ($C_1$–$C_{18}$)-alkylcarbonylamino-($C_1$–$C_3$)-alkylphenyl-($C_1$–$C_3$)-alkylaminocarbonyl, ($C_1$–$C_{18}$)-alkylcarbonylamino-($C_2$–$C_{18}$)-alkylaminocarbonyl, ($C_6$–$C_{14}$)-aryl-($C_1$–$C_8$)-alkoxycarbonyl optionally substituted in the aryl radical, amino, mercapto, ($C_1$–$C_{18}$)-alkoxy, ($C_1$–$C_{18}$)-alkoxycarbonyl, Het-CO, optionally substituted ($C_3$–$C_8$)-cycloalkyl, HOS(O)$_2$—($C_1$–$C_3$)-alkyl, $R^9NHS(O)_2$—$(C_1$–$C_3)$-alkyl, $(R^8O)_2P(O)$—$(C_1$–$C_3)$-alkyl, tetrazolyl-$(C_1$–$C_3)$-alkyl, halogen, nitro, trifluoromethyl or the radical $R^5$;

$R^5$ is optionally substituted $(C_6$–$C_{14})$-aryl, $(C_6$–$C_{14})$-aryl-$(C_1$–$C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1$–$C_{18})$-alkyl, $(C_1$–$C_{18})$-alkoxy, halogen, nitro, amino and trifluoromethyl;

$R^6$ is $R^7R^8N$, $R^7O$ or $R^7S$ or an amino acid side chain, a natural or unnatural amino acid, imino acid, optionally N—$(C_1$–$C_8)$-alkylated or N—$((C_6$–$C_{14})$-aryl-$(C_1$–$C_8)$-alkylated) aza-amino acid or a dipeptide radical wherein the aryl group of the aza-amino acid is optionally substituted and/or in which the peptide bond can be reduced to —NH—$CH_2$—, esters and amides thereof, wherein hydrogen or hydroxymethyl can optionally stand in place of free functional groups and/or where free functional groups can be protected by protective groups customary in peptide chemistry;

$R^7$ is hydrogen, $(C_1$–$C_{18})$-alkyl, $(C_6$–$C_{14})$-aryl-$(C_1$–$C_8)$-alkyl, $(C_1$–$C_{18})$-alkylcarbonyl, $(C_1$–$C_{18})$-alkoxycarbonyl, $(C_6$–$C_{14})$-arylcarbonyl, $(C_6$–$C_{14})$-aryl-$(C_1$–$C_8)$-alkylcarbonyl or $(C_6$–$C_{14})$-aryl-$(C_1$–$C_{18})$-alkyloxycarbonyl, where the alkyl groups are optionally be substituted by an amino group and/or where the aryl radicals can be mono- or polysubstituted by identical or different radicals from the group consisting of $(C_1$–$C_8)$-alkyl, $(C_1$–$C_8)$-alkoxy, halogen, nitro, amino and trifluoromethyl, or $R^7$ is a natural or unnatural amino acid, imino acid, optionally N—$(C_1$–$C_8)$-alkylated or N—$((C_6$–$C_{14})$-aryl-$(C_1$–$C_8)$-alkylated) aza-amino acid or a dipeptide radical wherein the aryl group of the aza-amino acid is optionally substituted and/or in which the peptide bond can be reduced to —NH—$CH_2$—;

$R^8$ is hydrogen, $(C_1$–$C_{18})$-alkyl, optionally substituted $(C_6$–$C_{14})$-aryl or $(C_6$–$C_{14})$-aryl-$(C_1$–$C_8)$-alkyl optionally substituted in the aryl radical;

$R^9$ is hydrogen, aminocarbonyl, $(C_1$–$C_{18})$-alkylaminocarbonyl, $(C_3$–$C_8)$-cycloalkylaminocarbonyl, optionally substituted $(C_6$–$C_{14})$-arylaminocarbonyl, $(C_1$–$C_{18})$-alkyl, optionally substituted $(C_6$–$C_{14})$-aryl or $(C_3$–$C_8)$-cycloalkyl;

$R^{10}$ is hydroxyl, $(C_1$–$C_{18})$-alkoxy, $(C_6$–$C_{14})$-aryl-$(C_1$–$C_8)$-alkoxy optionally substituted in the aryl radical, optionally substituted $(C_6$–$C_{14})$-aryloxy, amino or mono- or di-$((C_1$–$C_{18})$-alkyl)amino;

$R^{13}$ is hydrogen, $(C_1$–$C_6)$-alkyl, optionally substituted $(C_6$–$C_{14})$-aryl, $(C_6$–$C_{14})$-aryl-$(C_1$–$C_8)$-alkyl optionally substituted in the aryl radical, $(C_3$–$C_8)$-cycloalkyl or $(C_3$–$C_8)$-cycloalkyl-$(C_1$–$C_8)$-alkyl;

$R^{21}$ is hydrogen, $(C_1$–$C_8)$-alkyl, hydroxy-$(C_1$–$C_8)$-alkyl, $(C_2$–$C_8)$-alkenyl, $(C_3$–$C_{12})$-cycloalkyl, $(C_3$–$C_{12})$-cycloalkyl-$(C_1$–$C_8)$-alkyl, optionally substituted $(C_6$–$C_{14})$-aryl, $(C_6$–$C_{14})$-aryl-$(C_1$–$C_8)$-alkyl optionally substituted in the aryl radical, optionally substituted heteroaryl or heteroaryl-$(C_1$–$C_8)$-alkyl optionally substituted in the heteroaryl radical, where alkyl radicals can be optionally monosubstituted or polysubstituted by fluorine and the radicals $R^{21}$ can be identical or different if they occur two or more times;

$R^{22}$ is $(C_1$–$C_8)$-alkyl, hydroxy-$(C_1$–$C_8)$-alkyl, $(C_2$–$C_8)$-alkenyl, $(C_3$–$C_{12})$-cycloalkyl, $(C_3$–$C_{12})$-cycloalkyl-$(C_1$–$C_8)$-alkyl, optionally substituted $(C_6$–$C_{14})$-aryl, $(C_6$–$C_{14})$-aryl-$(C_1$–$C_8)$-alkyl optionally substituted in the aryl radical, optionally substituted heteroaryl or heteroaryl-$(C_1$–$C_8)$-alkyl optionally substituted in the heteroaryl radical, where alkyl radicals can be monosubstituted or polysubstituted by fluorine and the radicals $R^{22}$ can be identical or different if they occur two or more times;

$R^{28}$ is one of the radicals $R^{21}$—, $R^{21}N(R^{21})$—, $R^{21}C(O)$—, $R^{22}O$—$C(O)$—, $R^{21}N(R^{21})$—$C(O)$— or $R^{21}N(R^{21})$—$C(=N(R^{21}))$—;

$R^{29}$ is one of the radicals $R^{22}$—, $R^{21}N(R^{21})$—, $R^{21}C(O)$—, $R^{22}O$—$C(O)$—, $R^{21}N(R^{21})$—$C(O)$— or $R^{21}N(R^{21})$—$C(=N(R^{21}))$—;

Het is the radical of a 5- to 10-membered, monocyclic or polycyclic heterocycle bonded via a nitrogen atom, which can be aromatic or partially unsaturated or saturated and which can contain one, two, three or four identical or different additional ring heteroatoms from the group consisting of oxygen, nitrogen and sulfur and which can be optionally substituted on carbon atoms and on additional ring nitrogen atoms, where there can be identical or different radicals $R^h$, $R^hCO$ or $R^hO$—CO as substituents on additional ring nitrogen atoms and $R^h$ is hydrogen, $(C_1$–$C_8)$-alkyl, $(C_3$–$C_8)$-cycloalkyl, $(C_3$–$C_8)$-cycloalkyl-$(C_1$–$C_8)$-alkyl, optionally substituted $(C_6$–$C_{14})$-aryl or $(C_6$–$C_{14})$-aryl-$(C_1$–$C_8)$-alkyl optionally substituted in the aryl radical;

b, c, and d are 1, e and f are 0; and g and h independently of one another are 0, 1, 2, 3, 4, 5 or 6;

or a stereoisomeric thereof, or a physiologically tolerable salt thereof.

2. A compound of the formula I as claimed in claim 1, in which

B is a bivalent radical from the group consisting of $(C_1$–$C_6)$-alkylene, $(C_2$–$C_6)$-alkenylene, phenylene, phenylene-$(C_1$–$C_3)$-alkyl, $(C_1$–$C_3)$-alkylenephenyl;

R and $R^0$ independently of one another are hydrogen, $(C_1$–$C_8)$-alkyl, $(C_3$–$C_{12})$-cycloalkyl, $(C_3$–$C_{12})$-cycloalkyl-$(C_1$–$C_8)$-alkyl, optionally substituted $(C_6$–$C_{14})$-aryl, $(C_6$–$C_{14})$-aryl-$(C_1$–$C_8)$-alkyl optionally substituted in the aryl radical, optionally substituted heteroaryl or heteroaryl-$(C_1$–$C_8)$-alkyl optionally substituted in the heteroaryl radical, where alkyl radicals can be mono- or polysubstituted by fluorine;

$R^4$ is hydrogen or $(C_1$–$C_{28})$-alkyl which can optionally be mono- or polysubstituted by identical or different radicals selected from the group consisting of hydroxyl, hydroxycarbonyl, aminocarbonyl, mono- or di-$((C_1$–$C_{18})$-alkyl)aminocarbonyl, amino-$(C_2$–$C_{18})$-alkylaminocarbonyl, amino-$(C_1$–$C_3)$-alkylphenyl-$(C_1$–$C_3)$-alkylaminocarbonyl, $(C_1$–$C_{18})$-alkylcarbonylamino-$(C_1$–$C_3)$-alkylphenyl-$(C_1$–$C_3)$-alkylaminocarbonyl, $(C_1$–$C_{18})$-alkylcarbonylamino-$(C_2$–$C_{18})$-alkylaminocarbonyl, $(C_6$–$C_{14})$-aryl-$(C_1$–$C_8)$-alkoxycarbonyl optionally substituted in the aryl radical, amino, mercapto, $(C_1$–$C_{18})$-alkoxy, $(C_1$–$C_{18})$-alkoxycarbonyl, optionally substituted $(C_3$–$C_8)$-cycloalkyl, $HOS(O)_2$—$(C_1$–$C_3)$-alkyl, $R^9NHS(O)_2$—

($C_1$–$C_3$)-alkyl, ($R^8O$)$_2$P(O)—($C_1$–$C_3$)-alkyl, tetrazolyl-($C_1$–$C_3$)-alkyl, halogen, nitro, trifluoromethyl or the radical $R^5$;

$R^{13}$ is hydrogen, ($C_1$–$C_6$)-alkyl, ($C_6$–$C_{14}$)-aryl-($C_1$–$C_8$)-alkyl optionally substituted in the aryl radical or ($C_3$–$C_8$)-cycloalkyl;

or a stereoisomer thereof, or a physiologically tolerable salt thereof.

3. A compound of the formula I as claimed in claim 1, in which $R^1$ is one of the radicals —S(O)—N($R^{21}$)—$R^{28}$, —S(O)$_2$—N($R^{21}$)—$R^{28}$, —O—C(O)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—N($R^{21}$)—$R^{28}$, —O—S(O)—N($R^{21}$)—$R^{28}$, —N($R^{29}$)—C(O)—O$R^{22}$—N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —C(S)—$R^{21}$, —C(S)—N($R^{21}$)—$R^{28}$ or cyano or the radical of an optionally substituted, 5- to 14-membered, mono- or polycyclic, saturated or unsaturated heterocyclic ring of the formula

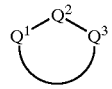

in which $Q^1$ is —C($R^{21}$)$_2$—, =C($R^{21}$)—, —N($R^{28}$)—, —O— or —S—;

$Q^2$ is —S(O)— or —S(O)$_2$—;

$Q^3$ is —C($R^{21}$)$_2$—, =C($R^{21}$)—, —N($R^{28}$)—, —O—, —S—, —C($R^{21}$)(—)— or —N(—)—, where the heterocyclic is optionally bonded to the group A via the free bond in the groups —C($R^{21}$)(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A; or a stereoisomer thereof, or a physiologically tolerable salt thereof.

4. A compound of the formula I as claimed in claim 1, in which $R^0$ is ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical; or a stereoisomeric thereof, or a physiologically tolerable salt thereof.

5. A compound of the formula I as claimed in claim 4, wherein $R^0$ is selected from the group consisting of biphenylylmethyl, naphthylmethyl, and benzyl, each of which is unsubstituted or monosubstituted or polysubstituted in the aryl radical; or a stereoisomeric thereof, or a physiologically tolerable salts thereof.

6. A compound of the formula I as claimed in claim 1, in which

A is a bivalent radical from the group consisting of methylene, ethylene, trimethylene, tetramethylene, pentamethylene, cyclohexylene, phenylene, phenylenemethyl, methylenephenyl, methylenephenylmethyl;

B is a bivalent radical from the group consisting of methylene, ethylene, trimethylene, tetramethylene, vinylene, phenylene, or substituted methylene or ethylene;

E is $R^{10}$CO;

R is hydrogen, ($C_1$–$C_6$)-alkyl or benzyl;

$R^0$ is ($C_1$–$C_8$)-alkyl, ($C_3$–$C_8$)-cycloalkyl, optionally substituted ($C_6$–$C_{14}$)-aryl or ($C_6$–$C_{14}$)-aryl-($C_1$–$C_8$)-alkyl optionally substituted in the aryl radical;

$R^1$ is one of the radicals —S(O)—N($R^{21}$)—$R^{28}$, —S(O)$_2$—N($R^{21}$)—$R^{28}$, —O—C(O)—$R^{21}$, —O—C(O)—O$R^{22}$, —O—C(O)—N($R^{21}$)—$R^{28}$, —O—C(S)—N($R^{21}$)—$R^{28}$, —O—S(O)$_2$—N($R^{21}$)—$R^{28}$, —O—S(O)—N($R^{21}$)—$R^{28}$, —N($R^{29}$)—C(O)—O$R^{22}$, —N($R^{28}$)—C(S)—$R^{21}$, —N($R^{28}$)—C(O)—N($R^{21}$)—$R^{28}$, —N($R^{28}$)—C(S)—N($R^{21}$)—$R^{28}$, —N($R^{28}$)—S(O)$_2$—$R^{22}$, —N($R^{28}$)—S(O)—$R^{22}$, —N($R^{28}$)—S(O)$_2$—O$R^{21}$, —N($R^{28}$)—S(O)—O$R^{21}$, —N($R^{28}$)—S(O)$_2$—N($R^{21}$)—$R^{28}$, —N($R^{28}$)—S(O)—N($R^{21}$)—$R^{28}$, —C(S)—$R^{21}$, —C(S)—N($R^{21}$)—$R^{28}$ or cyano or the radical of an optionally substituted, 5- to 14-membered, mono- or polycyclic, saturated or unsaturated heterocyclic ring of the formula

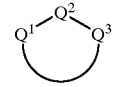

in which $Q^1$ is —C($R^{21}$)$_2$—, =C($R^{21}$)—, —N($R^{28}$)—, —O— or —S—;

$Q^2$ is —S(O)— or —S(O)$_2$—;

$Q^3$ is —C($R^{21}$)$_2$—, =C($R^{21}$)—, —N($R^{28}$)—, —O—, —S—, —C($R^{21}$)(—)— or —N(—)—, where the heterocyclic ring can be bonded to the group A via the free bond in the groups —C($R^{21}$)(—)— or —N(—)— representing $Q^3$ or via any other desired ring carbon atom and where, if the heterocyclic ring is bonded to a ring system contained in the group A, the heterocyclic ring can also be fused via two adjacent atoms to the ring system in the group A;

$R^2$ is hydrogen or ($C_1$–$C_8$)-alkyl;

$R^3$ is $R^4$CO, COO$R^4$, CONHR$^4$, or CSNHR$^4$;

and g and h independently of one another are the numbers 0, 1, 2 or 3;

or a stereoisomer thereof, or a physiologically tolerable salt thereof.

7. A compound of the formula I as claimed in claim 1, in which $R^{13}$ is ($C_1$–$C_6$)-alkyl, ($C_6$–$C_{14}$)-aryl-($C_1$–$C_8$)-alkyl optionally substituted in the aryl radical or ($C_3$–$C_8$)-cycloalkyl; or a stereoisomeric thereof, or a physiologically tolerable salts thereof.

8. The compound of the formula I as claimed in claim 1, wherein $R^3$ is COOR$^4$ or CONHR$^4$, and wherein —NHR$^4$ is the radical of an α-amino acid, an ω-amino-($C_2$–$C_8$)-alkylamide thereof, its ($C_1$–$C_8$)-alkyl ester, its ($C_6$–$C_{14}$)-aryl-($C_1$–$C_4$)-alkyl ester, or its derivative in which the carboxylic acid group is converted into the group Het-CO, or a stereoisomeric thereof, or a physiologically tolerable salt thereof.

9. The compound of the formula I as claimed in claim 8, wherein the radical of the α-amino acids is selected from the group consisting of valine, lysine, phenylglycine, phenylalanine, tryptophan, ($C_1$–$C_8$)-alkyl esters, ($C_6$–$C_4$)-aryl-($C_1$–$C_4$)-alkyl esters, and Het-CO derivatives thereof; or a stereoisomeric thereof, or a physiologically tolerable salt thereof.

10. A compound of the formula I as claimed in claim 1, in which simultaneously

Y is a carbonyl group;

Z is $N(R^0)$;

A is ethylene, trimethylene, tetramethylene, pentamethylene, cyclohexylene, phenylene, phenylenemethyl, methylenephenyl or methylenephenylmethyl;

B is an unsubstituted or substituted methylene radical;

E is $R^{10}CO$;

R is hydrogen or $(C_1-C_4)$-alkyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is one of the radicals $-O-C(O)-R^{21}$, $-O-C(O)-OR^{22}$, $-O-C(O)-N(R^{21})-R^{28}$, $-N(R^{29})-C(O)-OR^{22}$, $-N(R^{28})-C(O)-N(R^{21})-R^{28}$, $-N(R^{28})-C(S)-N(R^{21})-R^{28}$ or cyano;

$R^2$ is hydrogen;

$R^3$ is the radical $CONHR^4$;

$R^4$ is methyl which is substituted by hydroxycarbonyl and a radical from the group consisting of $(C_1-C_4)$-alkyl, phenyl and benzyl, or is methyl which is substituted by $(C_1-C_8)$-alkoxycarbonyl and a radical from the group consisting of $(C_1-C_4)$-alkyl, phenyl and benzyl, or is methyl which is substituted by Het-CO and a radical from the group consisting of $(C_1-C_4)$-alkyl, phenyl and benzyl;

$R^{10}$ is hydroxyl or $(C_1-C_8)$-alkoxy;

$R^{13}$ is $(C_1-C_6)$-alkyl, $(C_3-C_7)$-cycloalkyl or benzyl;

e, f and g are 0; and h is 1 or 2;

or a stereoisomer thereof, or a physiologically tolerable salt thereof.

11. A compound of the formula I as claimed in claim 1, in which a substituted methylene radical or substituted ethylene radical representing the group B carries as a substituent a radical from the group consisting of $(C_1-C_8)$-alkyl, $(C_2-C_6)$-alkenyl, $(C_2-C_6)$-alkynyl and $(C_3-C_8)$-cycloalkyl, $(C_3-C_8)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl, andheteroaryl-$(C_1-C_4)$-alkyl optionally substituted in the heteroaryl radical, or a stereoisomer thereof, or a physiologically tolerable salt thereof.

12. A compound of the formula I as claimed in claim 1, in which B is an unsubstituted methylene radical or a methylene radical which is substituted by a $(C_1-C_8)$-alkyl radical; or a stereoisomer thereof, or a physiologically tolerable salt thereof.

13. A compound of the formula I as claimed in claim 1, in which $R^1$ is one of the radicals $-O-C(O)-R^{21}$, $-O-C(O)-OR^{22}$, $-O-C(O)-N(R^{21})-R^{28}$, $-N(R^{29})-C(O)-OR^{22}$, $-N(R^{28})-C(O)-N(R^{21})-R^{28}$, $-N(R^{28})-C(S)-N(R^{21})-R^{28}$ or cyano; or a stereoisomer thereof, or a physiologically tolerable salt thereof.

14. A preparation comprising one or more of the compounds of the formula I as claimed in claim 1 or a stereoisomer thereof, or a physiologically tolerable salt thereof; and one or more pharmaceutically innocuous carriers and/or additives.

15. A kit comprising a VLA-4-antagonizing effective amount of one or more compounds of the formula I as claimed in claim 1 or a stereoisomer thereof, or a physiologically tolerable salt thereof; instructions for use; and one or more pharmaceutically inocuous carriers and/or additives.

16. A method for inhibiting adhesion of leukocytes to endothelial cells in a mammal, comprising administering to a subject in need thereof a VLA-4 antagonizing amount of a compound according to claim 1 for a time sufficient to antagonize VLA-4.

* * * * *